(12) United States Patent
Yeung et al.

(10) Patent No.: US 6,530,933 B1
(45) Date of Patent: Mar. 11, 2003

(54) METHODS AND DEVICES FOR FASTENING BULGING OR HERNIATED INTERVERTEBRAL DISCS

(76) Inventors: Teresa T. Yeung, 834 N. White Rd., San Jose, CA (US) 95127; Jeffrey E. Yeung, 834 N. White Rd., San Jose, CA (US) 95127

( * ) Notice: Subject to any disclaimer, the term of this patent is extended or adjusted under 35 U.S.C. 154(b) by 0 days.

(21) Appl. No.: 09/424,963
(22) PCT Filed: Sep. 15, 1999
(86) PCT No.: PCT/US99/21138
§ 371 (c)(1),
(2), (4) Date: Dec. 1, 1999
(87) PCT Pub. No.: WO00/40159
PCT Pub. Date: Jul. 13, 2000

Related U.S. Application Data

(60) Provisional application No. 60/114,545, filed on Dec. 31, 1998.

(51) Int. Cl.7 ............................................... A61B 17/04
(52) U.S. Cl. ..................... 606/151; 606/142; 606/143; 606/72; 606/78; 128/898
(58) Field of Search ........................ 128/898; 606/232, 606/72, 78

(56) References Cited

U.S. PATENT DOCUMENTS

| 4,037,603 A | 7/1977 | Wendorff |
| 4,396,139 A | 8/1983 | Hall et al. |
| 4,477,008 A | 10/1984 | Struble |
| 4,485,816 A | 12/1984 | Krumae |
| 4,493,323 A | 1/1985 | Albright et al. |
| 4,511,356 A | 4/1985 | Eroning et al. |
| 4,523,591 A | 6/1985 | Kaplan |
| 4,552,128 A | 11/1985 | Haber |
| 4,671,279 A | 6/1987 | Hill |
| 4,873,976 A | 10/1989 | Schreiber |
| 4,884,572 A | 12/1989 | Bays et al. |
| 4,895,148 A | 1/1990 | Bays et al. |
| 4,942,886 A | 7/1990 | Timmons |
| 4,944,295 A | 7/1990 | Gwathmey et al. |
| 4,976,715 A | 12/1990 | Bays et al. |

(List continued on next page.)

FOREIGN PATENT DOCUMENTS

WO 9718762 11/1996 ........... A61B/17/08

OTHER PUBLICATIONS

US 5,826,777, 10/1998, Green et al. (withdrawn)
Alfred J. Tria, Jr., M.D. Ligaments of the Knee, Churchill Livingstone, N.Y., 1995.
Freddie H. Fu, M.D. et.al., Knee Surgery, vol. 1, Williams & Wilkins, Baltimore, 1994.
John M. Siliske, M.D., Traumatic Disorders of the Knee, Springer–Verlag, N.Y., 1994.
Paul M. Aichroth, MS,FRCS, Knee Surgery, Raven Press, 1992.

(List continued on next page.)

*Primary Examiner*—Gary Jackson
(74) *Attorney, Agent, or Firm*—Gregory Smith & Associates; Carol Titus

(57) ABSTRACT

Methods and apparatuses for compressing and holding a bulging or herniated intervertebral disc. A number of fastener embodiments are disclosed, including a resiliently curved fastener, suture, screw, staple, tack and others. The curved fastener is resiliently straightened and loaded into a needle for delivery and deployment. In the intervertebral disc, the deployed fastener resumes the curvature to grip and hold the bulge. Alternatively, the suture is anchored and used to tie down the bulging tissue. The screw, staple or tack can also be used to securely fasten, compress and hold the bulge from impinging upon adjacent nerves or tissues.

41 Claims, 46 Drawing Sheets

U.S. PATENT DOCUMENTS

| | | |
|---|---|---|
| 5,002,563 A | 3/1991 | Pyka et al. |
| 5,026,373 A | 6/1991 | Ray |
| 5,040,715 A | 8/1991 | Green et al. |
| 5,053,047 A | 10/1991 | InBae |
| 5,059,206 A | 10/1991 | Winters |
| 5,067,957 A | 11/1991 | Jervis |
| 5,089,009 A | 2/1992 | Green |
| 5,129,902 A | 7/1992 | Globe |
| 5,147,362 A | 9/1992 | Globe |
| 5,154,189 A | 10/1992 | Oberlander |
| 5,171,252 A | 12/1992 | Friedland |
| 5,190,546 A | 3/1993 | Jervis |
| 5,209,756 A | 5/1993 | Seedhorn et al. |
| 5,257,713 A | 11/1993 | Green et al. |
| 5,258,012 A | 11/1993 | Luscombe et al. |
| 5,304,204 A | 4/1994 | Bregen |
| 5,320,633 A | 6/1994 | Allen et al. |
| 5,328,077 A | 7/1994 | Lou |
| 5,333,772 A | 8/1994 | Bothfoss et al. |
| 5,372,146 A | 12/1994 | Sander |
| 5,374,268 A | 12/1994 | Sander |
| 5,398,861 A | 3/1995 | Green |
| 5,413,272 A | 5/1995 | Green et al. |
| 5,413,584 A | 5/1995 | Schulze |
| 5,423,817 A | 6/1995 | Lin |
| 5,478,353 A | 12/1995 | Yoon |
| 5,520,700 A | 5/1996 | Beyar |
| 5,588,960 A | 12/1996 | Edwards et al. |
| 5,643,319 A | 7/1997 | Green et al. |
| 5,662,662 A | 9/1997 | Bishop et al. |
| 5,674,247 A | 10/1997 | Sohn .......................... 606/219 |
| 5,683,394 A | 11/1997 | Rinner |
| 5,702,462 A | 12/1997 | Oberlander |
| 5,715,987 A | 2/1998 | Kelly et al. |
| 5,782,832 A | 7/1998 | Larsen et al. |
| 5,782,864 A | 7/1998 | Lizardi |
| 5,794,834 A | 8/1998 | Hambin |
| 5,800,550 A | 9/1998 | Sertich |
| 5,817,109 A | 10/1998 | McGarry et al. |
| 5,829,662 A | 11/1998 | Allen et al. |
| 5,833,695 A | 11/1998 | Yoon |
| 5,843,084 A | 12/1998 | Hast et al. |
| 5,851,219 A | 12/1998 | Goble |
| 5,980,504 A | 11/1999 | Shankey et al. |

OTHER PUBLICATIONS

Johannes Lohnert et.al., Arthroscopic Surgery of the Knee, Georg Thieme Verlag, Thieme Medical Publisher Inc., Stuttgart, 1988.

Lanny L. Johnson, M.D., Arthroscopic Surgery Principles & Practice, vol. 1 and 2, 3rd Ed., The C.V. Mosby Comp., St. Louis, 1986.

R.P.Jakob et.al., The Knee and the Cruciate Liagments, Springer–Verlag, Berlin.

Edward C. Benzel, M.D., FACS, Spine Surger, vol. 1, Churchill Livingstone, 1999, New York.

Edward C. Benzel, M.D., FACS, Spine Surgery, vol. 2, Churchill Livingstone, N.Y. 1999.

Arthur H. White, M.D. et.al., Spine Care, vol. 1, Mosby, St. Louis, 1995.

Arthur H. White, M.D. et.al., Spine Care, vol. 2, Mosby, St. Louis, 1995.

Howard S. An, M.D. et.al., Spinal Instrumentation, Williams & Wilkins, Baltimore, 1992.

Augustus A. White III, M.D. et.al., Clinical Biomechanics of the Spine, 2nd Ed., J.B. Lippincott Company, Philadelphia, 1990.

Joseph C. Cauthen, M.D., F.A.C.S., Lumbar Spine Surgery, 2nd Ed., Williams & Wilkins, Baltimore, 1988.

Arthur H. White, M.D., et.al., Lumbar Spine Surgery, The C.V.Mosby Company, St. Louis, 1987.

Robert G.Watkins, M.D., et.al., Lumbar Discectomy and Laminectomy, An Aspen Publication, Rockville, Maryland, 1987.

Martin B. Camins, M.D. et.al., The Lumbar Spine, Raven Press, N.Y.

Urology Times, Apr. 1999.
Urology Times, Dec. 1997.
Urology Times, Jul. 1997.
Urology Times, Sep. 1996.
Urology Times, Mar. 1996.
Urology Times, Feb. 1996.
Urology Times, Sep. 1995.
Urology Times, Mar. 1995.
Urology Times, Jul. 1994.

David M. Albala, M.D, et.al., Color Atlas of Endourology, Lippincott–Raven Publishers, Philadelphia, 1999.

Philip H. Gordon, M.D., F.R.C.S.(C), Principle and Practice of Surgery for the Colon, Rectum, and Anus, 2nd Ed., Quality Medical Publishing, Inc., St. Louis, 1999.

Sam D. Graham, Jr., M.D., Glenn's Urologic Surgery, 5th Ed. Lippincott–Raven Publishers, Philadelphia, 1998.

R. John Nicholls, B.A., M.Chir., F.R.C.S. (Eng.), F.R.C.S., et.al, Sugery of the Colon & Rectum, Churchill Livingstone, N.Y., 1997.

William P. Cooney, M.D., et.al., The Wrist, Diagnosis and Operative Treatment, vol. 1, Mosby, St. Louis, 1998.

William P. Cooney, M.D. et.al., The Wrist, Diagnosis and Operative Treatment, vol. 2, Mosby, St. Louis, 1998.

David M.Lichtman, M.D. et.al., The Wrist and Its Disorders, 2nd Ed., W.B. Saunders Company, Philadelphia, 1997.

W. Bruce Conolly, FRCS, FRACS, FACS, Carpal Tunnel Syndrome, Color Atlas of Treatment, Medical Economics Books, Oradell, NJ, 1984.

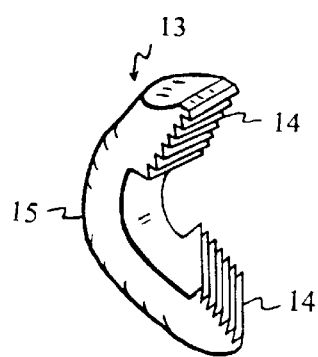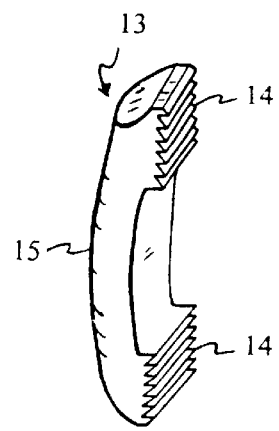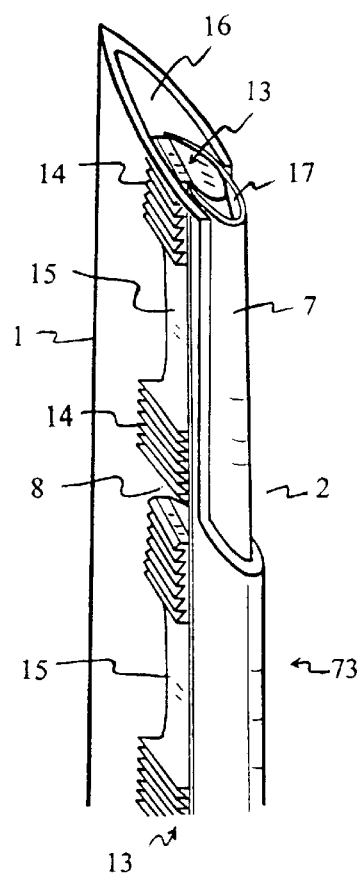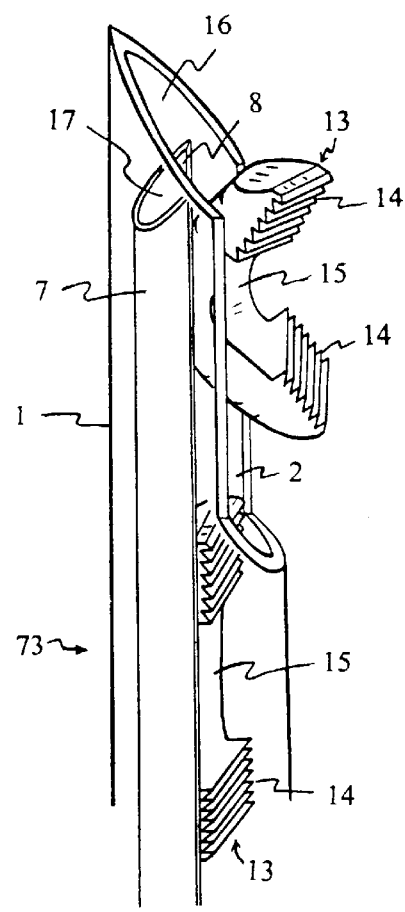
Figure 1
Figure 2
Figure 3
Figure 4

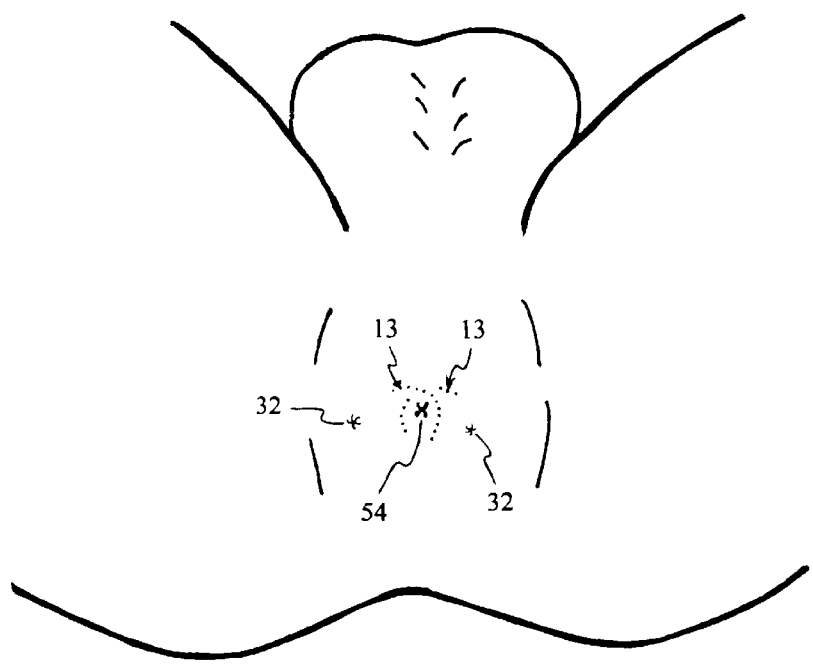
Figure 52
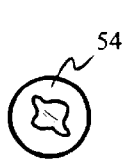
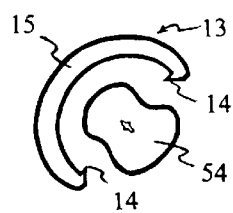
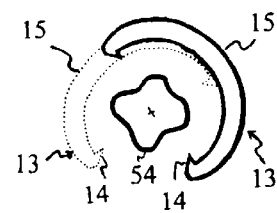
Figure 53A    Figure 53B    Figure 53C

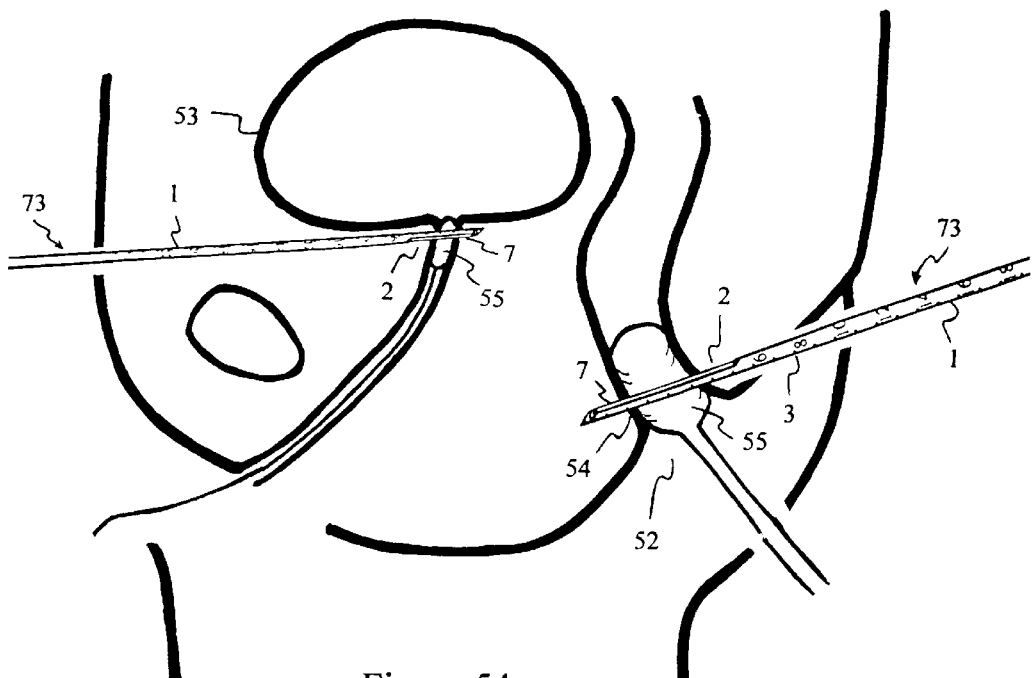
Figure 54
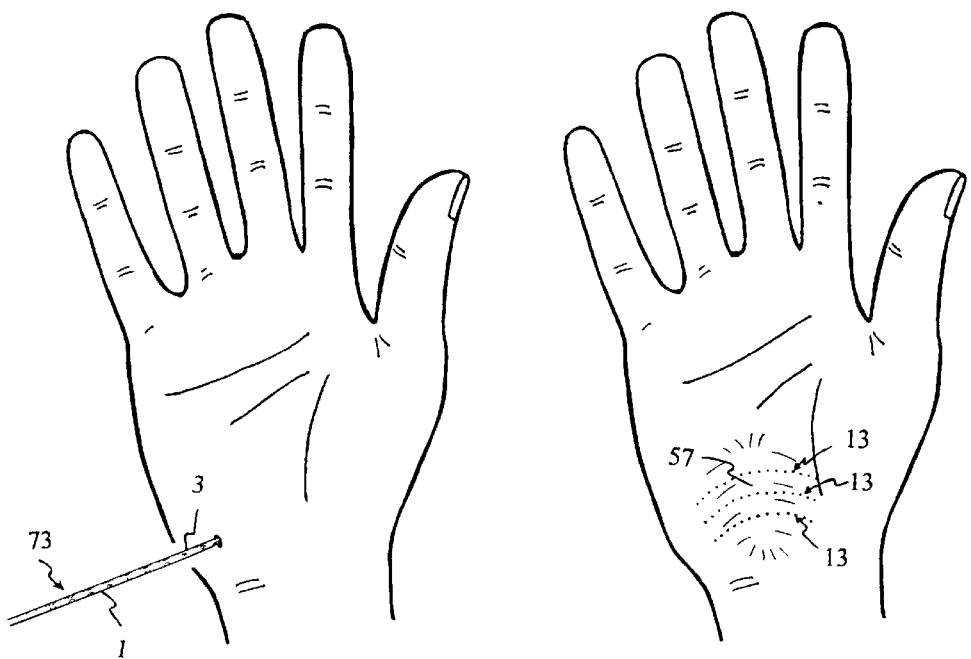
Figure 55
Figure 56

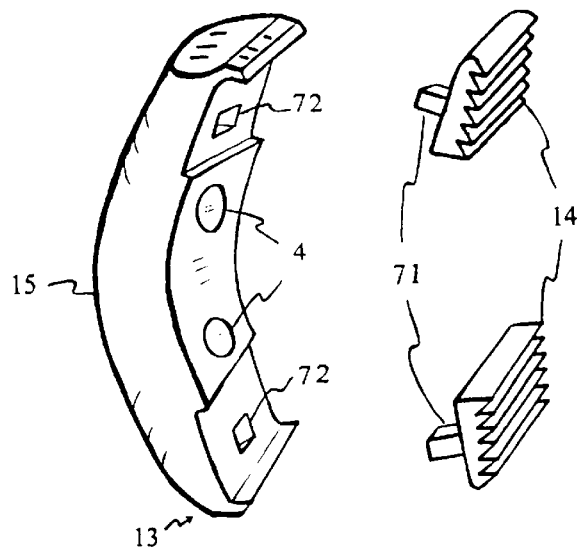
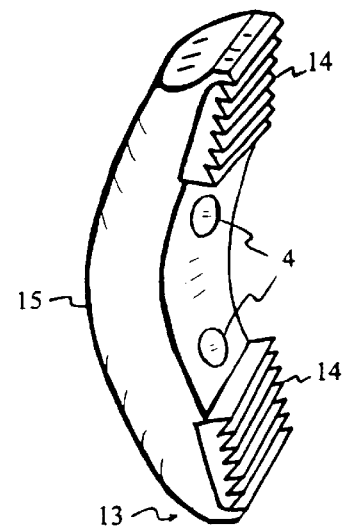
Figure 66
Figure 67
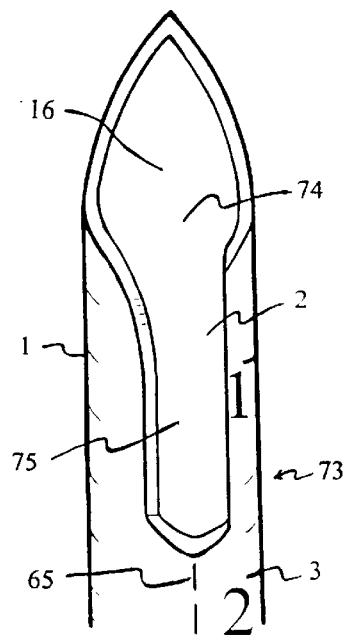
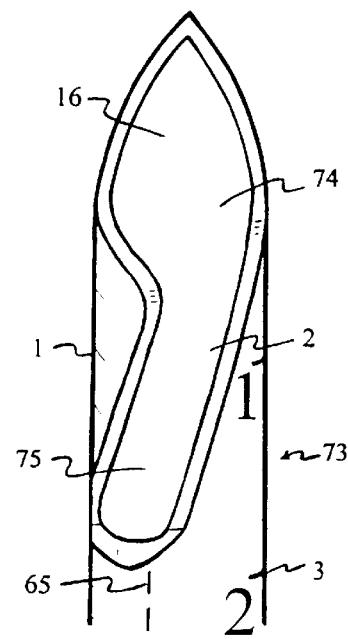
Figure 68
Figure 69

METHODS AND DEVICES FOR FASTENING BULGING OR HERNIATED INTERVERTEBRAL DISCS

CROSS REFERENCE TO OTHER APPLICATIONS

This application is a national stage application claiming priority of WIPO application number PCT/US99/21138, which claimed the benefit of U.S. Provisional Application No. 60/114,545 filed on Dec. 31, 1998, by Teresa T. Yeung.

FIELD OF THE INVENTION

The invention relates to methods and devices for fastening bulging or herniated discs. More particularly, the invention relates to devices for compressing the bulge or herniation of a damage intervertebral disc.

BACKGROUND, TRADITIONAL SURGICAL PRACTICES AND PRIOR INVENTIONS

In recent years, much attention has been given to controlling surgical costs. One of the cost-effective approaches is to accelerate the speed of recovery and shorten post-surgical hospital stays. In addition to lowering costs, for the comfort and safety of patients, minimally invasive or endoscopic surgeries are becoming more and more popular. The term "endoscopic" used in this invention encompasses arthroscopic, laparoscopic, hysteroscopic and other instrument viewing procedures. Endoscopy is a surgical procedure, which allows surgeons to manipulate instruments to view and operate the surgical sites through small incisions in the bodies of patients.

(A) Meniscal Tear

In order to minimize both the patients' trauma and potential damage to nerves, blood vessels and other tissues, it is clearly desirable to minimize the size and number of holes puncturing the patients. Take meniscal repair in the knee for example, the current arthroscopic procedure requires one hole for the arthroscope, one hole for a needle to deliver a suture and another hole for a suture-retrieving instrument to complete one suture stitch (Arthroscopic Surgery by L. Johnson, M.D.; Knee Surgery by F. Fu, MD, et al.; Traumatic Disorders of the Knee by J. Siliski, MD; and Knee Surgery Current Practice by P. Aichroth, FRCS et al.). A minimum of three holes is made for the arthroscopic repair. In some cases, surgeons also require a distractor, an external fixation device that is screwed in through skin to the bones, separating the femur from the tibia. This expands the knee joint and makes room to manipulate both the suture and the suture-retrieving instrument. Due to the tightness of joint space, often a needle or instrument can accidentally scrape and damage the smooth surface of the joint cartilage, which given time, can potentially lead to osteoarthritis years after the surgery.

Recently, instead of delivering, manipulating and retrieving a suture, often in a very tight surgical site, delivery of tacks with barbs (U.S. Pat. No. 5,702,462 to Oberlander, 1997; U.S. Pat. No. 5,398,861 to Green, 1995; U.S. Pat. No. 5,059,206 to Winters, 1991; U.S. Pat. No. 4,895,148 to Bays et. al., 1990; U.S. Pat. No. 4,884,572 to Bays et. al., 1989), staples (U.S. Pat. No. 5,643,319 to Green et. al., 1997) and fasteners (U.S. Pat. No. 5,843,084 to Hart et. al., 1998; U.S. Pat. No. 5,374,268 to Sander, 1994; U.S. Pat. No. 5,154,189 to Oberlander et. al., 1992) through a small opening to hold torn tissue, such as the meniscus, in place have been implemented. Unfortunately, very few, if any, of these tacks, staples and fasteners have the holding strength to meet the standard set by sutures.

During the insertion of these devices into tissues, the barbs carve their way into their final holding position. Unavoidably, the carving damages the tissue, and thus weakens it thereby decreasing the holding strength of the freshly inserted devices. As tension is applied to the fastened tissue, it is not surprising that the barbs can lose their grip, slip and creep along the carved paths created during insertion, leaving gaps in the supposed closure sites. The creeping problem of fastening devices is particularly evident in slow healing tissues, such as menisci, and also in tissues providing high tensile strength, such as ligaments and tendons. Since gaps are present, the torn tissue does not reattach and heal, even with the passage of time.

Non-biodegrdable fasteners often have the problem of device migration, which can be devastating, especially into nerves, joints or vessels, after numerous cycles of tissue remodeling.

In summary, currently most of the tacks or fasteners have one or more of the following drawbacks: (1) weak holding strength, (2) creeping and leaving gaps in the repair site, and (3) potential migration into sensitive tissues.

Numerous staples (U.S. Pat. No. 5,829,662 to Allen et. al., 1998; U.S. Pat. No. 5,826,777 to Green et. al., 1998; U.S. Pat. No. 5,817,109 to McGarry et. al., 1998; U.S. Pat. No. 5,794,834 to Hamblin et. al., 1998; U.S. Pat. No. 5,715,987 to Kelley et. al., 1998; U.S. Pat. No. 5,662,662 to Bishop et. al., 1997; U.S. Pat. No. 5,413,584 to Schulze, 1995; U.S. Pat. No. 5,333,772 to Rothfuss et. al., 1994; U.S. Pat. No. 5,304,204 to Bregen, 1994; U.S. Pat. No. 5,257,713 to Green et. al., 1993; U.S. Pat. No. 5,089,009 to Green, 1992; U.S. Pat. No. 5,002,563 to Pyka et. al., 1991; U.S. Pat. No. 4,944,295 to Gwathmey, 1990; U.S. Pat. No. 4,671,279 to Hill, 1987; U.S. Pat. No. 4,485,816 to Krumme, 1984; U.S. Pat. No. 4,396,139 to Hall et. al., 1983) are designed and used for shallow penetration of the staple, mostly to fasten superficial tissues only.

The term "fastener" used in this invention encompasses tacks, staples, screws, clamps and other tissue holding devices.

(B) Anterior Cruciate Ligament Tear

Meniscal damage often accompanies a torn anterior cruciate ligament, ACL, which stabilizes the femoro-tibial joint. Due to the linear orientation of the collagen fibers and the enormous tensile strength required of the ACL, it is often difficult to reattach the ligament by suture. When tensile forces are applied, the suture cuts and tears the collagen fibers along their linear orientation. Therefore, the traditional ACL repair is to abandon the torn ACL altogether. To replace the ACL, a strip of patellar ligament is harvested from the patient. Two bone holes are drilled, one through the tibia and another through the femur. The strip of patellar ligament is threaded through the bone holes. Both ends of the patellar ligaments are then stapled to the anterior surfaces of femur and tibia through incisions of skin covering each bone. The traditional ACL repair is an invasive surgery. To minimize the degree of invasiveness and eliminate opening the skin for ligament stapling, bone fixation devices (U.S. Pat. No. 5,147,362 to Goble, 1992, U.S. Pat. No. 5,129,902 to Goble, et. al. 1992) are designed to grip the ligament replacement inside the drilled hole of the bone.

(C) Bulging or Herniated Disc

Low-back pain is one of the most prevalent and debilitating ailments of mankind. For many people, no position can ease the pain or numbness, not even bed rest. It is often the reason for decreased productivity due to loss of work hours, addiction to pain-killing drugs, emotional distress, prolonged hospital stays, loss of independent living, unplanned early retirements, and even financial ruin. Some may experience it occasionally; others suffer from it for years. One common reason for this chronic pain is the bulging or hemiation of an intervertebral disc, which can cause sciatica The traditional surgical treatment for a bulging or herniated disc is a series of tissue removing, filling and supporting procedures: (1) laminectomy, removal of the lamina from the vertebra which covers part of the herniated disc, (2) discectomy, removal of the disc, (3) bone harvesting usually from the patient's iliac crest, (4) bone cement filling of the donor site, (5) donor bone packing into the vacant disc space, (6) adjacent vertebra supporting with rods, connectors, wire and screws, and finally, (7) surgical site closing.

After a discectomy, numerous postoperative complications can occur. The major ones are lumbar scarring and vertebral instability. The scar tissue extends and encroaches upon the laminectomy site and intervertebral foramen, then once again, pain returns, which leads to more surgery. In fact, re-operation is very common. Unfortunately, the success rate of re-operation is often less, in some cases, far less than the first. More operations lead to more scarring and more pain. Current emphasis to the patients is to avoid surgical procedures, unless the pain and inconveniences are absolutely unbearable.

Even for the fortunate patients with long term success following discectomies twenty years ago, their isokinetic test results clearly indicate weaknesses compared to populations without discectomies.

There was and still is increasing interest in less invasive surgical techniques on the spine to reduce both trauma and cost. The major objectives of surgery on bulging or herniated lumbar discs are (1) decompression of the involved nerve root or roots, and (2) preservation of bony spine, joints and ligaments.

Chymopapain is an enzyme used to digest away the nucleus pulposus, the gel-like substance in the central portion of the disc, which then creates space for the bulging part of the disc to pull back from the encroached nerve root. The needle for injecting the chymopapain is accurately guided to the mid-portion of the disc by a stereotaxic device. The overall success rate is documented as high as 76%. However, some patients are allergic to the treatment and die from anaphylaxis. Some others suffer from serious neuralgic complications, including paraplegia, paresis, cerebral hemorrhage and transverse myelitis (Lumbar Spine Surgery, Arthur White, M.D., Richard Rothman, M.D., Charles Ray, M.D.)

Percutaneous nuclectomy is an alternative method for removing nucleus pulposus without the allergic reaction of chymopapain. Similar to chymopapain injection, a needle followed by a tube-like instrument is guided and confirmed by anteroposterior and lateral fluoroscopy. The nucleus pulposus is then removed by mechanical means or by vacuum. As a result, a void is created within the disc and the bulging decreases, like the air being released from a worn out tire, with the hope that the bulging portion of the disc will recede and no longer encroach upon the adjacent nerve root. This type of procedure is often referred to as a decompression procedure. Unfortunately, there is no guarantee that the decompression will reduce enough bulging or herniation to alleviate pain.

Regarding immediate postoperative complications, percutaneous nuclectomy appears to be safer than either discectomy or chymopapain. There is little epidural scarring, allergic reactions, or serious neurologic complications. However, the case history using this percutaneous procedure has been relatively short, and the long-term outcome is not yet known.

The function of the nucleus pulposus, with its high water absorbing composition of mucoprotein and mucopolysaccharides, is to sustain prolonged compression during the day, and to resiliently re-inflate and re-establish disc height during the night. The pulposus is retained and surrounded by layers of cartilaginous annulus. Together the pulposus and the annulus behave as a resilient and cushioning water balloon. In the erect position, the weight of the body constantly compresses upon a stack of these water balloons alternating between a series of vertebrae. During constant compression, the pulposus in each disc also behaves as a water reservoir, which is slowly and constantly being squeezed and drained of its water content through the end plates connected to the vertebrae. As a result, the disc height decreases throughout the day. During bed rest, the weight of the body no longer compresses the disc. Due to the water absorbing nature of the nucleus pulposus, the flow of water is now reversed from the vascular vertebrae back into the mucoprotein and polysaccharides. As a result, the disc height is reestablished, ready to provide support for another day (Clinical Biomechanics of the Spine, 2nd ed., Augustus White, M.D., Manohar Panjabi, Ph.D.).

Aging, poor posture and trauma from heavy lifting contribute to an increase in annular fibrotic elements. The disc dries out and greatly loses height between vertebrae. Bone around the dried out disc grows a rim and spurs, which protrude and invade the intervertebral foramina and infringe upon nearby nerves. This continual, painful bone growth process causes stenosis.

After the removal of the water absorbing and water retaining pulposus by the percutaneous procedure, the remaining disc is no longer assembled as a water balloon; the annulus becomes more like a flat tire with minimal resiliency. In the erect position, compression forces are solely exerted upon the cartilaginous annulus alone. During bed rest, little if any water is re-absorbed by the annulus. With the passage of time, it is conceivable that the annulus will flatten out and the disc height will permanently decrease. As the vertebrae above and below the disc come closer together with less and less disc space, the growth of bone spurs and rim appear. The stenotic process has just begun. The pain returns. Unfortunately, unlike the previous irritation by the bulging disc, this time the sensation of pain comes from nerve compression by solid bones. Surgical procedures can be very involved, and the potential complications and scarring can be enormous.

In short, percutaneous nuclectomy may be a quick fix for decompressing a bulging or herniated disc without allergic reaction. However, within a not so distant future, there may be a much more complicated and painful ailment waiting.

Recently, several devices (U.S. Pat. No. 5,800,550 to Sertich, 1998; U.S. Pat. No. 5,683,394 to Rinner, 1997; U.S. Pat. No. 5,423,817 to Lin, 1995; U.S. Pat. No. 5,026,373 to Ray et. al., 1991) were designed to fortify the disc space between vertebrae. These types of devices are frequently referred to as spinal cages. Before inserting the device into the disc, the affected disc with portions of vertebral bone above and below the disc are cored out. Usually two holes are cored, one on each side of the disc, to insert two spinal cages. Donor bone or bone-growth promoting substances are packed into the porous cages. As the vertebrae heal from the coring, new bone grows into and permanently secures the porous cages. The purpose of using spinal cages is to replace the disc and keep the vertebrae apart. However, these vertebrae are permanently fused to each other, without resilient cushion, rotation or flexibility.

An improved version of a metallic spinal fusion implant (U.S. Pat. No. 5,782,832 to Larsen and Shikhman, 1998) tries to provide both rotational and cushioning capability. This invention resembles a disc prosthesis following a complete discectomy. Therefore, at least all the complications and postsurgical problems associated with a discectomy apply when this device is used.

(D) Tendon or Ligament Tear

In many accidents or sports related injuries, tendons or ligaments rupture from bones. Some very strong bone anchors (U.S. Pat. No. 5,851,219 to Goble et. al., 1998; and U.S. Pat. No. 5,478,353 to Yoon, 1995) have been invented and used with sutures to reattach ruptured tissues. Attached to a suture, the anchor is inserted into a pre-drilled bone hole. The suture usually comes with a needle for sewing and attaching the torn tissue back to bone. The manipulation of suture and attachment of tissue requires not only skill and time from the surgeon, it also requires operative space in the body of the patient. To obtain the space for suture manipulation, a sizable incision or multiple incisions are often required to complete a repair.

(E) Urinary or Fecal Incontinence

Urinary or fecal incontinence is far more common than expected. A recent finding from a large telephone survey of over 2500 households with nearly 7000 individuals reveals that for anal incontinence alone, 2.2% of the general population has the problem. Incontinent problems, urinary and fecal alike, can and usually do alter the lifestyles of the suffering individuals, resulting in (1) social withdrawal, (2) decreased exercise, (3) altered clothing choices, (4) minimized travel, (5) avoidance of sexual relationships and/or (6) spending over $2,000 per year for disposable or washable pads, laundry, medications and skin care products (Urology Times, February 1996).

One of the major causes of fecal incontinence in women is vaginal delivery of babies. In the United States, between 4% and 6% of women who have vaginal deliveries suffer from fecal incontinence. Fecal incontinence often coexists with urinary incontinence and may signify pudenda nerve damage. Many of these patients were found to have a weak anal sphincter, as evidenced by low anal squeeze pressures. Disruption of the anal sphincters has been attributed to episiotomies, perineal lacerations and forceps extractions.

There are several other common causes of fecal incontinence. With age, the internal anal sphincter thickens with fibrotic tissue and loses the viscoelastic properties, which are required for closure. Also, trauma can tear and permanently scar the sphincter, resulting in a continual leakage problem.

Open surgery is often performed to tighten the sphincter muscle with a suture or to replace the sphincter with an artificial elastic band. Like all other open surgeries, the incision is large; recovery is lengthy; and the medical cost is high. Furthermore, unlike most other surgical sites, which can recover undisturbed, fecal excretion is unavoidable. Sphincter repairs often encounter infection, hemorrhage, hematoma and/or other complications.

For stress urinary incontinence, there are more successful surgical procedures and effective devices to treat women than the ones used to treat men. For example, collagen, a paste-like formulation, is used to inject and bulk up the sphincter wall. Alleviating incontinence after one collagen treatment is rare for women, and it often requires five to six treatments to achieve a satisfactory level for men. Even for the individuals who endure the injections, collagen often tends to lose its bulk within a few months. Similarly, fat injections have been tried and are reabsorbed by the patient within months. Teflon-based non-absorbable materials were used, but the materials migrate away and lose their bulk and effectiveness (Urology Times, December 1997).

A disposable, inflatable urethral occlusive device has been designed for women (Urology Times, March 1995), and a penile clip for men (U.S. Pat. No. 4,942,886 to Timmons, 1990). These devices are very unnatural and uncomfortable.

For women, there are several common and effective surgical procedures for repairing intrinsic sphincter deficiencies. A vaginal sling provides an elastic support to the sphincter unit by compressing the vaginal wall (Urology Times, July 1994). However, this surgical procedure can alter the patient's sexual function. Bladder neck closure is infrequently performed and is irreversible. Potential complications of these surgical procedures include prolonged urinary retention, suprapubic pain, cellulitis, entrapment of genitofemoral or ilioinguinal nerve, vaginitis and/or suture infection (Glenn's Urologic Surgery, fifth edition, editor Sam Graham Jr., M.D., 1998).

(F) Carpal Tunnel Syndrome

Carpal tunnel syndrome is a painful and debilitating ailment of the hand and wrist widely believed to be caused by prolonged repetitive hand activities. Predisposing factors include congenital narrowing of the carpal tunnel, trauma to carpal bones, acute infection, endocrine imbalance, contraceptive medication or rheumatoid disease. The weakness, numbness, pain and clumsiness of carpal tunnel syndrome are mainly attributable to swelling or thickening of the tenosynovium and compression of the median nerve under the flexor retinaculum. Prolonged compression can lead to narrowing of the nerve with intraneural fibrosis, resulting in irreversible loss of function.

The conservative treatment using splintage to restrict hand and wrist activity is helpful for about 70% of the patients. With the restricted hand and wrist, many patients can no longer perform their jobs. Corticosteroid injections are often effectively used to reduce the inflammatory edema around the median nerve, but corticosteroids are not a long-term solution.

The most common surgical procedure for relieving compression of the median nerve is carpal tunnel decompression, which enlarges the carpal tunnel by severing the entire width of the flexor retinaculum. After the procedure, the hand is restricted for a month. Weakness and pain are felt for some time. Even with the surgical procedure, about 10% of the patients experience no improvement or even more pain (Carpal Tunnel Syndrome, Bruce Conolly, FRCS, 1984).

Carpal tunnel decompression is often associated with one or more surgical complications. Early postoperative complications include hematoma, edema and infection. Subsequent common complications are weakness of grip, stiffness of fingers, wrist and shoulder, adhesions of flexor tendons and/or pain from scar tissue entrapment of the cutaneous nerve (Hand Rehabilitation, 2nd Ed., Gaylord Clark, M.D, et. al.).

(G) Tumor and Blood Supply

Tumors, uncontrolled and rapidly growing tissues, demand extra nutrients by tapping adjacent arteries to feed and multiply the cancer cells. One of the most effective treatments of tumors is surgical removal. Often, the tumor is too large or too close to delicate tissues, such as nerves. To reduce the size of the tumor prior to surgical removal, radiation and chemotherapy are commonly used. However, both of these supporting techniques are invasive to the patients, who may face a long battle with cancer. As a less invasive approach, drugs are currently under investigation for reducing the new arterial growth feeding the tumor. These drugs are not likely to affect the existing arteries already feeding the tumor.

SUMMARY OF INVENTION

In keeping with the foregoing discussion, the present invention takes the form of a resilient fastener, which can be guided, delivered and deployed into tissue to provide a strong holding strength with sustained gripping forces. The fastener may be deployed using a fastener delivery device according to the methods described herein or by other devices and methods.

The fastener can reattach torn tissue, anchor a suture, fortify tissue, fasten protruded tissue, elastically close a sphincter, partially close a canal, permanently close a vessel or beneficially alter the shape of tissue.

Following the deployment of the first fastener, additional fasteners can also be deployed through the same puncture site providing additional strength, especially if different holding directions and positions are utilized. The additional fasteners may be deployed without completely withdrawing the delivery device from the puncture site.

The major components of the fastener delivery device are two tubes; one tube fits inside the bore of the other. For tissue penetration purposes, the outer tube can be sharpened at the distal opening and will be referred to as a needle. The main function of the inner tube is to hold the fasteners, and will be referred to as a cartridge. Both needle and cartridge have slits on the walls opened to their distal openings. As the needle and cartridge rotate against each other, the slits can line up, overlapping each other. When the slits overlap, they are in-phase. When the slits do not overlap each other, they are out-of-phase. For the cartridge, the slit is preferred to be opened length-wise from the distal opening all the way to or near the proximal opening.

The third component of the fastener delivery device is the fastener itself. The width of the fastener is no wider than the slits in the cartridge and in the needle. At least a portion of the fastener is made with a spring-like, flexible, resilient, elastic, super-elastic or shape memory material, and at least a portion of the fastener consists of tissue gripping elements. The fastener is made with curvature and gripping elements. Due to the spring-like or shape memory portion of the fastener, it can be elastically straightened either by mechanical constraint or temperature and is capable of resiliently curving back to or near the original shape when mechanical constraint is lifted or a transformation temperature is met. For simplicity, the resiliency of the fastener described in the text of this invention will concentrate on the mechanical constraint. However, it is understood that temperature may also be used.

The elastic fastener is or fasteners are loaded into the cartridge in the needle and resiliently straightened by at least the inner wall of the needle. In the out-of-phase mode, the most distal fastener near the distal opening of the cartridge is resiliently straightened only by the inner wall of the needle. The position of this fastener is called the deploy position, because the fastener is, in fact, ready for deployment. As the cartridge or needle rotates from the out-of phase to the in-phase mode, where the mechanical constraint is removed from the fastener in the deploy position, the resiliently straightened fastener resumes its original curved shape, protruding from the slits and gripping the surrounding tissue. Since the slits of both cartridge and needle are open distally, the deployed fastener is free to slide away from the delivery device when the fastener device is withdrawn from the tissue.

To prevent fastener migration with time, tissue ingrowth holes or grooves can be channeled into the fastener.

By indenting a portion of the slit opening of the needle, one can selectively deploy a portion of the fastener while the remaining portion of the fastener remains within the device. For example, the distal half of the slit is made slightly wider than the proximal half. When the needle and the cartridge slits are set nearly in-phase, or referred to hereinafter as semi-in-phase, the distal half of the fastener deploys into the surrounding tissue while the proximal half of the fastener remains within the device. A partially deployed fastener is called semi-deployed. The semi-deployed fastener is particularly helpful in endoscopic surgery. Using the gripping element on the deployed distal half, a surgeon is now capable of pulling, tightening and manipulating the tissue to be fastened for a superior and gap-free repair before fully deploying the entire fastener.

To prevent the semi-deployed fastener from slipping out during tissue manipulation, tapered fastener holding elements may be carved into or incorporated onto the inner wall of the needle. The holding elements provide anchoring for the portion of the fastener remaining in the needle. The tapering prevents jamming of the fastener during the transition between out-of-phase to in-phase.

Depending on the surgical needs, sometimes the proximal half of the fastener can provide better assistance in tissue manipulation than the distal half of the fastener. It is possible to open the slit in ways to allow the deployment of either the distal or the proximal portion of the fastener in the semi-in-phase mode. One side of the slit is indented at the distal half while the other side of the slit is indented at the proximal half. Depending on the direction of cartridge rotation, relative to the needle, the semi-in-phase mode can bring out either the distal or the proximal end of the fastener, with tapered fastener holding elements supporting both semi-deployments.

The outer needle may have penetration markers to indicate the depth of tissue penetration. Furthermore, the needle has one or more orientation lines. The line may run longitudinally from the slit through the length of the needle to indicate the deploy direction of the fastener, this orientation line is called the deploy line. In some surgical manipulations, the deploy line is mostly hidden by tissues. Another orientation line may also be marked longitudinally directly opposite the deploy line, perhaps in a different color, pattern or shade; and is called the back line. The back line indicates where the back of the fastener will face.

The fourth component of the invention is a handle attached to the needle. The needle handle is made strong enough to puncture soft bone and to rotate the needle. For surgical applications where both deploy line and back line are invisible by direct view or endoscope, the needle handle is fixed in a position relative to both lines to indicate the direction of fastener deployment.

The fifth component of the invention is a handle for the cartridge. The cartridge handle is attached to the cartridge and made sturdy enough to assist tissue puncturing, but the most important function is to rotate the cartridge inside the needle. Similarly, the cartridge handle is also fixed in a position relative to the slit of the cartridge to assist in establishing the direction of fastener deployment.

Multiple fasteners can be loaded into the cartridge. After the first fastener is deployed, a fastener advancing device pushes another fastener into the deploy position. For example, a simple plunger connected to a mechanical lever can be used to advance fasteners one after another into the deploy position.

To prevent accidental puncturing of the surgeon or unintended tissue of a patient by the sharp needle, a moveable sleeve may be extended to cover the needle. In addition to the protective purpose, the sleeve can also serve numerous functions to assist surgeries. After the needle is inserted into tissue, the sleeve can be used to push and position the punctured tissue into proper place for an optimal reattachment. To fasten a bulging or herniated disc, the sleeve may be used to push and hold in the bulging annulus during the deployment of fasteners.

The fastener delivery device utilizes the rotating cartridge, relative to the needle, to deploy fasteners into tissue through overlapping slits. Similar fasteners can be resiliently straightened in a needle without the cartridge, but with a plunger fitted inside the needle behind the fastener. After insertion of the needle into tissue, the plunger is held stationary while the needle is slowly retracted or withdrawn from tissue, thereby deploying the fastener out of the distal opening of the needle. In tissue, the fastener resumes the original resilient curvature and tightly fastens onto the tissue. Multiple fasteners can also be loaded into the needle and deployed one at a time into different locations.

The fasteners can be made with alloy, pure metal, polymer, ceramic or composites. The fasteners can also be formed from modular parts, coated with lubricants, drugs, growth factors, antibiotics, hydrophilic compounds, hydrophobic compounds, self-sealing materials, swellable components, plasma coating or other substances. The curvature of the fasteners can be made symmetrical, asymmetrical or with multiple curvatures. The fasteners or parts of the fasteners can be made with biodegradable materials or with permanent materials. The fasteners or parts of the fasteners can be attached with or attached to a suture or other fastening devices.

SUMMARY OF METHODS AND ADDITIONAL EMBODIMENTS

In preparation for use, the fastener delivery device is set in the out-of-phase mode with a fastener in the deploy position. The tissue needing to be fastened is chosen, prepared and arranged. The device is then guided to the proper depth and orientation by the penetration markers, orientation line(s), endoscope, X-ray, ultrasound, MRI and/or other technique.

(A) Meniscal Repair

Guided by an arthroscope and the penetration markers, the device punctures the meniscal body and traverses the tear. Through the indented slit of the needle, the distal half of the fastener with gripping element is deployed. The torn portion is gently pulled in and manipulated back to the main body of the meniscus, then the fastener is fully deployed by setting the cartridge fully in-phase to close the tear. The device is now ready to be withdrawn, or another fastener may be deployed through the same puncture site in a different direction to ensure a tight closure.

To deploy another fastener, the cartridge is reset from the in-phase back to the out-of-phase position. Another fastener is advanced in the cartridge chamber to the deploy position. The needle handle may then be used to rotate the device, for example, by 180° for the deployment of another fastener. If two fasteners in the puncture site are sufficient to hold the tear at the location, the device is ready to be withdrawn from the meniscus. To prevent accidental scraping of the delicate articular cartilage in the knee joint, the sleeve may be slid over the sharp needle before resetting the device to the out-of-phase position in preparation for deployment of an additional fastener or prior to withdrawal of the device.

For simplicity in the remaining method summary, operative procedures of the device, such as out-of-phase, in-phase, fastener advancement, sleeve sliding, device rotation, puncture or withdrawal will not be mentioned in great detail, unless the operation is greatly varied from that described above.

(B) Ligament Repair

To fortify the longitudinally oriented collagen fibers in a torn anterior cruciate ligament, ACL, some specially designed fasteners are deployed to grip and bundle the collagen fibers of the ACL together like a collar. Frequently, the ACL is stretched and irreversibly lengthened prior to breaking. Therefore, the collar may not always be placed near the end of the tear. The placement of the collar is determined after manipulating and fitting the torn ACL in the patient's leg to ensure appropriate length after reattachment.

A ligament holding device may also be included to hold the ACL stationary and to guide insertion of the fastener delivery device containing the collar fasteners.

For ACL tears close to the tibia or femur, a trocar is passed through the collar to the bone to establish an ACL reattachment position. A cannula is inserted as a sleeve over the trocar and contacts the bone. The trocar is then removed and replaced with a drill having drill stops to prevent excessive penetration into the bone. After drilling, the drill is removed and replaced with the fastener delivery device into the drilled hole through the cannula. Unlike the collar fasteners mentioned earlier, the gripping elements for the bone attachment are designed to resist vertical or longitudinal pull out. The length of the fasteners is sufficient to span the depth of the drilled hole to beyond the collar in the torn ACL. Prior to deployment of the fasteners, the cannula is lifted beyond the slit of the needle. The collagen fibers of the ACL are in contact with the delivery device, especially with the slit portion of the needle. The first fastener is then deployed. The gripping elements on one end of the fastener anchor onto the collar-fortified ACL fibers or may even latch onto the collar itself. The gripping elements on the other end of the fastener anchor into the hole in the bone. Due to the spring-like property built into the fastener body, the gripping elements at both ends are constantly compressing the tissues, in this case the ACL fibers and bone, making the fastening strength exceptionally strong. To ensure adequately strong reattachment, multiple fasteners, preferably deployed in different directions, can be loaded into the same drilled hole without lifting the fastener delivery device.

Often, the ACL is torn at or near its mid-section. A similar technique using the ligament holder and collar fasteners is used to install two sets of collars, one on each torn end of the ACL. The fastener delivery device is threaded through the collars. The fastener delivery device is loaded with fasteners similar to the ones used to attach the ACL to bone. With the indented slit on the needle, partial deployment of the first fastener is helpful to pull and manipulate the distal ACL fragment into place. Sliding the sleeve over the needle can also be used to push tissue, in this case the proximal ACL fragment, to tightly rejoin the distal ACL fragment. The fastener is then fully deployed, gripping both fragments of ACL fibers fortified by two sets of collars.

(C) Tendon Repair

The fastener delivery device of the present invention can be used through a small opening to reattach a tendon back to the bone without sewing, manipulating or tying sutures. Similar to reattaching the ACL to bone, a trocar is used to pierce and guide the tendon into the proper position, where a hole will be drilled in the bone. A cannula is inserted over the trocar, and then the trocar is replaced with a drill creating a hole in the bone. The drill is then replaced by the fastener device inserted through the tendon into the bottom of the bone hole. The cannula is lifted so that the slit opening of the device is in contact with tendon tissue. If necessary, the tendon can be pushed and positioned by the sliding sleeve. The fasteners in the device should have sufficient length to grip both the bone and the tendon tissue. With time, similar to the reattached ligament, the tendon can and most likely will permanently reattach back onto the bone.

For soft bone, such as the humeral head in the shoulder, the needle of the device could possibly pierce a tendon to be reattached and puncture into the humerus without using the trocar, cannula and drill. The sleeve of the device may be used to manipulate the tendon for a tight and permanent repair.

(D) Bulging or Herniated Disc Fastening and Repair

To fasten bulging or herniated discs, the spring-like fasteners mentioned in the invention are made extra long with multiple gripping elements. For the best result, the needle of the fastener delivery device punctures the bulging portion and is guided into the disc by anteroposterior and lateral fluoroscopy or other technique. In cases where the bulging portion of the disc is well concealed by the lamina of the vertebra, a small amount of the bone can be removed to allow penetration of the delivery device. When the appropriate depth is reached, the sliding sleeve is used to push and hold the bulging portion of the disc inward; the fastener is deployed to grip and compress the previously bulging tissue back in place. To make possible the push and hold technique using the sleeve during deployment of the fastener, the distal opening of the sleeve also contains a slit, which may be oriented to overlap the slit of the needle. As the device is set in the in-phase position, the slits of the cartridge, needle and sleeve are aligned, allowing the fastener to deploy and hold the compressed tissue in place. Similar to previously mentioned surgical procedures, more than one fastener can be deployed through the puncture site, preferably toward different directions, to enhance a permanent fastening. The spring-like fasteners with multiple gripping elements provide an exceptionally strong holding strength with constant fastening forces holding back the repaired annulus, away from nerves.

The fastener directly, actively and elastically holds the bulging or herniated tissue back without removing the nucleus pulposus. Therefore the bulging or herniated disc may be repaired without loss of nucleus pulposus.

Some surgeons may like to approach the disc repair anteriorly. After retracting the abdominal contents, the device can be guided, perhaps by fluoroscope or other means, through the disc to the bulging or herniated portion. As the tip of the device reaches or nears the bulging surface, the distal half of the fastener is deployed. The bulging portion of the disc is gripped and pulled inward, then the fastener is totally deployed to fasten the bulged disc.

To prevent possible leakage of the nucleus pulposus around the fastener, prior to device insertion into the disc, a sealing patch, made with elastic and biocompatible material with closure capability, is inserted on the needle against the distal opening of the sleeve. For best results, the sleeve is fixed proximally and stationary to provide a position where the proximal tip of the soon to be deployed fastener will grip the sealing patch. Using similar guiding, inserting and compressing techniques, the sealing patch is tightly compressed, adhered or maybe even embedded into the previously bulging or herniated annulus. As the fastener is deployed, it grips the patch to seal possible leakage of nucleus pulposus. The sealing patch is a preventive measure and is optional.

Other fastening devices can be used to fasten the bulging or herniated annulus. A simple screw with tissue holding threads can be inserted through a pre-punctured hole, to compress and hold the bulging or herniated disc away from the encroached nerve. The screw can be made with a locking device to prevent loosening and/or with threads having a variable pitch to compress bulging or herniated tissue. Depending on the severity of the bulge or herniation, a simple staple or tack with tissue holding elements may be sufficient to fasten the weak annulus.

Suturing can also be used to fasten bulging or herniated discs. For example, the midsection of a small dumbbell-shaped rod is tied to a suture. The rod with suture is fitted inside a needle. Behind the rod, a plunger is inserted into the needle. The needle is guided through the bulging or herniated disc. With the plunger, the rod is pushed out of the distal opening of the needle, outside the annulus. The rod is now caught by the outer surface of the annulus and acts as an anchoring device for the suture. The needle is removed. A washer is threaded with the suture, slipped down to the bulging disc, compressed and tied. For surgical convenience, the washer can be made in conjunction with a suture-locking device to eliminate suture tying. The suture may be made of natural or synthetic fibers, such as gut, polymers and metals.

For fastening bulging or herniated discs, other fastening devices, such as tacks, tissue anchors, staples or clamps, can also be used. To prevent possible leakage of nucleus pulposus, a sealing patch can be used in conjunction with any of the fastening devices mentioned.

(E) Urinary or Fecal Incontinence Repair

For urinary and fecal incontinence, the spring-like fasteners of the present invention can be guided into the body and deployed to grip and elastically close the leakage of the sphincters. For insertion of the fastener delivery device, numerous existing guiding techniques, such as cystoscope, ultrasound, anteroposterior-lateral fluoroscopy, MRI or others, can be used effectively and accurately to guide the insertion and deployment of the fasteners. Again, multiple fasteners can be used to ensure proper closure of the sphincter.

To provide instant feedback to the surgeon, a pressure sensing catheter balloon, strain gauge, or tightening detecting instrument can be inserted into the leaking portion of the rectum and/or urethra As the fastener deploys and tightens the leaking portion, the instrument can provide instant information to the surgeon regarding the placement and effectiveness of the deployed fastener. For fluoroscopic image enhancement, the catheter or instrument can be made or coated with radiopaque material to perfect the accuracy of the fastener delivery device insertion. For ultrasound image enhancement, echogenic enhancing material can be used.

Especially among elderly patients, the elasticity of sphincters varies greatly. Elasticity sensing balloons or instruments are particularly helpful in determining the elasticity of the sphincter tissues so that surgeon can select fasteners with appropriate closure strength and curvatures for optimum repairs.

(F) Carpal Tunnel Syndrome Relief

Utilizing the elastic curvature of the fastener and the pliable nature of the flexor retinaculum, the fastener delivery device is inserted into the flexor retinaculum, perpendicular to and over the median nerve. As the fastener is deployed toward the palm inside the retinaculum, the curvature of the fastener forms the shape of an arch, lifting the flexor tissue, which was compressing the median nerve. With several other fasteners deployed side by side, a tunnel is created to relieve median nerve compression without cutting the flexor retinaculum. The fasteners can even be made with biodegradable materials, which degrade with time after relieving the pain.

(G) Double Indented Needle Slit for Versatile Tissue Manipulation and Inter-locking Fasteners Adding to the versatility of the fastener delivery device, the slit can be double indented for semi-deploying either the proximal or distal portion of the fastener, depending on the direction of cartridge rotation. This feature is particularly helpful when alternating between fasteners to create interlocking tissue fastening. To enhance the double indented feature of the needle slit, the curvature of the fasteners can be made asymmetrical. For example, the first fastener in the deploy position is made with a curvature near the proximal end of the fastener. The following fastener in the cartridge is made with a curvature near the distal end of the fastener. After semi-deploying the proximal half of the first fastener, the tissue is tightened by pushing, then fully deploying the first fastener. The device is slightly withdrawn and reset to out-of-phase. The following fastener is advanced into the deploy position. The distal portion of the second fastener is semi-deployed into the tissue. For the second fastener, the tissue is tightened by pulling the device before full deployment. With tissue tightening by pushing and pulling, the fasteners interlock the tissue, through one needle puncture. In addition to pushing and pulling on the semi-deployed fasteners, twisting provides yet another dimension and benefit to the tissue manipulation and inter-locking fastening.

(H) Tumor Artery Closure

With an angiogram, the location of arteries supplying a tumor is mapped out. The fastener delivery device is inserted and guided to a tumor-feeding artery. With the needle slit facing the artery, the proximal portion of the fastener is deployed under the artery. The device may then be gently pushed to compress and restrict the artery. While pushing, the fastener is fully deployed to clamp and restrict the artery. If necessary, the device is slightly withdrawn, reset and another fastener is advanced from the cartridge. The second fastener is semi-distally deployed over the artery. The device may then be gently pulled to hook and further restrict the artery. While pulling, the second fastener is fully deployed to shut the blood flow. More fasteners can be deployed to ensure a complete closure of the artery feeding the tumor.

(I) Other Features, Purposes and Summary

The needle of the device may be curved with a flexible cartridge to accommodate rotation within the curved needle to reach under skin or around organs and tissue into a target site.

Many other surgical procedures can utilize the fastener and the delivery device. Some examples follow. The fastener and delivery device can endoscopically attach dislocated organs. For weight loss purposes, fasteners can be used to slow stomach emptying by restricting the pyloric sphincter or pyloric canal. The fasteners can also be used to attach medical devices inside the body.

The fastener and the delivery device can serve in numerous endoscopic procedures, which require connecting, reattaching, holding, fortifying, restricting, closing, compressing or decompressing tissues or other devices.

In brief summary, some of the possible benefits of the sustained gripping fasteners and the delivery device follow: (1) grip tissue continuously, (2) minimize fastener migration, (3) minimally invasive, (4) deploy multiple fasteners within a puncture site, (5) access deep body targets, (6) support and fortify fragile tissue, (7) reattach tissue without suture, (8) attach tissue to bone, (9) require minimal surgical space, (10) attach to other fastening devices, (11) versatile, (12) provide permanent and/or degradable fastening, (13) simple to use, (14) manipulate tissue, (15) restrict or close orifices or vessels, (16) compress or decompress tissue, and (17) provide directional fastening.

BRIEF DESCRIPTION OF THE DRAWINGS

FIG. 1 depicts a fastener with an elastic or spring-like curvature.

FIG. 2 depicts a similar fastener as the one in FIG. 1 being resiliently straightened by mechanical constraint (not shown) or by temperature.

FIG. 3 depicts an internal view of the fastener delivery device, where fasteners are resiliently straightened in the cartridge inside the needle. The needle slit and the cartridge slit are in the out-of-phase position.

FIG. 4 depicts an internal view of the fastener delivery device in the in-phase position, where both the needle slit and cartridge slit overlap or are aligned, allowing the deployment of the distal fastener.

FIG. 52 depicts an elastic closure of the anal sphincter, in this case with two spring-like fasteners.

FIG. 53A depicts a leaking sphincter due to incomplete closure.

FIG. 53B depicts the partial closure of the sphincter by a spring-like fastener.

FIG. 53C depicts the elastic closure of the sphincter by two spring-like fasteners.

FIG. 54 depicts possible entries for the fastener delivery devices for treating urinary and fecal incontinence. Tightening detecting instruments provide instant feedback to the surgeon after each fastener is deployed.

FIG. 55 depicts a hand with carpal tunnel syndrome and insertion of a fastener delivery device into the flexor retinaculum (not shown) under the skin.

FIG. 56 depicts several deployed fasteners lifting the flexor retinaculum, creating a tunnel to accommodate the irritated median nerve (not shown) beneath it.

FIG. 66 depicts modular gripping elements with stems fitting into the gripping element holes.

FIG. 67 depicts the assembled fastener with two modular gripping elements.

FIG. 68 depicts the sloped indentation of the needle slit with a deploy line indicating the direction of fastener deployment.

FIG. 69 depicts the slanted indentation of the needle slit for selecting initial protrusion of fastener deployment.

DETAILED DESCRIPTION OF THE EMBODIMENTS

Figure 5:
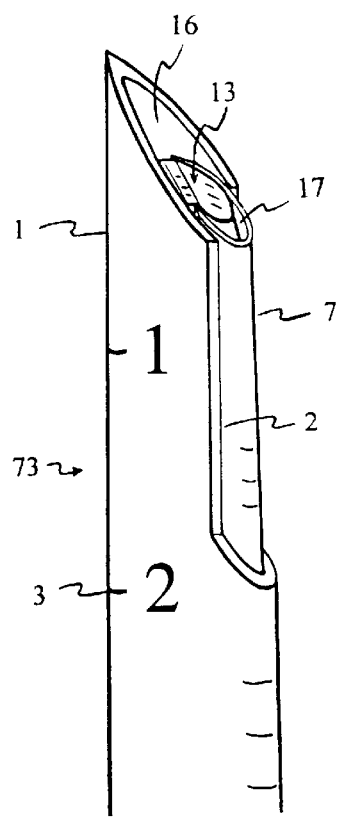
FIG. 5 depicts an external view of the fastener delivery device in the out-of-phase position.

In the present invention, a fastener can be guided, delivered and deployed into tissue to provide a strong holding strength with sustained gripping forces. The fastener can reattach torn tissue, anchor a suture, fortify a tissue, fasten protruded tissue, elastically close a sphincter, partially close a canal, permanently close a vessel or beneficially alter the shape of a tissue.

FIG. 1 depicts a fastener 13 formed of an elongated body being elastically predisposed toward a curvature. When the fastener 13 assumes the curvature, it it in the closed position. The ends of the fastener 13 are blunt, rounded, flat, etc., thereby decreasing the likelihood of the fastener 13 puncturing the surrounding tissue. A plurality of gripping elements 14 are formed on one side of the fastener 13, near each end. Further gripping elements 14 may be located on other sides to decrease the likelihood of migration of the fastener 13. All or a portion of the fastener 13 contains or is made of a spring-like or shape memory element 15, thereby predisposing the fastener 13 towards the curved configuration. If the shape memory element 15 is made with temperature sensitive material such as nickel titanium, transformation temperature is also very important.

FIG. 2 depicts a similar fastener 13 as the one in FIG. 1 being resiliently straightened by mechanical constraint, not shown, or by temperature acting on the shape memory element 15 of the fastener 13. The fastener 13 indicated is in an extended or open position.

The fastener 13 has a preferred range of lengths between 1.0 mm and 200 mm, more preferably between 3.0 mm and 70 mm. The fastener 13 has a preferred width of 0.1 mm to 30 mm, more preferably between 0.5 mm and 7.0 mm. Although not required, the fastener 13 is preferably configured such that the resilient member does not exceed the elastic limit of the material chosen. For example, a stainless steel resilient member's strain should not exceed approximately 2%. A nickel titanium resilient member's strain should not exceed 7–14%. The maximum strain varies depending on the alloy, heat treatment and coldworking. If a polymer is used the percent of strain varies significantly depending on the particular polymer chosen.

For the gripping elements 14 of the fasteners 13, the shape, direction, depth, pitch, angle, pattern, density, size and material can vary and certainly are important for effective tissue fastening. The gripping elements 14 may be grooves, as shown, or other shapes such as chevrons, bumps, etc. Some cases require strong gripping power, while other cases require a weak grip. The characteristics of the gripping elements may be adjusted to maintain the desired grip. The structure, size, shape, length, elasticity of the material and curvature of the spring-like or shape memory element 15 are also important factors in determining the intensity of the grips of the fastener 13.

The gripping elements 14 and the spring-like or shape memory element 15 of the fastener 13 can be made with one material or with multiple materials. The materials used in making the fastener 13 can be degradable, permanent or a combination of both. Due to the strength, superelastic and shape memory properties, nickel titanium is the preferred material for making at least a portion of the fasteners 13. For biodegradable properties, polylactic resin, polyglycolic resin, biomaterial or other polymers can be used. Other metals, alloys, polymers, ceramics or composites can also be used.

The fasteners 13 can be coated or blended with lubricants, tissue compatible components, antibiotics, growth factors, tissue sealing materials, hydrophilic or hydrophobic materials, drugs, drug releasing substances, swellable components, coatings, plasma coatings and/or others.

The fasteners 13 can also be formed in one piece or from modular parts, discussed with FIGS. 66, 67, 70 and 71. The parts can be coated with or contain lubricants, drugs, growth factors, antibiotics, hydrophilic compounds, hydrophobic compounds, self-sealing materials, swellable components, plasma coating or other substances.

The fastener 13 or parts of the fastener 13 can be made with biodegradable materials, such as polylactic resin, polyglycolic resin or other polymer. Biomaterials, such as collagen, elastin or others, can also be used as a biodegradable component in the fastener 13.

In addition to alloys or metals, numerous long lasting polymers can be used to make the fastener 13 or part of the fasteners 13. Polypropylene, polyethylene, polytetrafluoroethylene (PTFE) and many other polymers may meet the requirements.

As will be discussed in further detail later, the curvature of the fasteners 13 can be made symmetrical, asymmetrical or with multiple curvatures. The fasteners 13 or parts of the fasteners 13 can be attached with or attached to a suture 21 or other fastening devices.

Figure 6:
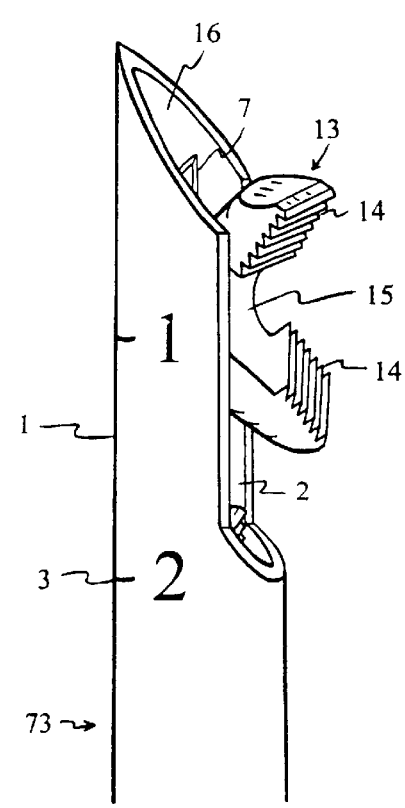
FIG. 6 depicts an external view of FIG. 5 in the in-phase position deploying a fastener.

FIG. 3 depicts an internal view of the fastener delivery device 73. FIG. 4 depicts an internal view of the fastener delivery device 73 in the in-phase position. FIG. 5 depicts an external view in the out-of-phase position. FIG. 6 depicts an external view in the in-phase position.

The major components of the fastener delivery device 73 are two tubes 1, 7; one tube fits inside the bore of the other. For tissue penetration purposes, the outer tube can be sharpened at the distal opening 16 and will be referred to as a needle 1. The main function of the inner tube is to hold the fasteners 13, and will be referred to as a cartridge 7. Both needle 1 and cartridge 7 have slits 2, 8 on the walls opened to their distal openings 16, 17. As the needle and cartridge 7 rotate against each other, the slits 2, 8 can line up, overlapping each other. When the slits 2, 8 overlap, they are in-phase. When the slits 2, 8 do not overlap each other, they are out-of-phase. For the cartridge 7, the slit 8 is preferred to be opened length-wise from the distal opening 17 all the way to or near the proximal opening.

The third component of the fastener delivery device 73 is the fastener 13 itself. The width of the fastener 13 is no wider than the slits 2, 8 in the needle 1 and in the cartridge 7. At least a portion of the fastener 13 is made with a spring-like, flexible, resilient, elastic, superelastic or shape memory material 15, and at least a portion of the fastener 13 consists of tissue gripping elements 14. The fastener 13 is made with curvature and gripping elements 14. Due to the spring-like or shape memory 15 portion of the fastener 13, it can be elastically straightened to the extended or open position either by mechanical constraint or temperature and is capable of resiliently returning to or near the original curved configuration or closed position when mechanical constraint is lifted or temperature is met. For simplicity, the resiliency of the fastener 13 described in the text of this invention will concentrate on the mechanical constraint. However, it is understood that temperature may also be used. The elastic fastener 13 is or fasteners 13 are loaded into the cartridge 7 in the needle 1 and resiliently straightened by at least the inner wall of the needle 1. In the out-of-phase mode, the most distal fastener 13 near the distal opening 17 of the cartridge 7 is resiliently straightened only by the inner wall of the needle 1. The position of this fastener 13 is called the deploy position, because the fastener 13 is in fact ready for deployment. As the cartridge 7 or needle 1 rotates from out-of-phase to the in-phase mode, where the mechanical constraint is removed from the fastener 13 in the deploy position, the resiliently straightened fastener 13 resumes its original curved shape, protruding from the slits 2, 8 and gripping the surrounding tissue. Since the slits 2, 8 of both needle 1 and cartridge 7 are open distally, the deployed fastener 13 is free to slide away from the delivery device 73 when the fastener delivery device 73 is withdrawn from the tissue.

The outer needle 1 has penetration markers 3 to indicate the depth of tissue penetration. Furthermore, the needle 1 has one or more orientation lines, seen in FIGS. 58 and 72. The orientation line may run longitudinally from the slit 2 through the length of the needle 1 to indicate the deploy direction of the fastener 13; this longitudinal line is called the deploy line 65. In some surgical manipulations, the deploy line 65 is mostly hidden by tissues. Another longitudinal line, the back line 66, perhaps in a different color, pattern or shade is also marked longitudinally directly opposite the deploy line 65. The back line 66 indicates where the back of the fastener 13 will face.

FIG. 3 shows the fasteners 13 resiliently straightened by mechanical restraint in the cartridge 7 inside the needle 1. The needle slit 2 and the cartridge slit 8 are in the out-of-phase mode with a fastener 13 in the deploy position and another fastener 13 below it. Under the constrained condition, both fasteners 13 are in open position.

FIG. 4 depicts an internal view of the fastener delivery device 73, where both the needle slit 2 and cartridge slit 8 are aligned or overlapped. Both slits 2 and 8 are open to distal openings 16, 17 of the needle 1 and cartridge 7. As the slits 2, 8 align or overlap each other, the mechanical restraint is relieved for the distal fastener 13. The fastener 13 resumes the curved shape by exhibiting a closed or clamped position and is elastically deployed from the slit 2 of the needle 1. In the clamped position, the gripping elements 14 are on the concave side of the closed fastener 13. But the proximal fastener 13 remaining in the fastener delivery device 73 is still resiliently restricted beneath the slit 2 of the needle 1.

FIG. 5 depicts an external view of the fastener delivery device 73 in the out-of-phase mode. The top portion of a fastener 13 in the deploy position is visible near the distal opening 17 of the cartridge 7. Penetration markers 3 are indicated on the needle 1.

FIG. 6 depicts an external view of FIG. 5 in the in-phase mode deploying a fastener 13. The fastener 13 resumes the resilient curvature and protrudes out the slit 2 of the needle 1.

In preparation for use, the fastener delivery device 73 is set in out-of-phase mode with a fastener 13 in the deploy position. The tissue needing to be fastened is chosen, prepared and arranged. The device 73 is then guided to the proper depth and orientation by the penetration markers 3, deploy line 65, back line 66, endoscope, X-ray, ultrasound, MRI and/or other technique.

Figure 7:
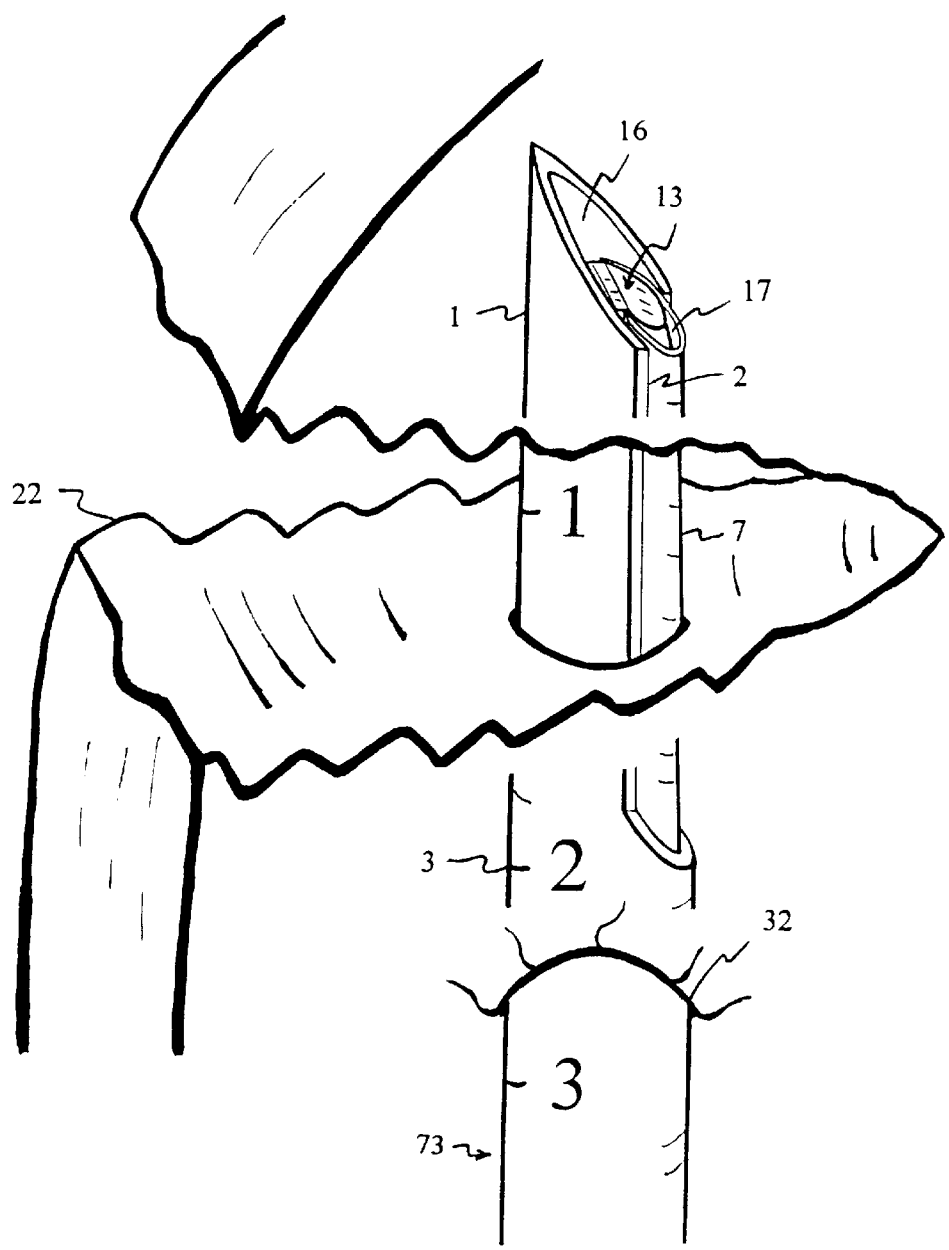
FIG. 7 depicts the fastener delivery device inserted into torn tissue.

FIG. 7 depicts the fastener delivery device 73 punctured 32 into a torn tissue 22. Guided by the penetration markers 3, endoscope or other viewing technique, the slit 2 of the needle 1 is positioned to bridge the tear. The direction of fastener deployment is easily controlled by simply turning the needle 1 of the device 73.

Figure 8:
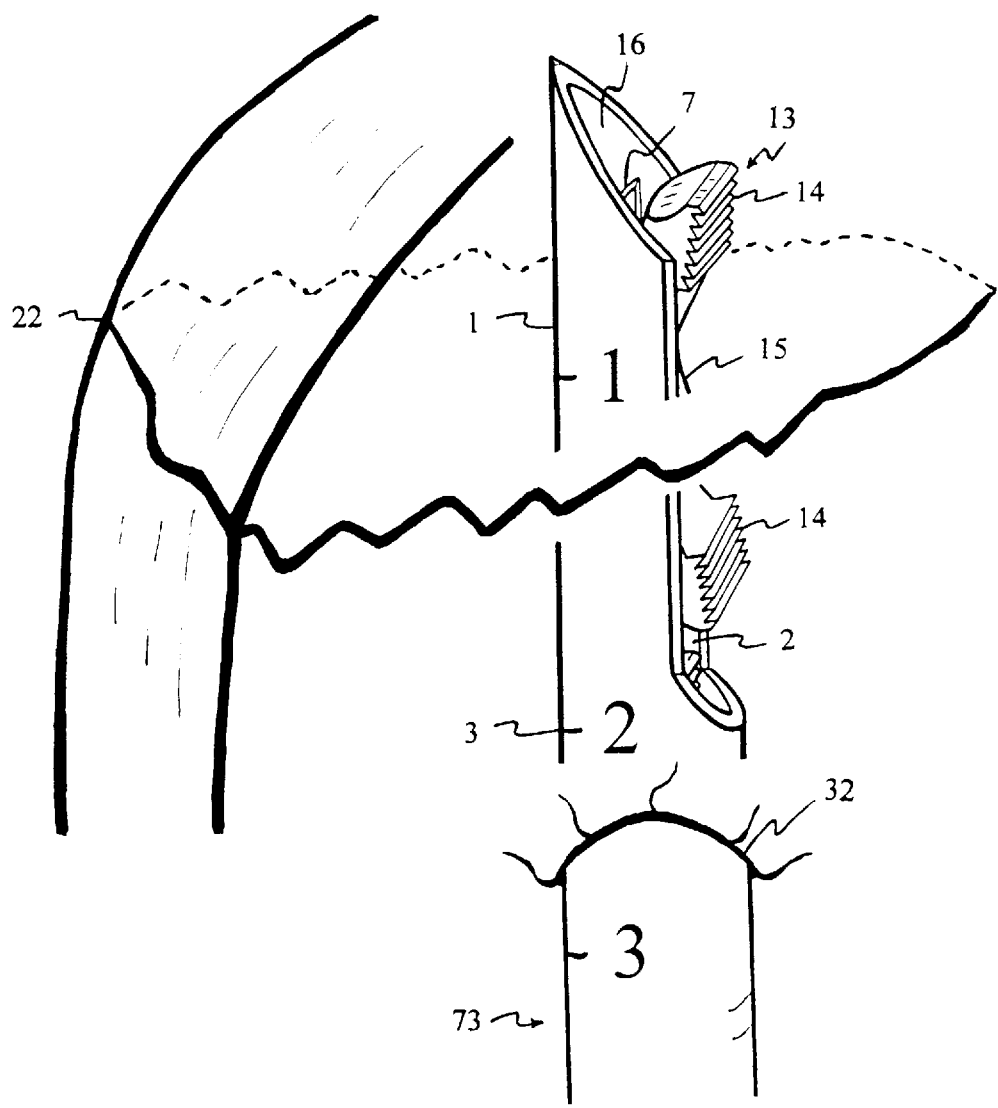
FIG. 8 depicts the deployment of the fastener into the tissue by setting the device from the out-of-phase to the in-phase position.

FIG. 8 depicts the deployment of the fastener 13 into tissue by setting the device 73 from out-of-phase to the in-phase mode. With gripping elements 14, the torn tissue 22 is being gripped; and the resumed curvature of the fastener 13 closes the torn tissue 22 gap. When the device 73 is withdrawn, the deployed tissue gripping fastener 13 can slide out from the device 73 along both the slit 2 of needle 1 and the slit 8 of cartridge 7 shown in FIG. 4 since both slits 2, 8 are open to the distal openings 16, 17 of needle 1 and of cartridge 7, also shown in FIG. 4.

Figure 9:
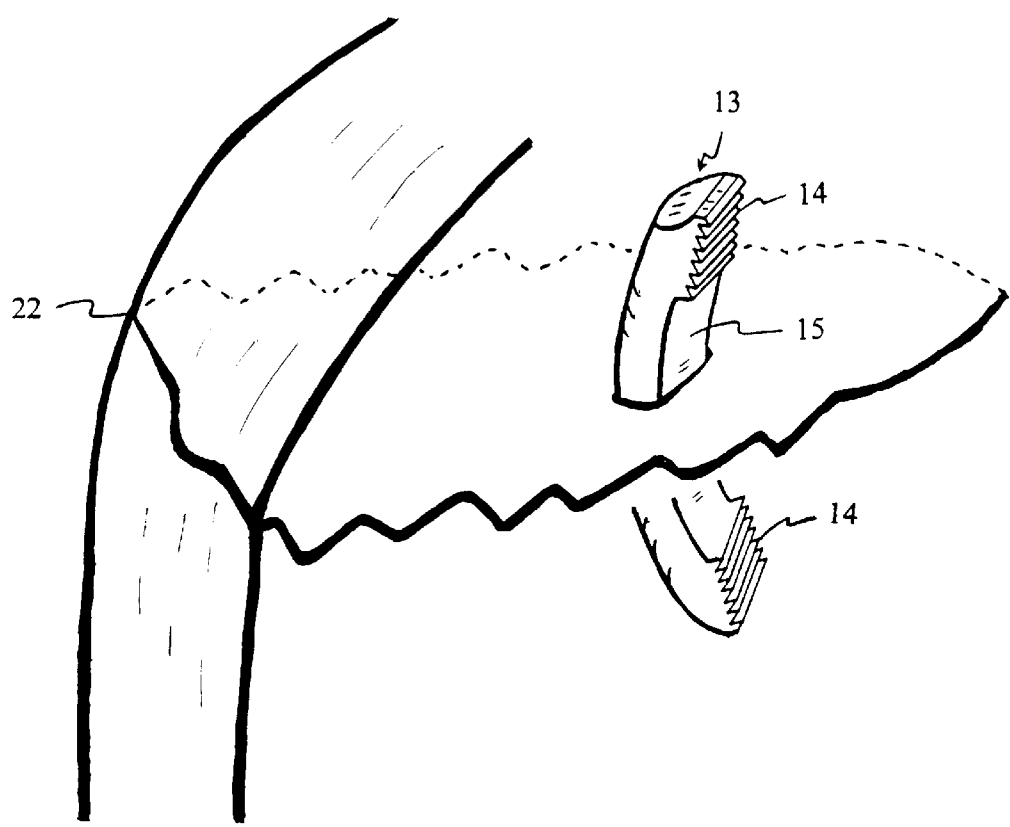
FIG. 9 depicts the tissue after the device has been withdrawn, the deployed fastener continues to elastically grip the torn tissue and closes the tissue gap.

FIG. 9 depicts the tissue after the device 73 has been withdrawn, the deployed fastener 13 continues to elastically grip torn tissue 22 and closes the tissue gap. The depicted curvature of the fastener 13 is between the resiliently straightened curvature in FIG. 2 and the full curvature depicted in FIG. 1 to indicate that torn tissue 22 is under sustained closure forces exerted by the fastener 13.

Following the deployment of the first fastener 13, additional fasteners 13 can also be deployed through the same puncture site 32 providing additional strength, especially if different holding directions and positions are utilized. The additional fasteners 13 may be deployed without completely withdrawing the delivery device 73 from the puncture site 32.

Figure 10:
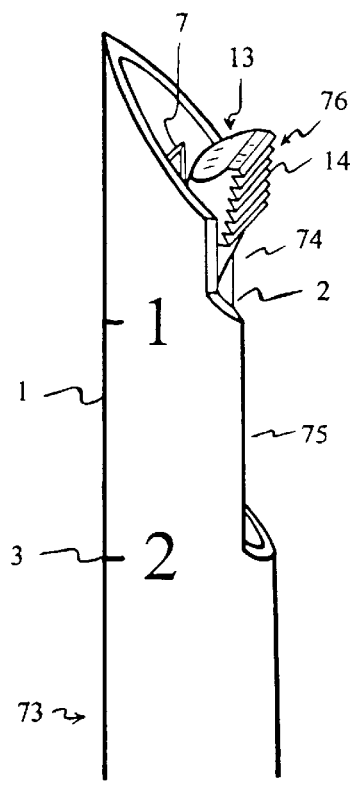
FIG. 10 depicts a distally semi-deployed fastener from an indented needle slit.

FIG. 10 depicts an example of an indented needle slit 2, where the distal portion 74 of the needle slit 2 is wider than the proximal portion 75 of the needle slit 2. By indenting the slit 2 of the needle 1, one can selectively deploy a portion of the fastener 13 while the remaining portion of the fastener 13 remains straightened within the needle 1 of the device 73. When the needle slit 2 and the cartridge slit 8 are set nearly in-phase, or called semi-in-phase, the distal half 76 of the fastener 13 deploys into the surrounding tissue while the proximal half 77 of the fastener 13 remains within the device 73. The half-deployed fastener 13 is particularly helpful in endoscopic surgery. Using the gripping elements 14 on the deployed distal half 76, a surgeon is now capable of pulling, tightening and manipulating the tissue to be fastened for a superior and gap-free repair before fully deploying the entire fastener 13.

Figure 11:
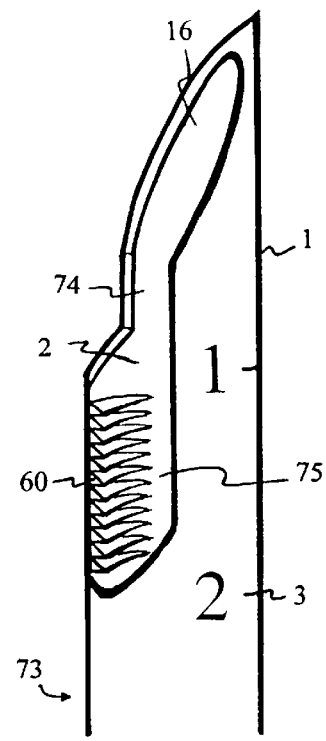
FIG. 11 depicts an inside view of the indented needle slit with tapered fastener holding elements.

To prevent the half-deployed fastener 13 from slipping out during tissue manipulation, fastener holding elements 60 may be carved as grooves into or incorporated onto the inner wall of the needle 1, as shown in FIG. 11 which depicts the inside view of the indented needle slit 2 with the fastener holding elements 60. The holding elements 60 may be tapered from very shallow ridges to taller ridges as they near the needle slit 2. The fastener holding elements 60 in this example are designed to hold the proximal portion 77 of the semi-deployed fastener 13 during pulling and tissue manipulation by surgeons. The fastener holding elements 60 are tapered to minimize fastener 13 jamming during rotation from out-of-phase to the semi-in-phase mode.

In an alternate embodiment, the entire fastener 13 may be deployed through the distal opening 16 of the needle 1 by removing the needle while holding a plunger within the needle 1 stationary. This embodiment may still be used to manipulate the tissue after the distal end of the fastener 13 has been deployed, but before the proximal end of the fastener 13 is deployed. The proximal portion of the fastener 13 could be deployed by removal of the needle allowing the entire fastener 13 to exit through the distal opening 16, or the proximal portion of the fastener 13 could deploy through the slit 2 of the needle 1. In this embodiment, the slit 2 could be shortened or omitted since none or only a small portion of the fastener 13 need exit the side of the needle 1.

Other embodiments may have the edge of the slit 2 in the needle angled or tapered to gradually bring the fastener 13 towards its deployed configuration prior to full deployment or the edge may have a straight edge, i.e. cut generally perpendicular to the perimeter of the needle 1.

Figure 12:
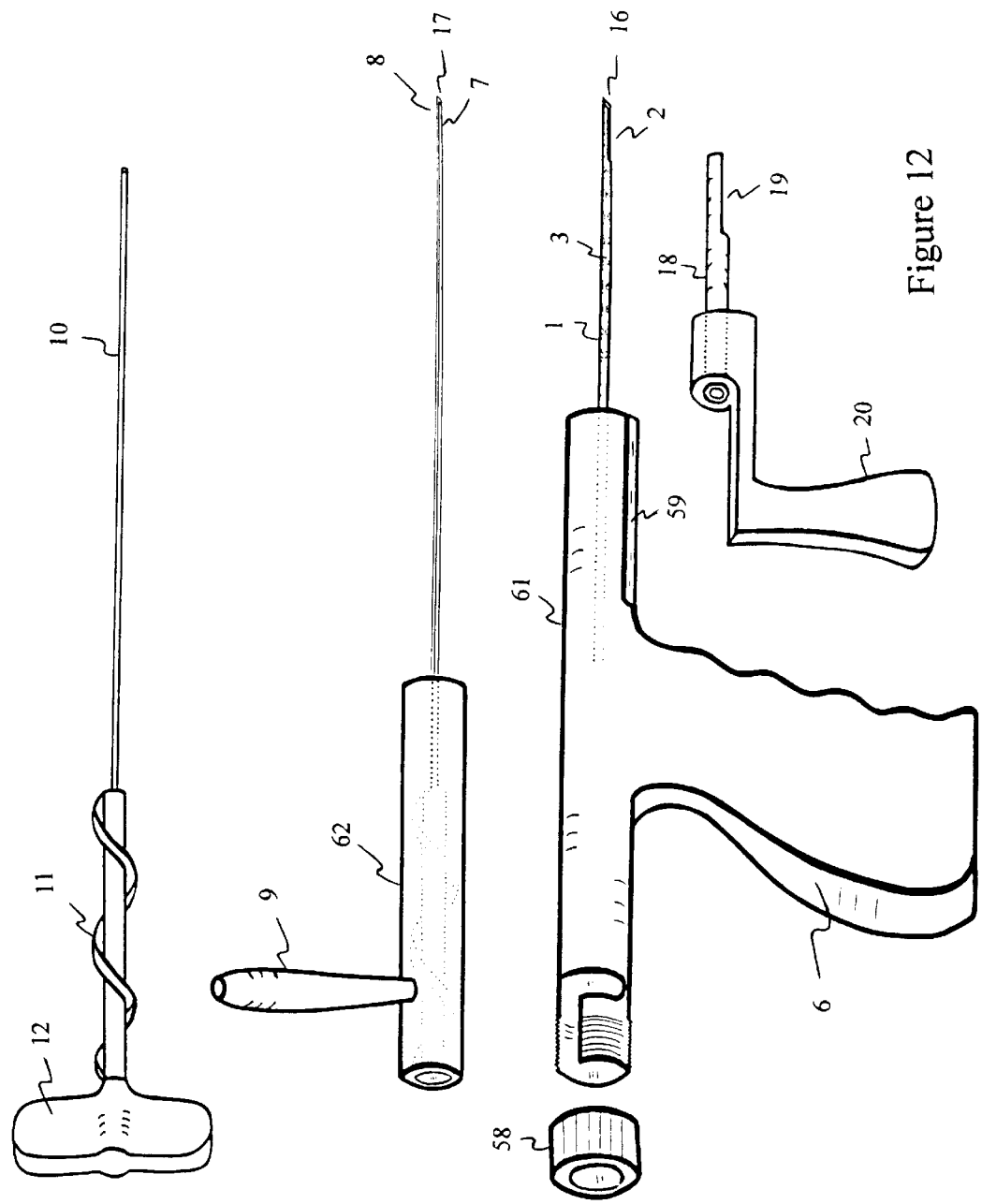
FIG. 12 depicts the parts of a functional fastener delivery device.

FIG. 12 depicts an example of a functional fastener delivery device 73 with individual parts. The device assembly follows. The sleeve 18 fits over the needle 1. To keep both sleeve slit 19 and needle slit 2 aligned or overlapping, a sleeve handle 20 is inserted into a sleeve-sliding track 59 to prevent the sleeve 18 from rotating. The proximal opening of the needle 1 is in the needle body 61. The cartridge 7 extending from the cartridge body 62 is inserted through the proximal opening of the needle 1. The cartridge body 62 is housed in the needle body 61. The cartridge 7 and the cartridge body 62 are operated by a cartridge handle 9, which extends through the side of needle body 61. The cartridge units are retained by a cartridge cap 58. For advancing fasteners 13, not shown, in the cartridge, a fastener-advancing plunger 10 is inserted through a hole of the cartridge cap 58 and the cartridge body 62 into the proximal opening of the cartridge 7. The fastener-advancing device 11 works in conjunction with the cartridge body 62 to advance fasteners. At the proximal end, a fastener-advancing handle 12 is used to drive the advancing units, pushing the fastener toward the deploy position. In the out-of-phase position, fasteners 13, not shown, can then be loaded, one by one, through the distal openings 16, 17 of the needle 1 and the cartridge 7.

The needle handle 6 is made strong enough to puncture soft bone and to rotate the needle 1. For surgical applications where both deploy line 65 and back line 66 are invisible by direct view or endoscope, the needle handle 6 is fixed in a position relative to both lines 65, 66 to indicate the direction of fastener 13 deployment.

The cartridge handle 9 is made sturdy enough to assist tissue puncturing, but the most important function is to rotate the cartridge 7 inside the needle 1. Similarly, the cartridge handle 9 is also fixed in a position relative to the slit 8 of the cartridge 7 to assist in establishing the direction of fastener 13 deployment.

Multiple fasteners 13 can be loaded into the cartridge 7. After the first fastener 13 is deployed, a fastener advancing device 11 pushes another fastener 13 into the deploy position.

For example, a simple plunger 10 connected to a mechanical lever acting as a handle 12 can be used to advance fasteners 13 one after another into the deploy position.

To prevent accidental puncturing of the surgeon or unintended tissue of a patient by the sharp needle 1, a moveable sleeve 18 may be extended to cover the needle 1. In addition to the protective purpose, the sleeve 18 can also serve numerous functions to assist surgeries. After the needle 1 is inserted into tissue, the sleeve 18 can be used to push and position the punctured tissue into proper place for an optimal reattachment. To fasten a bulging or herniated disc 41, the sleeve 18 can be used to push and hold in the bulging annulus during the deployment of fasteners 13. Skilled surgeons may also prefer to add rotational movements using tissue manipulating elements at the distal end of the sleeve 18.

(A) Meniscal Repair

Within the body, there are a number of menisci, typically near circular or crescent-shaped fibrocartilage or dense fibrous tissue structures which appear between bones. For the example given herein, meniscus will refer to a meniscus within the knee, however, the technique may be used on other menisci and other similar structures.

For meniscal repair, the device 73 is effective for both outside-in and inside-out approaches. The outside-in approach is to enter from the thick peripheral rim of the meniscus 26 toward the thin tapering portion of the meniscus 26. The inside-out approach is to enter from the thin portion toward the thick rim. The inside-out approach is more frequently used by surgeons using suture or meniscal tacks because it is less likely to rupture vessels and nerves. The fasteners 13 and delivery device 73 in the invention can accommodate both approaches. However, the drawings and method summary are depicted using the inside-out approach only.

Figure 13:
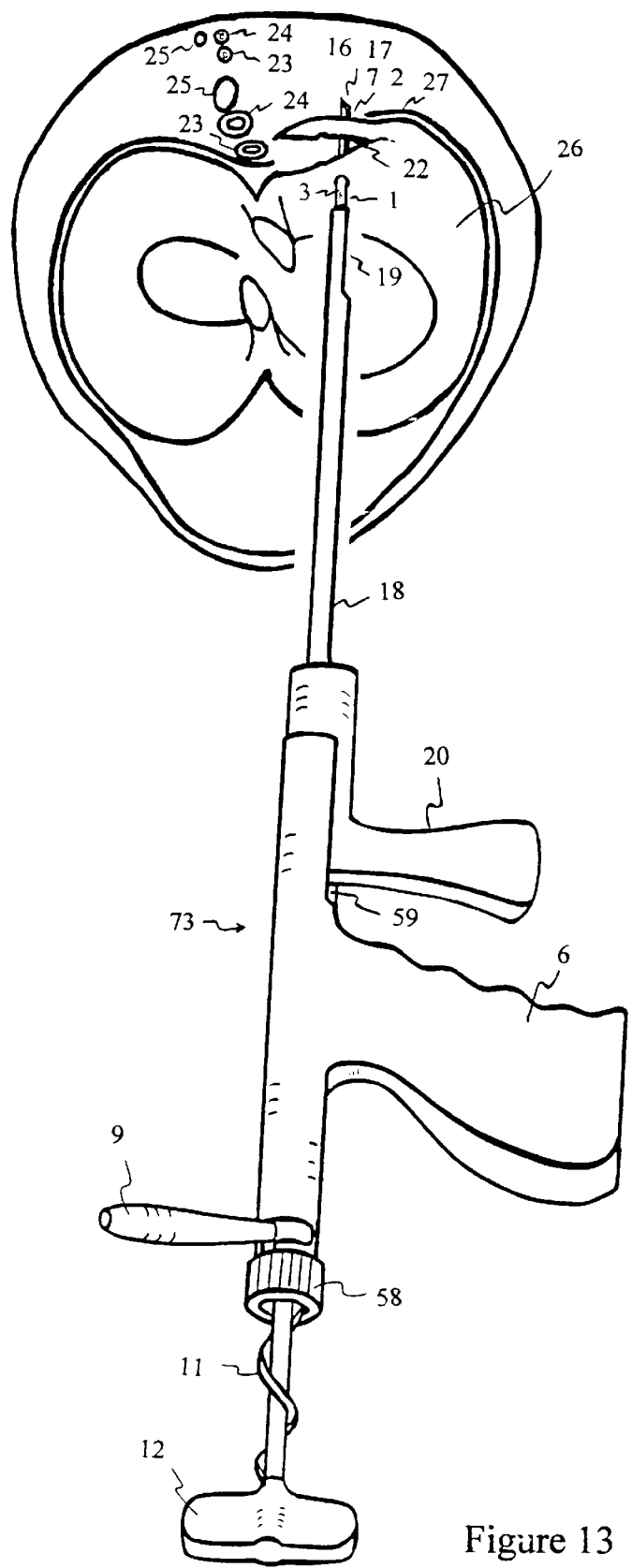
FIG. 13 depicts a fully assembled fastener delivery device set in the out-of-phase position. The needle punctures the torn meniscus and the needle slit is positioned within the plane of the meniscus to bridge the torn tissue.
Figure 14:
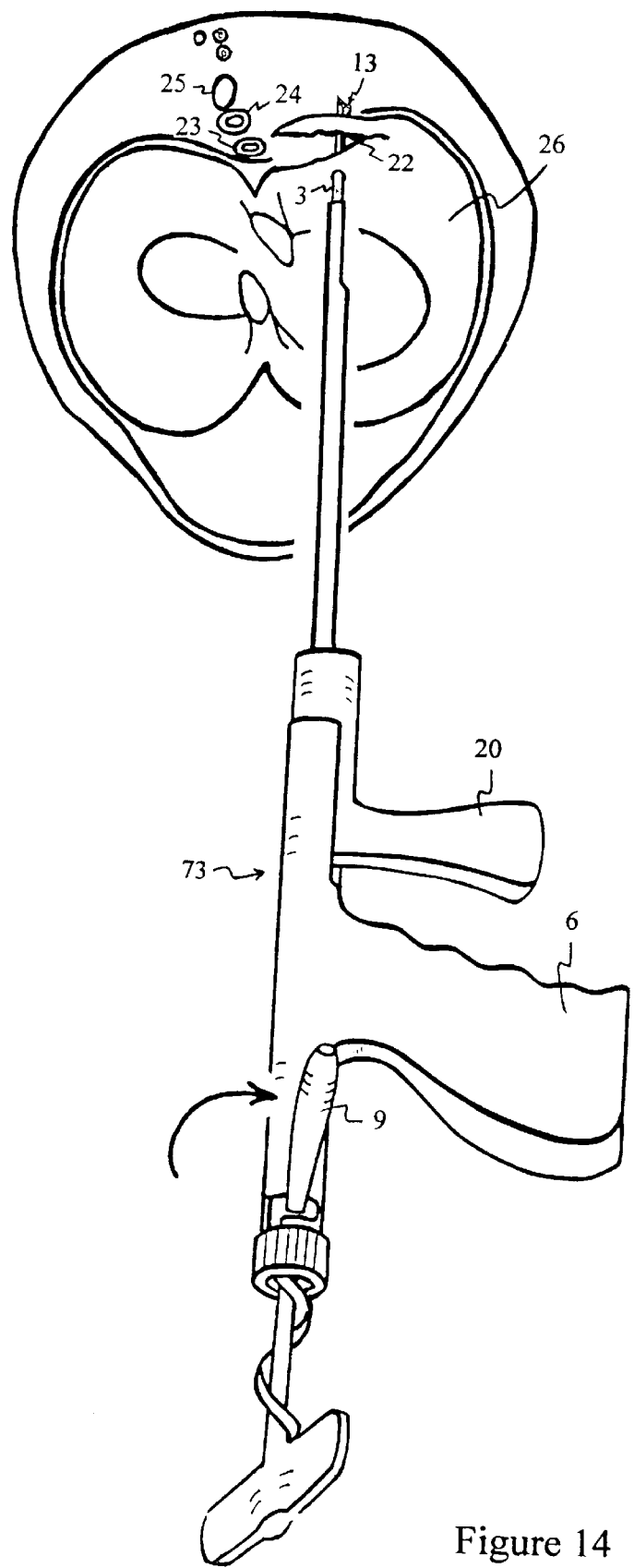
FIG. 14 shows the cartridge handle turned to the semi-in-phase position to deploy the distal portion of a fastener, as indicated in FIG. 10, to grip the torn tissue.

FIG. 13 depicts a very common meniscal tear 22 near nerves 25, arteries 23 and veins 24 in the knee of a patient. If the repair is done with suture, skin and muscle would be opened and the nerves 25, arteries 23 and veins 24 would all be retracted to prevent possible damage during suture passage and manipulation. For fastener 13 repair, nothing passes through the delicate area; therefore, opening the skin and muscle of the patient to retract the nerve 25 and blood vessels is not necessary. A fully assembled fastener delivery device 73 is set in the out-of-phase mode. Guided by an arthroscope, not shown, and penetration markers 3, the needle 1 punctures the torn meniscus 26 and the needle slit 2 is positioned within the plane of the meniscus to bridge the torn tissue 22. Through the indented slit 2 of the needle 1, the distal half 76 of the fastener 13 with gripping element(s) 14 is deployed as indicated in FIG. 14.

Figure 15:
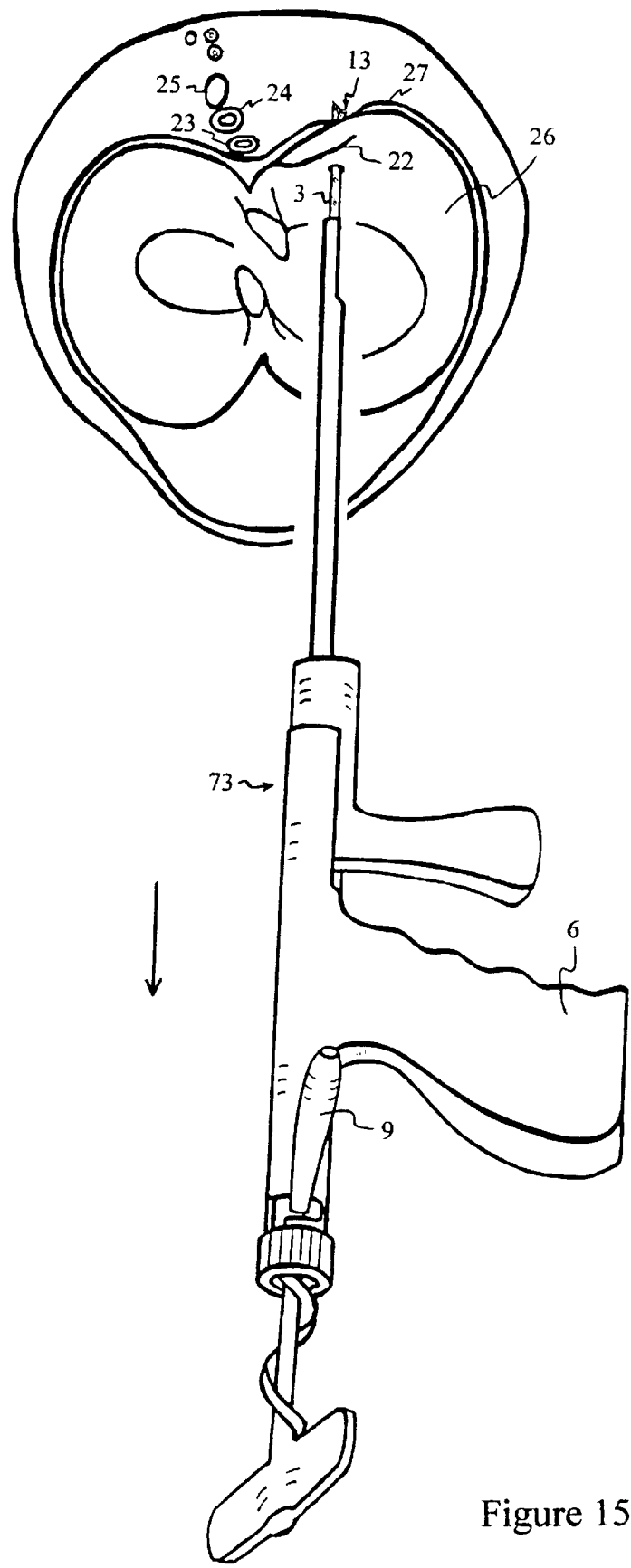
FIG. 15 shows the torn tissue gently pulled in to tighten the torn gap with the gripping of the distally semi-deployed fastener.

FIG. 15 shows the torn tissue 22 gently pulled in to tighten the torn gap with the gripping elements 14 of the distally semi-deployed fastener 13; in this case, it also grips the capsule 27.

Figure 16:
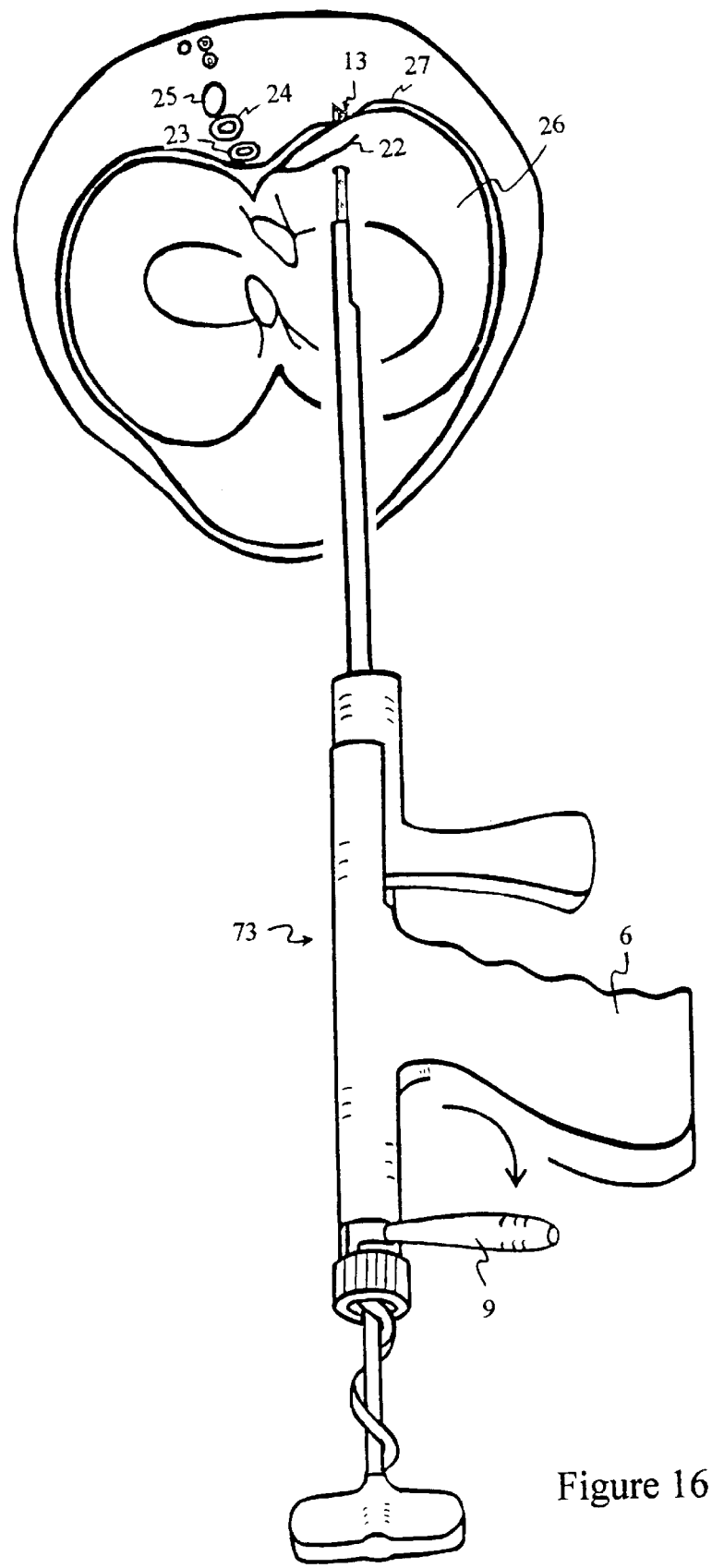
FIG. 16 shows the cartridge handle turned all the way to the in-phase mode to fully deploy the fastener holding the torn tissue in place.

FIG. 16 depicts the cartridge handle 9 turned all the way to the in-phase mode to fully deploy the fastener 13 holding the torn tissue 22 in place. The device is ready to be withdrawn, allowing the deployed fastener 13 to slide out of the distal openings 16, 17 of the needle 1 and the cartridge 7 indicated in FIG. 4.

For the highest holding strength, the tear 22 should be at or near the mid-portion of the fastener 13. The direction of fastener 13 deployment is preferably within the plane of the meniscus 26. The device 73 is now ready to be withdrawn, or another fastener 13 may be deployed through the same puncture site in a different direction to ensure a tight closure.

Figure 17:
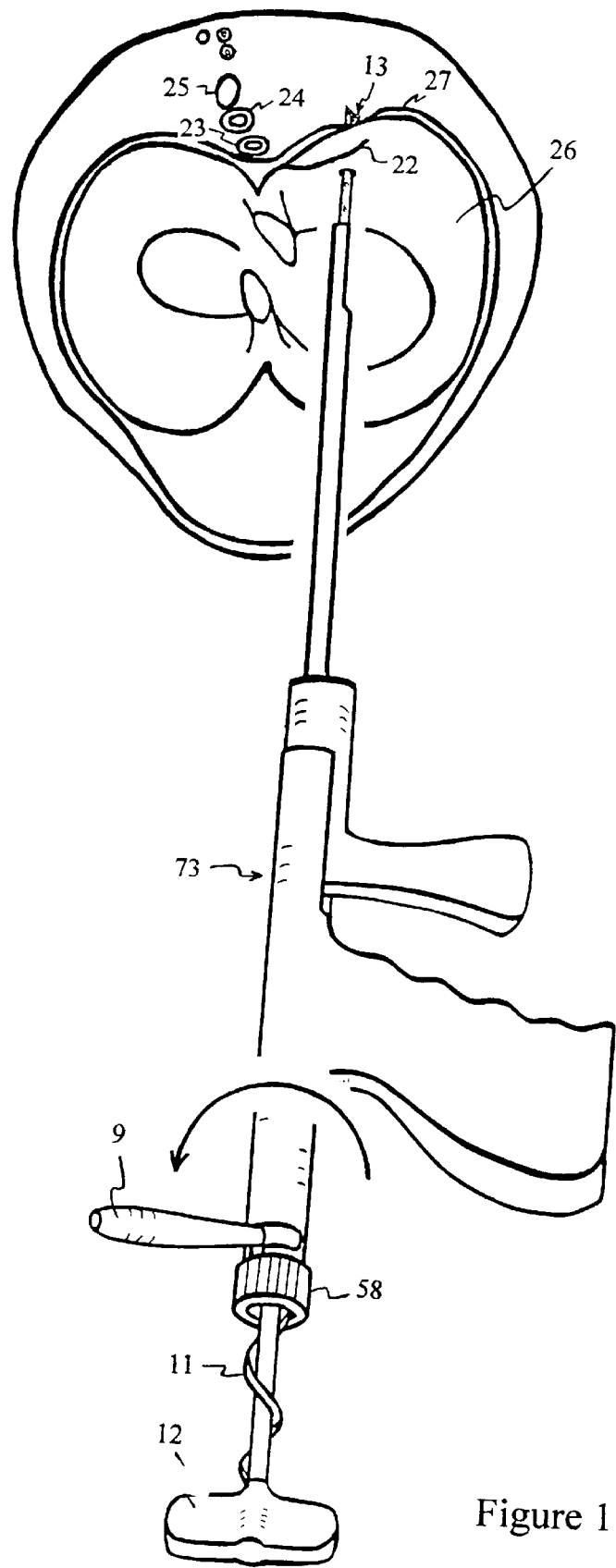
FIG. 17 shows the device reset to the out-of-phase mode by turning the cartridge handle backward.

To deploy another fastener 13 into the puncture site, the cartridge 7 is reset from in-phase back to out-of-phase mode as indicated in FIG. 17. However, it is possible that a portion of the deployed fastener 13 may remain in the cartridge 7 and restrict the cartridge 7 from rotating back to the out-of-phase mode. To free the cartridge 7 from the deployed fastener 13, the device may have to be slightly withdrawn from the puncture site 32 to depart or be free from the deployed fastener 13 prior to rotating.

Figure 18:
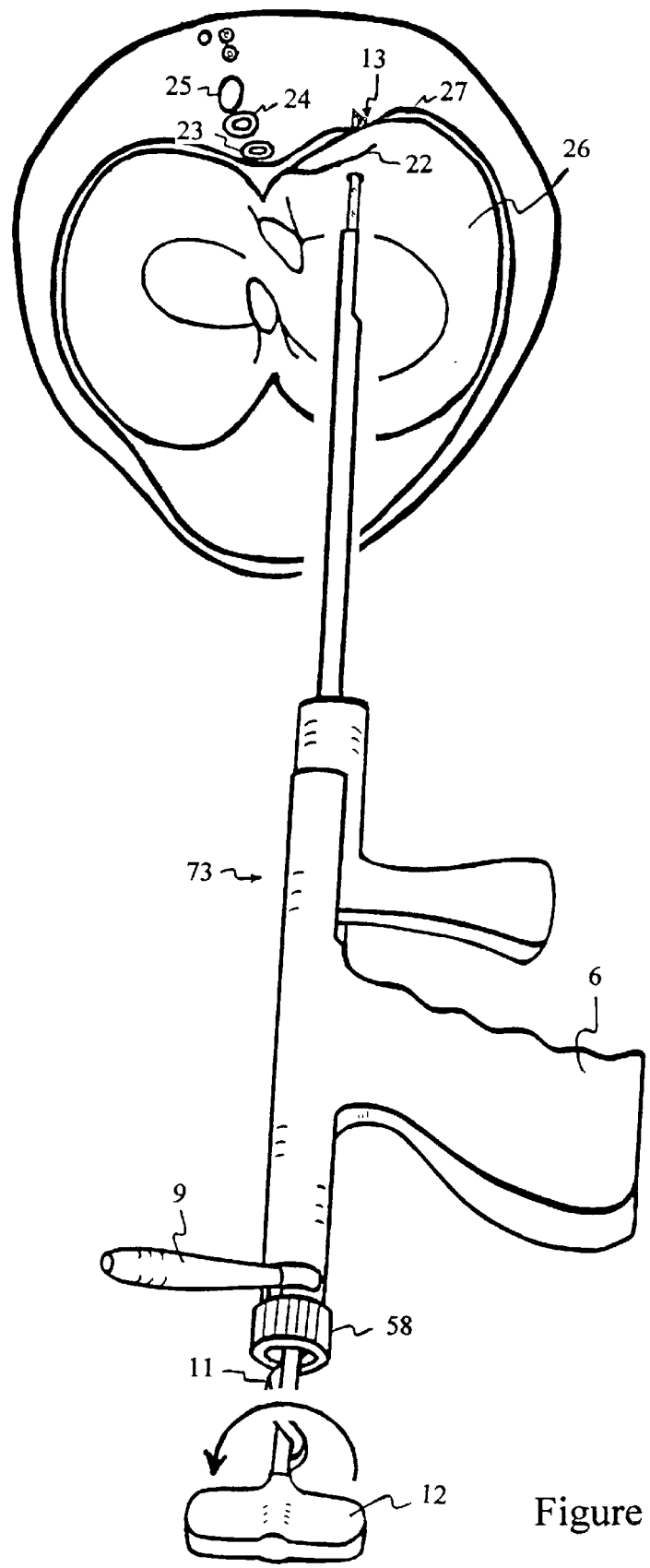
FIG. 18 shows the device with a fastener-advancing handle turned to place another fastener in the cartridge into the deploy position.

FIG. 18 shows the device 73 with the fastener-advancing handle 12 turned to position another fastener 13 in the cartridge 7 into the deploy position. The fastener-advancing device 11, not shown in this figure, is preferred to provide advancement of one fastener length for each semi-rotation of the fastener-advancing handle 12. Other mechanical designs for advancing fasteners 13 are possible.

Figure 19:
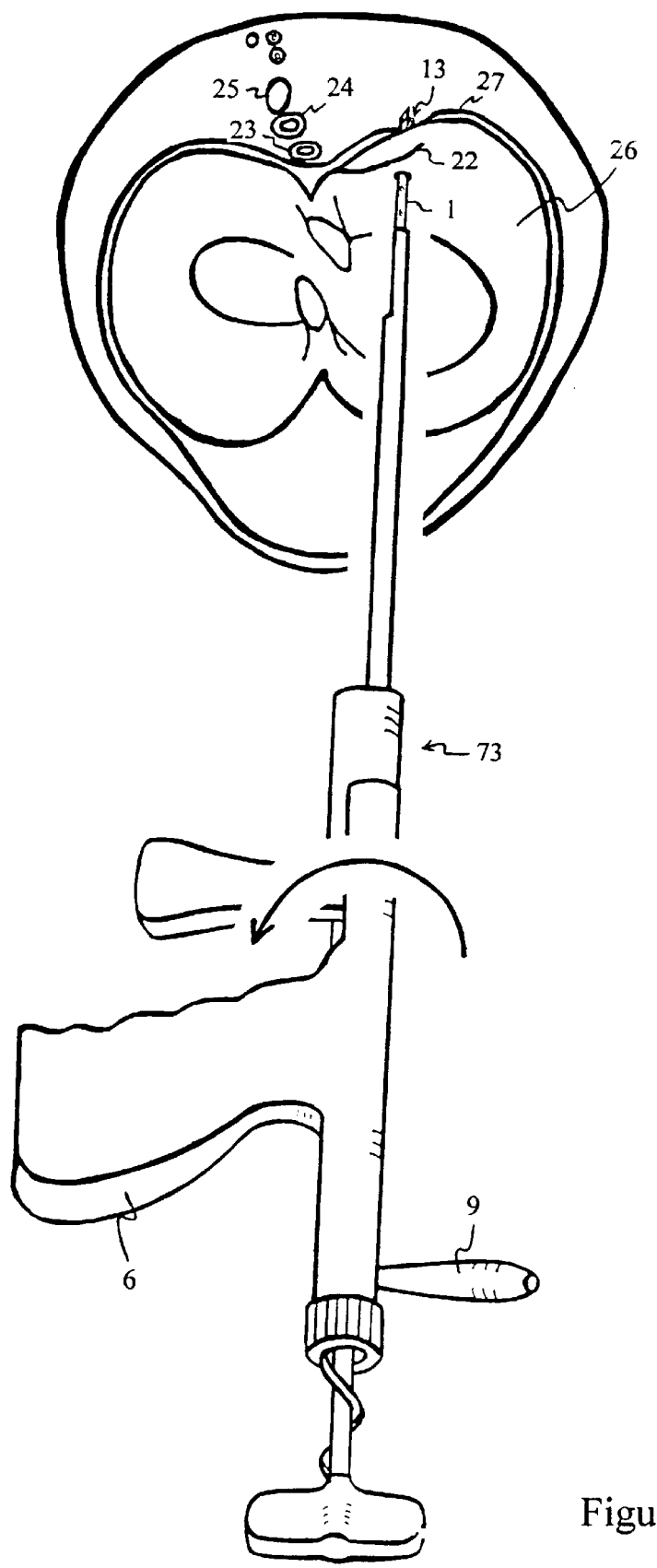
FIG. 19 shows the delivery device turned to vary the direction of the next fastener deployment with the needle remaining in the puncture site.
Figure 20:
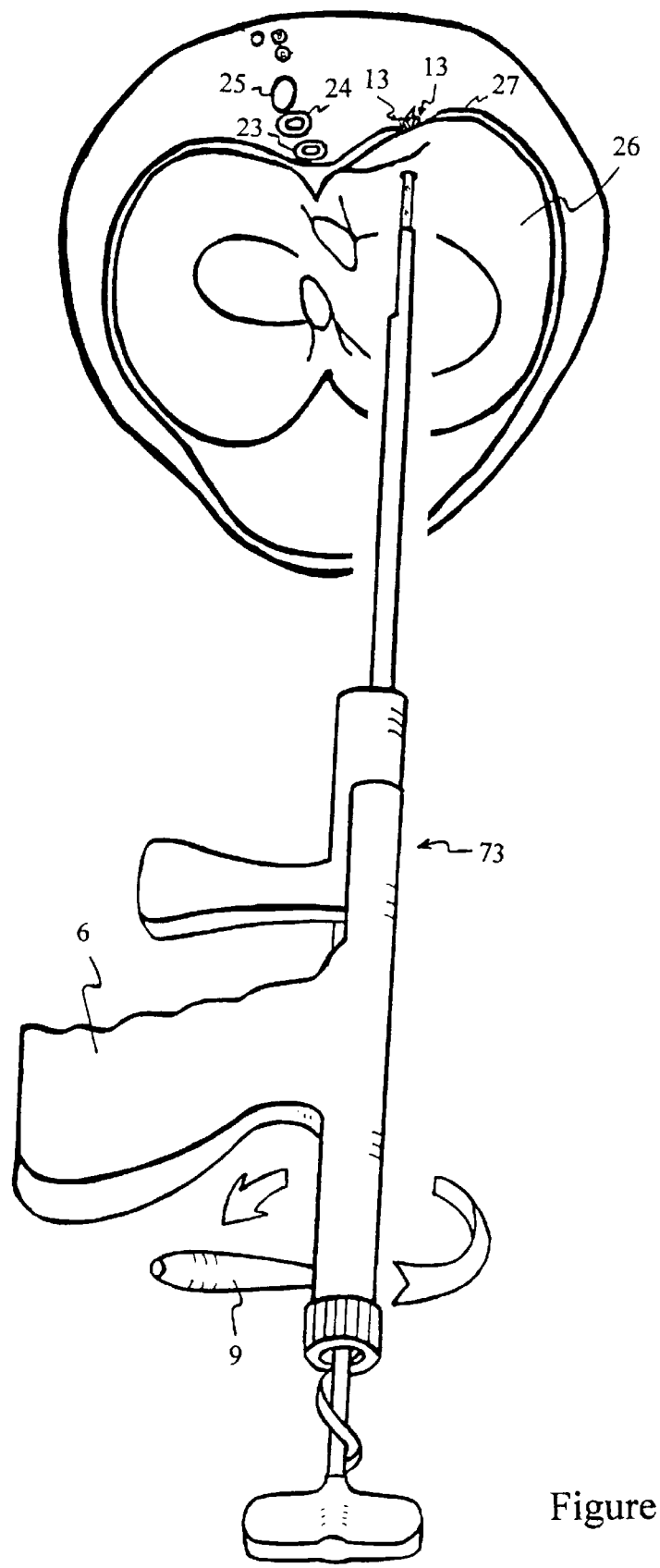
FIG. 20 shows the cartridge handle turned to deploy the next fastener to further secure the torn tissue.

The needle handle 6 may then be used to rotate the device 73, for example, by 180° as shown in FIG. 19. Presumably the first fastener 13 has already closed the tear 22, so tissue manipulation by the half-deployed fastener 13 technique is probably unnecessary. The second fastener 13 may, therefore, be fully deployed as shown in FIG. 20 to further secure the torn tissue 22. In this case, two fasteners 13 are deployed within the plane of the meniscus and with the deployment directions 180° from each other, within the puncture site.

Figure 21:
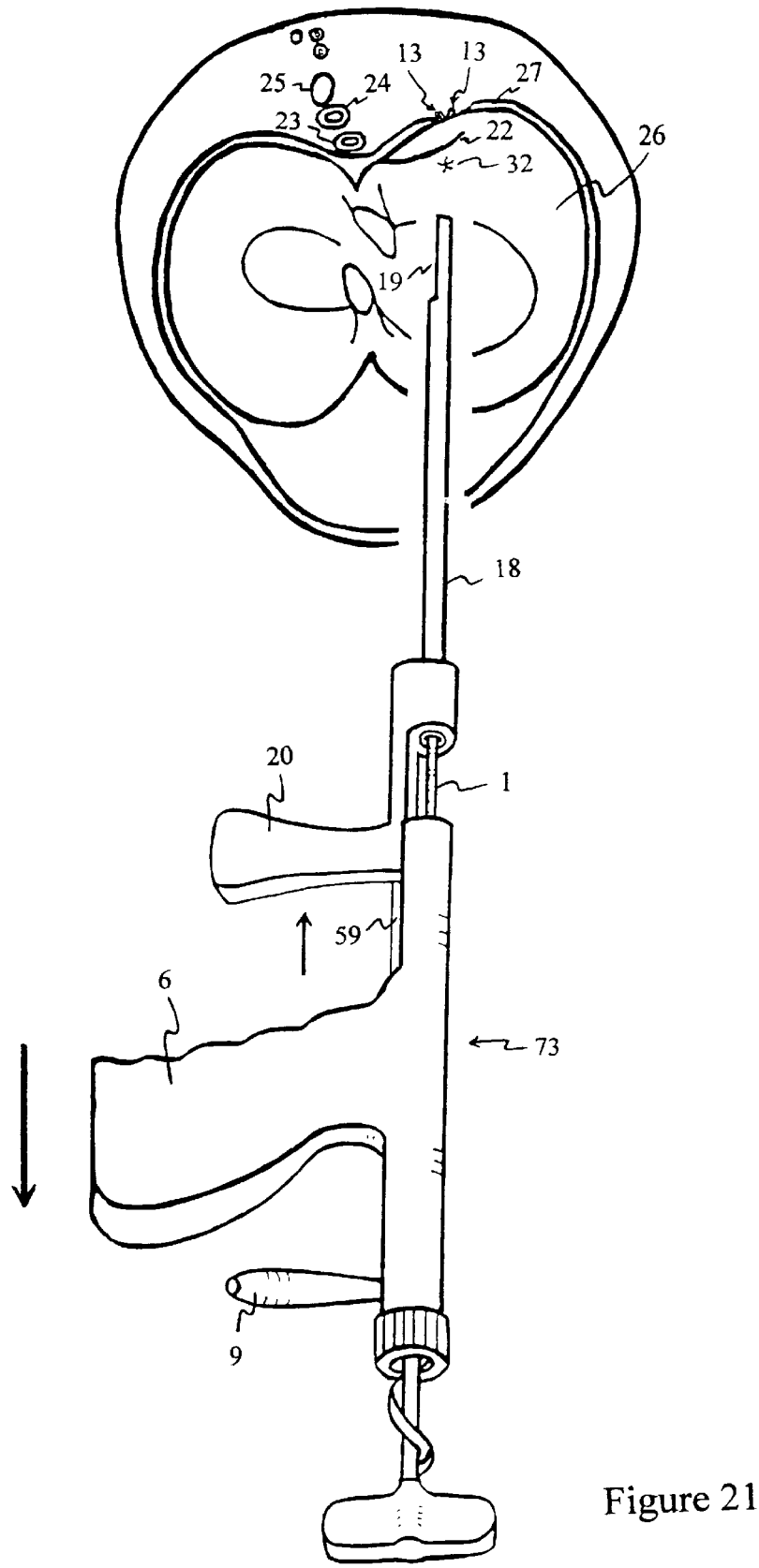
FIG. 21 shows the device withdrawn from the puncture site and the sleeve extended to cover the sharp needle to prevent scraping of articular cartilage. The fasteners remain elastically fastening the torn tissue.

FIG. 21 shows the device withdrawn from the puncture site 32. The fastener 13 slides through the slits 2, 8 and distal openings 16, 17 of both needle 1 and cartridge 7, as indicated in FIG. 4, and elastically fastens the torn tissue 22. In this case, there are a total of two deployed fasteners 13 holding the torn portion 22 of the meniscus 26. The sleeve 18 is then extended to cover the distal end of the needle 1 to prevent scraping of articular cartilage after the device 73 is withdrawn and possibly reset within the knee joint. Another fastener 13 can be advanced for another fastening if desired.

Due to the enormous pressures exerted at the femorotibial joint, meniscal tacks in the market today can creep and leave unhealing gaps along the meniscal tear. The springlike fasteners 13 in this invention, on the other hand, provide not only strong holding strength, they also provide springlike closure forces rejoining the torn tissue 22, thereby allowing the meniscus 26 to serve its function and to heal.

Although meniscal suture repair is believed to be reliable, it requires multiple and/or large incisions or entry points; and retractors are often required to pull aside blood vessels, nerves and even expand joint space for passage and manipulation of the suture. Each of these retractions involves risks, post-surgical complications, prolonged healing time and increased medical costs. On the other hand, the delivery device 73 for the spring-like fasteners 13 in the present invention consists of a needle 1 and components in the needle 1, which only require a small entry for fastener 13 delivery.

For simplicity in the remaining method descriptions, operative procedures of the device 73, such as out-of-phase, in-phase, fastener 13 advancement, sleeve 18 sliding, device 73 rotation, puncture or withdrawal will not be mentioned in great detail, unless the operation is greatly varied from that described above.

(B) Ligament Repair

During injury, meniscal 26 tears often accompany torn anterior cruciate ligaments 28 (ACL). As mentioned, the linear orientation of collagen fibers in the ACL 28 and the tensile strength requirement make it difficult to securely reattach the tear by suture, staple or any other existing means. Frequently, another ligament in the body is harvested or an artificial prosthetic device is used with extensive surgical incisions, drillings and attachments to replace the ACL 28.

To fortify the longitudinally oriented collagen fibers in a torn ACL 28, some specially designed fasteners 13 are deployed to grip and bundle the collagen fibers of the ACL 28 together like a collar. Frequently, the ACL 28 is stretched and irreversibly lengthened prior to breaking. Therefore the collar may not always be placed near the end of the tear. The placement of the collar is determined after manipulating and fitting the torn ACL 28 in the patient's leg to ensure appropriate length after reattachment.

Figure 22:
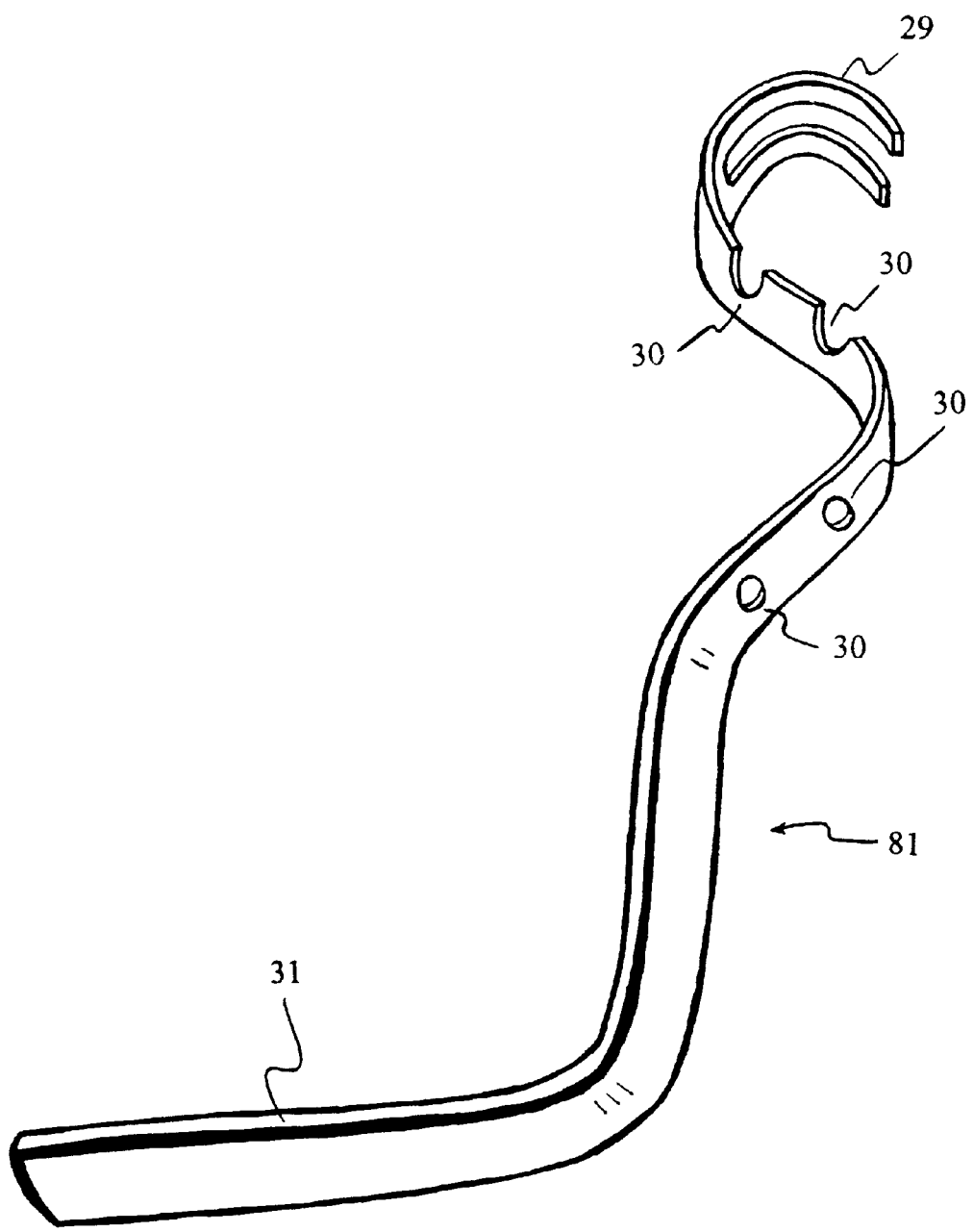
FIG. 22 depicts a ligament-holding device.

FIG. 22 shows a ligament holding device 81 with a handle 31, device guiding tracks 30 and a ligament holder 29. The ligament holding device is designed to hold the ACL 28 stationary and to guide insertion of the fastener delivery device 73 containing the collar fasteners 13 during endoscopic repair of a ligament 28.

Figure 23:
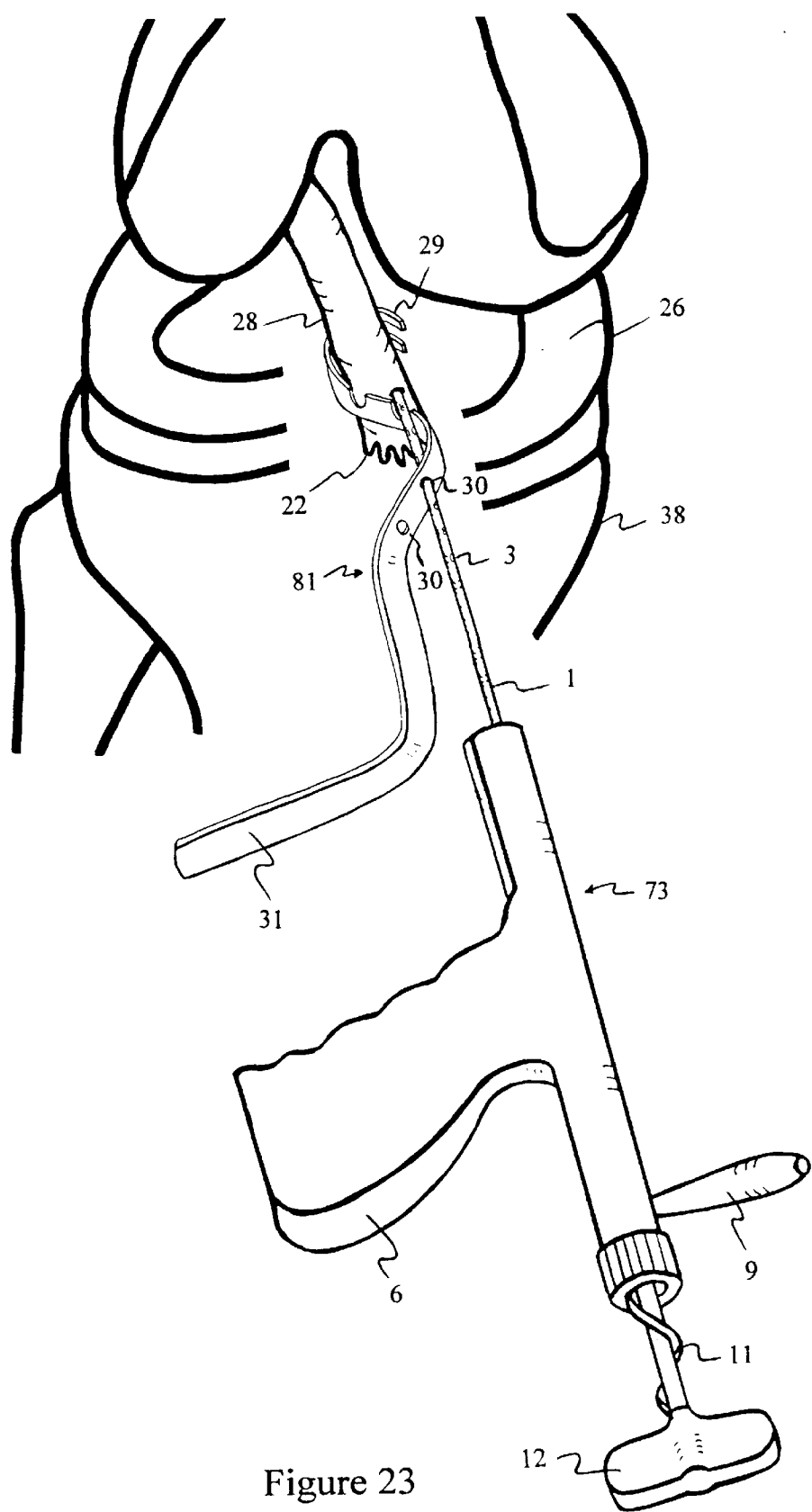
FIG. 23 depicts a torn anterior cruciate ligament, ACL, held by the ligament holder. The fastener delivery device is inserted through the guiding track near the torn tissue of the ACL.

FIG. 23 shows a torn ACL 28 held by the ligament holder 29. Guided by an arthroscope, not shown, through the device guiding track 30, the fastener delivery device 73 is inserted near the torn tissue 22 of the ACL 28. Specifically designed fasteners 13 for gripping and holding ligament fibers are deployed in the ACL 28, in this example, one on each side positioned by the guiding tracks 30.

Figure 24:
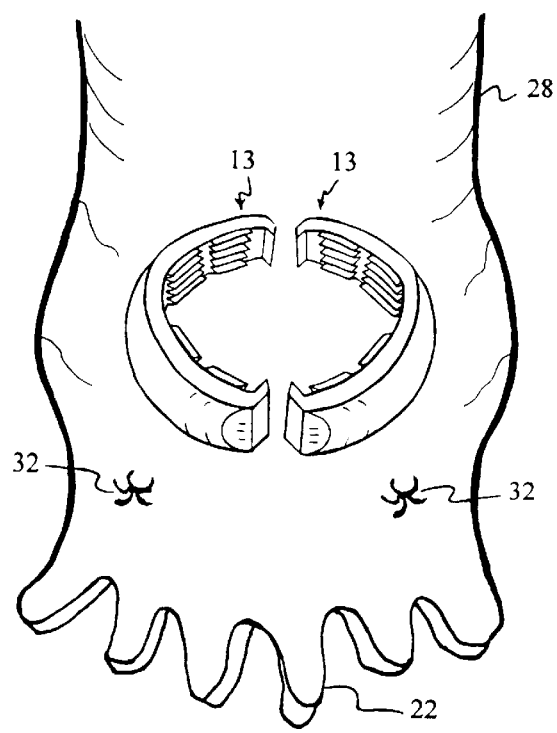
FIG. 24 depicts the deployed fasteners holding the ligament fibers like a collar above the torn tissue of the ACL.

FIG. 24 depicts the deployed fasteners 13 holding the ligament fibers like a collar or ring above the torn tissue 22 of the ACL 28. The curvature and closure strength of the collar fasteners 13 are designed to hold, bundle and fortify the collagen fibers of the ligament 28. The gripping elements 14 of the collar fasteners 13 are designed and directed to resist, in this example, the downward pulling forces. The fastener delivery device 73 puncture sites 32 are shown.

Figure 25:
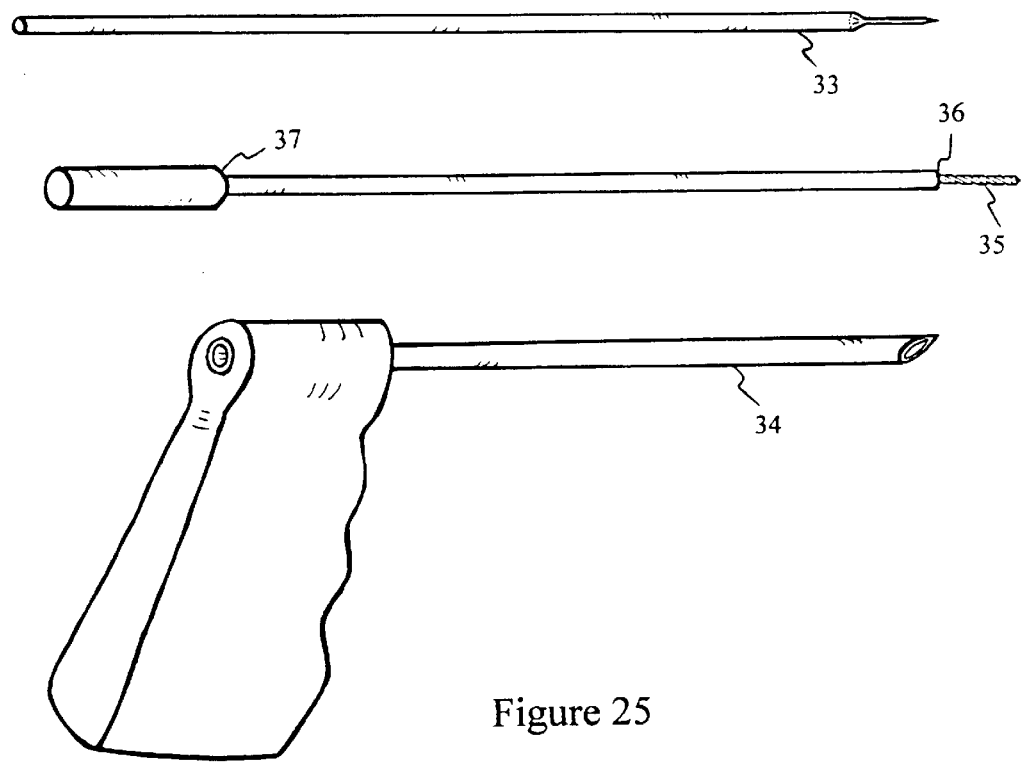
FIG. 25 depicts a set of tissue manipulating and bone drilling tools: a trocar, a drill and a cannula.
Figure 26:
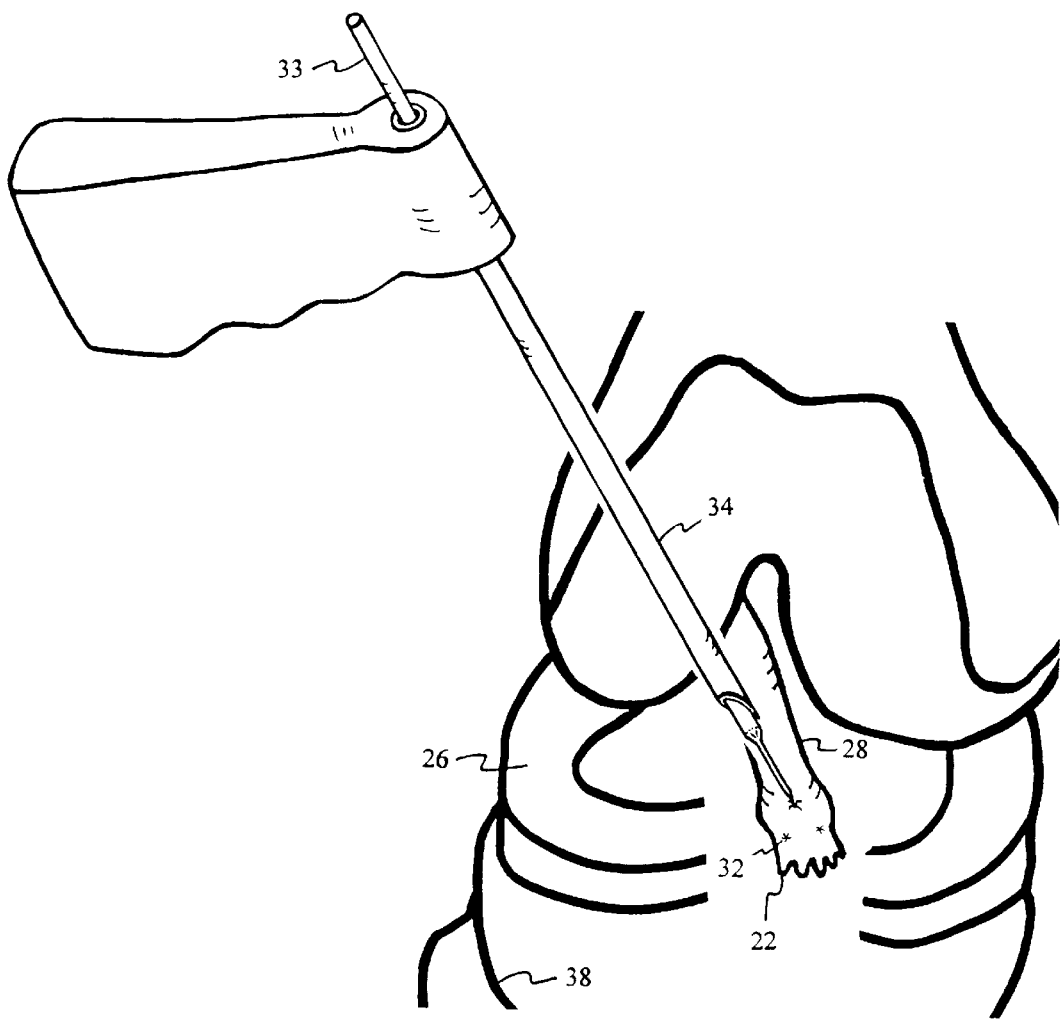
FIG. 26 depicts the piercing of the trocar and the cannula through the ACL onto the surface of the bone.
Figure 27:
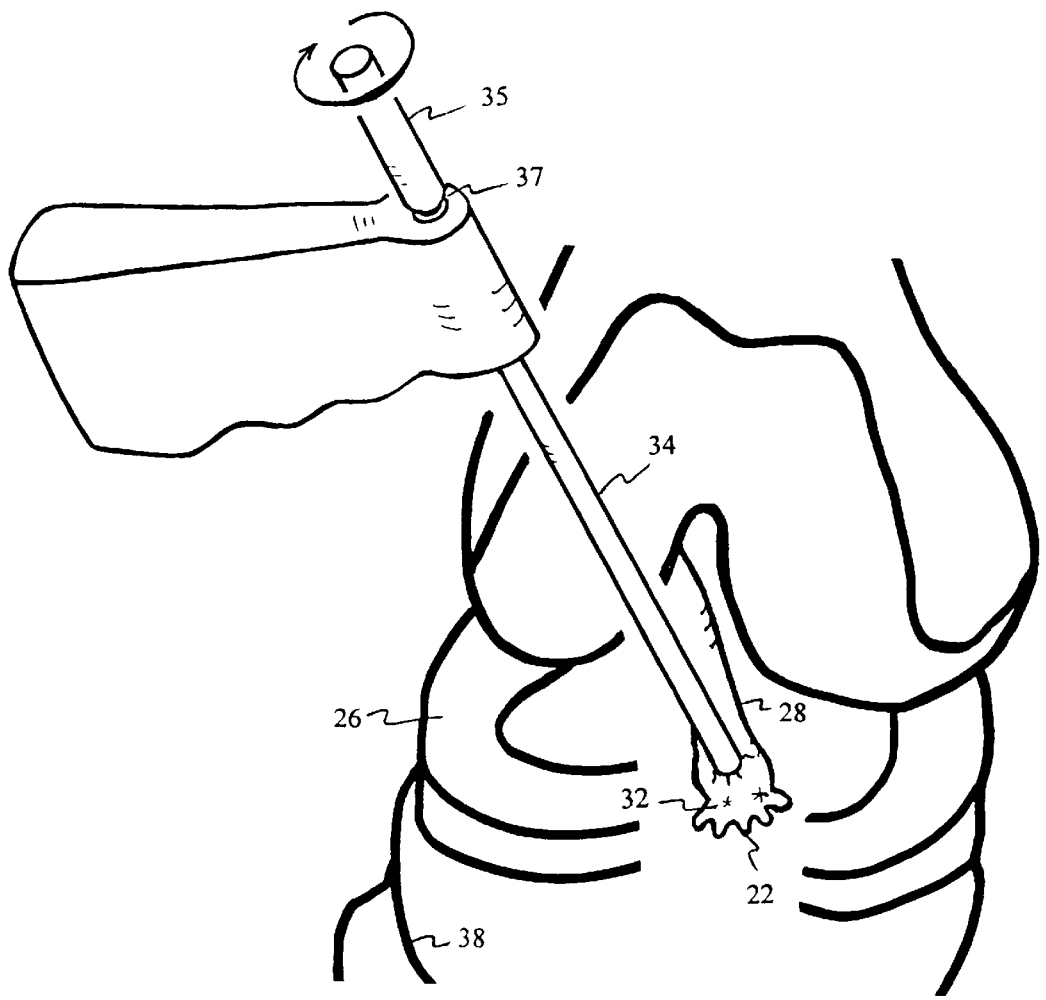
FIG. 27 shows the trocar replaced with a drill while the cannula is held stationary on the bone.
Figure 28:
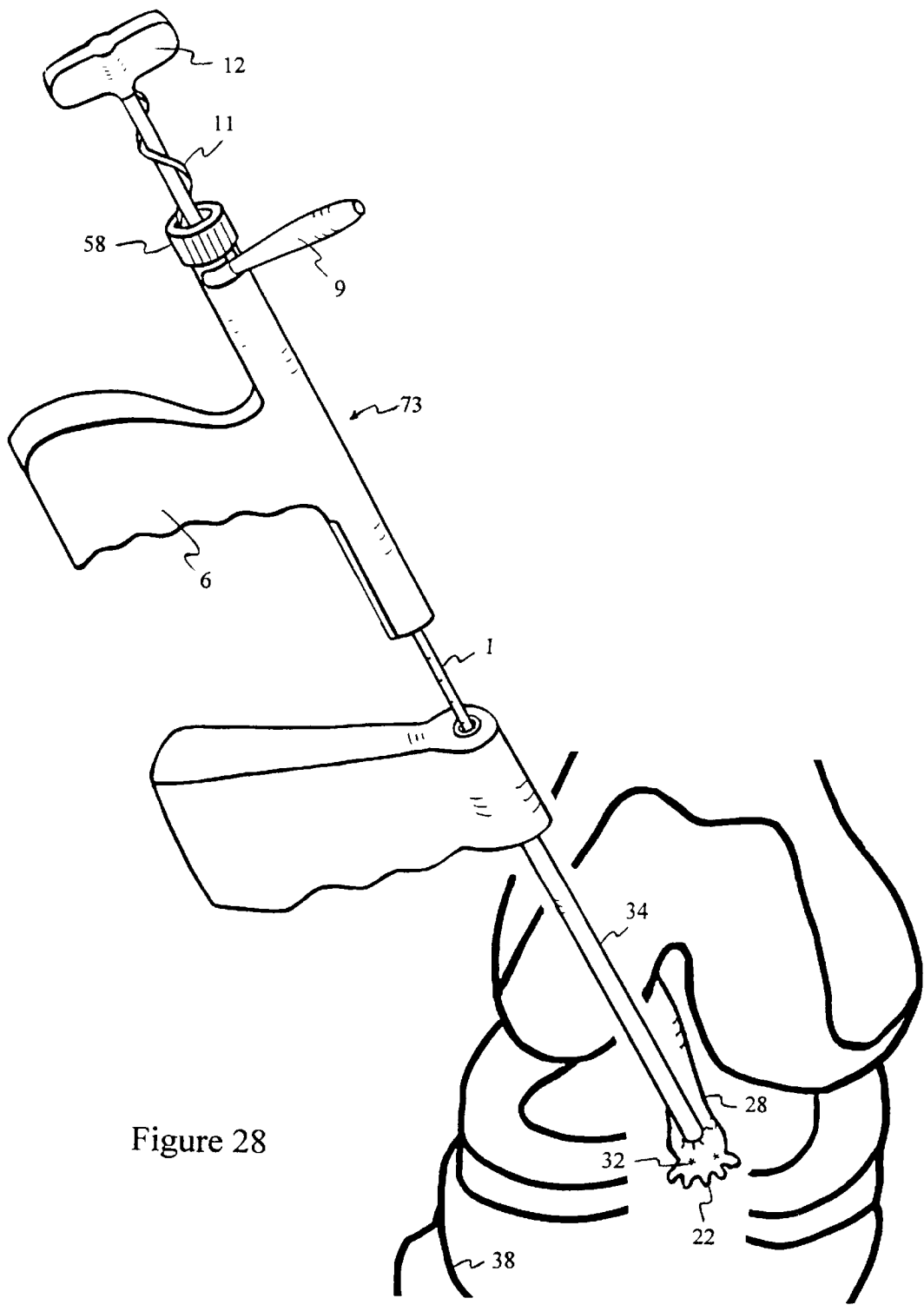
FIG. 28 shows the cannula held stationary while the drill is replaced with the fastener delivery device inserted into the bone hole.

FIG. 25 depicts a set of tissue manipulating and bone drilling tools for reattaching a torn ligament or tendon. For ACL tears close to the tibia or femur, a trocar 33 having a sharp distal tip is passed through the collar to the surface of the bone 38 to establish an ACL 28 reattachment position. A cannula 34 with a handle and a sharp distal tip is inserted over the trocar 33 and contacts the bone 38, as shown in FIG. 26. The trocar 33 is then removed and replaced with a drill 35, as shown in FIG. 27. While the cannula 34 is held stationary on the bone 38, a hole is drilled into the bone 38, with depth predetermined by the bone stop 36 and cannula stop 37, as indicated in FIG. 25. FIG. 28 shows the cannula 34 held stationary, while the drill 35 is replaced with the fastener delivery device 73 set out-of-phase and inserted into the bone hole.

Figure 29:
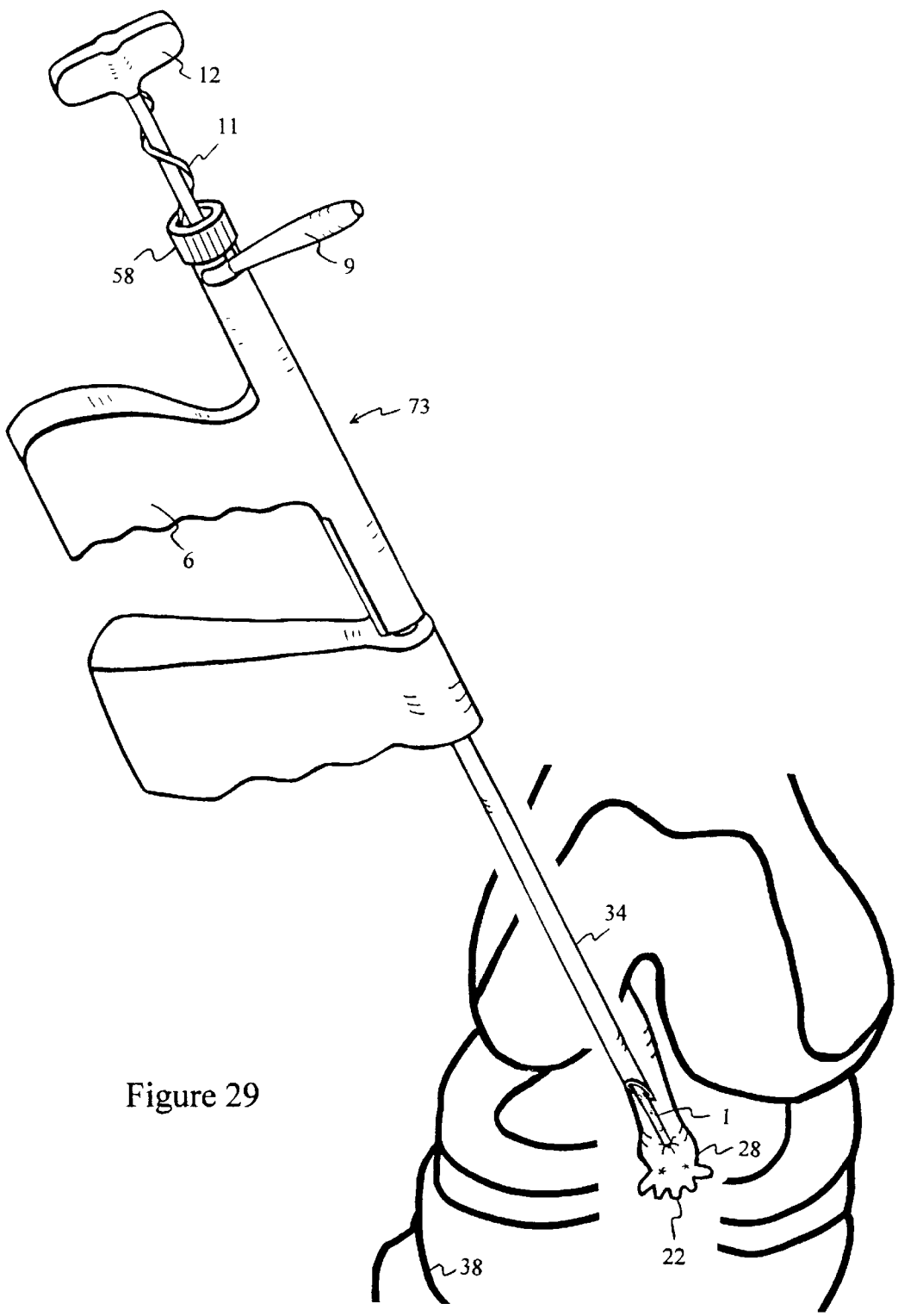
FIG. 29 shows the cannula withdrawn from the ACL to allow the ACL fibers to contact the needle, especially the needle slit.

Unlike the collar fasteners 13 mentioned earlier, the gripping elements 14 for the bone 38 attachment are designed to resist vertical or longitudinal pull out. The length of the fasteners 13 is sufficient to span the depth of the drilled hole to beyond the collar of the torn ACL 28, depicted in FIG. 24. Prior to deployment of the fasteners 13, the cannula 34 is lifted beyond the slit 2 of the needle 1, as shown in FIG. 29. The collagen fibers of the ACL 28 are in contact with the delivery device 73, especially with the slit 2 portion of the needle 1. The first fastener 13 is then deployed.

Figure 30:
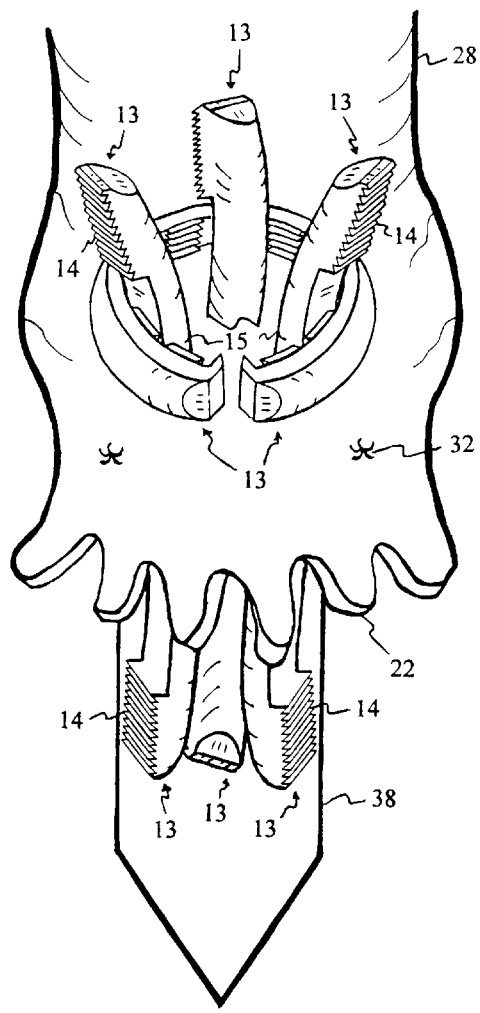
FIG. 30 depicts the anchoring of the ACL fortified by three fasteners extending from the cone-shaped hole in the bone to beyond the collar fasteners around the ACL.

FIG. 30 depicts the gripping of three deployed fasteners 13 after the withdrawal of the fastener delivery device 73. The distal portion of the fasteners 13 in the cone-shaped bone hole tightly grip and anchor the bone 38. The proximal portion of the fasteners 13 grip the collar-fortified ACL 28 fibers. Due to the spring-like property built into the fastener body 13, the gripping elements 14 at both portions are constantly compressing the tissues, in this case the ACL 28 fibers and bone 38, making the fastening strength exceptionally strong. To ensure adequately strong reattachment, multiple fasteners 13, preferably deployed in different directions, can be loaded into the same drilled hole without completely lifting the fastener delivery device 73.

For deployment of multiple fasteners 13, the device 73 in the puncture site 32 is reset to the out-of-phase mode. As mentioned, it is possible that a portion of the deployed fastener 13 may remain in the cartridge 7 and restrict the cartridge 7 from rotating back to the out-of-phase mode. To free the cartridge 7 from the deployed fastener 13, the device 73 may have to be slightly withdrawn from the puncture site 32 to depart or be free from the deployed fastener 13 prior to rotation. Another fastener 13 may then be advanced to the deploy position within the cartridge 7. The device 73 is rotated slightly to alter the direction of the next fastener 13 deployment This procedure is repeated until the torn 22 ACL 28 is tightly fastened onto the bone 38.

Often, the ACL 28 is torn at or near its mid-section. A similar technique with the ligament holder 29 and collar fasteners 13 is used to install two sets of collars, one on each torn end of the ACL 28. The placements of these collar fasteners 13 also are determined after manipulating and fitting the ACL 28 fragments in the patient's leg to ensure appropriate length after reconnecting the ACL 28.

Figure 31:
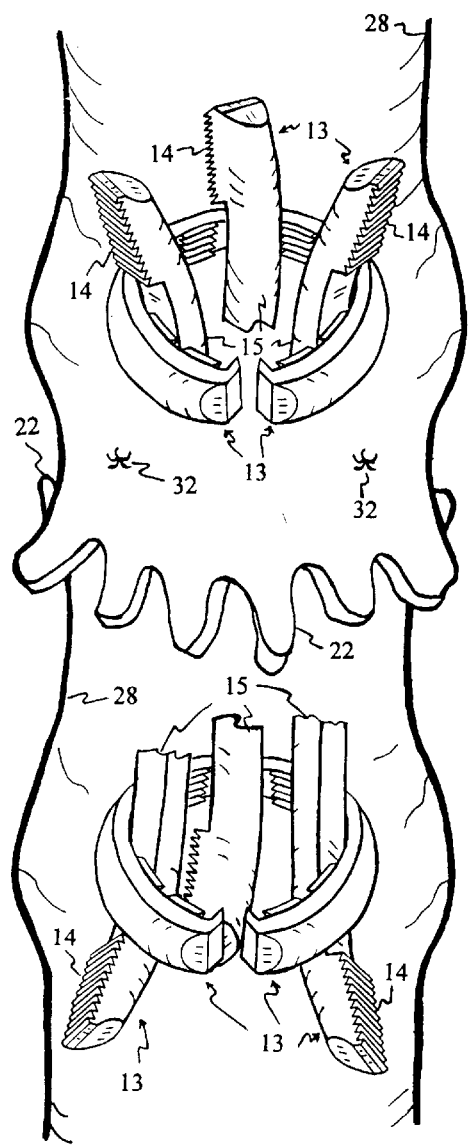
FIG. 31 shows an ACL rupture more distant from bone. Two sets of collar fasteners are installed near the torn ends of the ACL. Three fasteners are deployed to reattach the collar fasteners fortifying the ACL fragments.

To attach two collar fortified ACL 28 fragments, the needle 1 is inserted through both sets of collars, bridged by the indented slit 2. Distally semi-deploying the first fastener 13 may be helpful to pull and manipulate the distal ACL 28 fragment into place. Sliding the sleeve 18 over the needle 1 can also be used to push tissue, in this case the proximal ACL 28 fragment, to tightly rejoin the ACL 28 fragments. The fastener 13 is then fully deployed, gripping both fragments of ACL 28 fibers fortified by two sets of collars 13. Due to the high tensile strength required during normal function of the ACL 28, adding multiple fasteners 13 is recommended to ensure a successful ACL 28 repair. Therefore, after the initial fastener 13 deployment, the device 73 is reset to out-of-phase mode, another fastener 13 is advanced, and the device 73 is rotated to deploy another fastener 13. The procedure is repeated until the two ACL 28 segments are firmly reattached by the deployed fasteners 13, as shown in FIG. 31. Again, it is possible that a portion of the deployed fastener 13 may remain in and restrict the rotation of the cartridge 7. A slight withdrawal of the device 73 may be necessary before resetting it to the out-of-phase mode.

In alternate methods, the collar fasteners 13 may be tied with sutures to another set of collar fasteners 13, to a tunnel through the bone 38, a bone anchor, etc.

By fortifying and reattaching the torn ACL 28 with fasteners 13, the patient has avoided the trauma of replacement harvesting and extensive bone drilling required by conventional ACL 28 repair.

(C) Tendon Repair

A tendon 40 torn from the bone 38 is common among sport injuries and accidents. Generally, there are two major approaches for reattaching a tendon 40 back to the bone 38. The traditional repair is to drill through the bone 38, then pass a suture to attach the torn tendon 40 back to the bone 38. Recently, tendon 40 repair has been done using less invasive drilling and artificial bone anchors with attaching sutures, which are fitted into a shallowly drilled hole in the bone 38. Even with bone anchors, suture manipulation requires both time from surgeons and surgical space within the patient, which may lead to large or multiple incisions.

Similar to reattaching the ACL 28 to the bone 38, a trocar 33 is used to pierce and guide the tendon 40 into proper position, where a hole will be drilled in the bone 38. A cannula 34 is inserted over the trocar 33, and then the trocar 33 is replaced with a drill 35 creating a hole in the bone 38. The drill 35 is then replaced by the fastener delivery device 73 inserted through the tendon 40 into the bottom of the bone hole. The cannula 34 is lifted so that the slit 2 opening of the needle 1 is in contact with tendon tissue 40. If necessary, the tendon 40 can be pushed and positioned by the sliding sleeve 18. The fasteners 13 in the device 73 should have sufficient length to grip both the bone 38 and the tendon tissue 40. With time, similar to the reattached ligament, the tendon 40 can and most likely will permanently reattach back onto bone 38.

Figure 32:
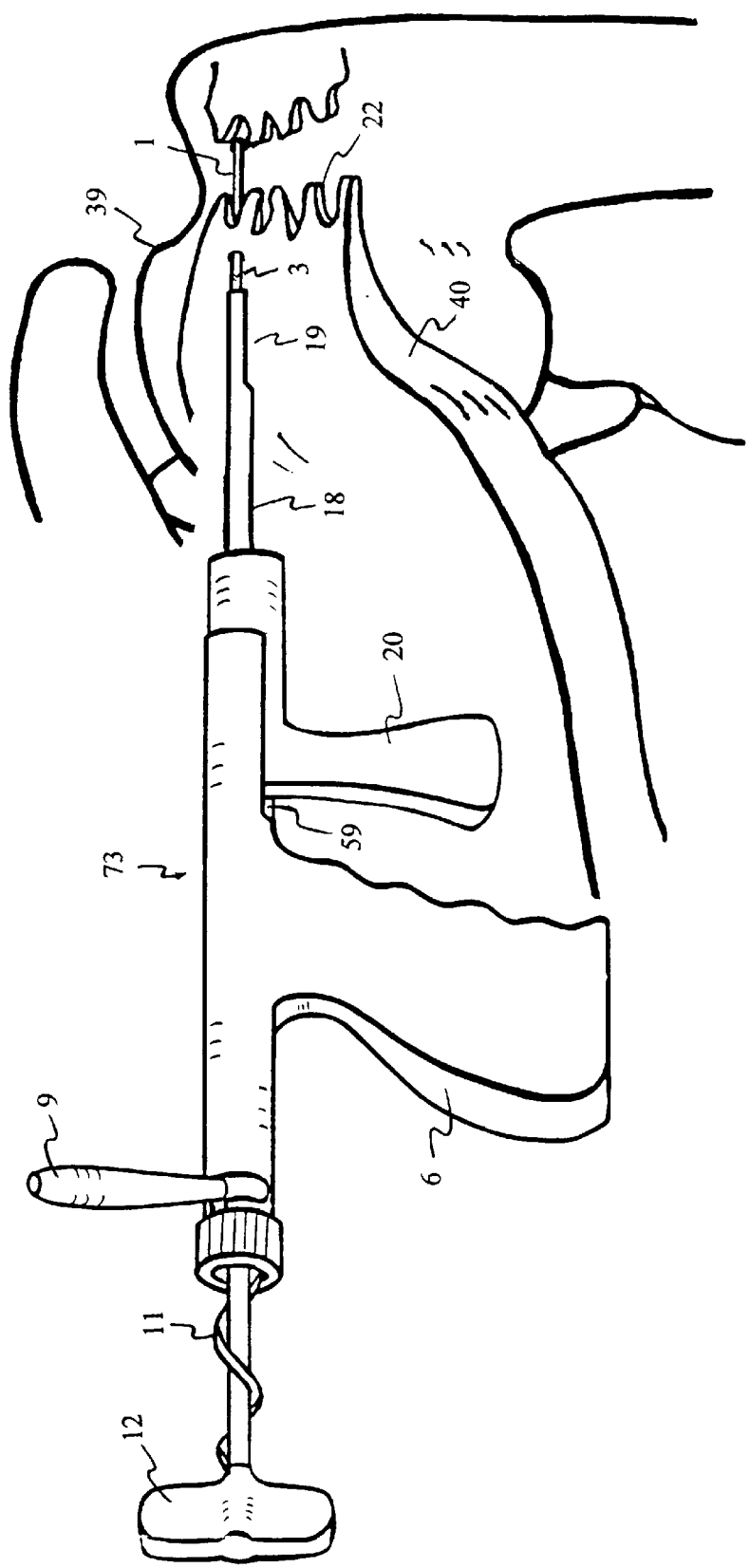
FIG. 32 depicts a tendon torn from the humerus. A fastener delivery device is inserted into the tendon and pierces the humerus.

For soft bone, such as the humerus 39 in the shoulder, the needle 1 of the device 73 could possibly pierce a tendon 40 to be reattached and puncture into the humerus 39 without using the trocar 33, cannula 34 and drill 35. FIG. 32 depicts a tendon 40 torn from the humerus 39. The fastener delivery device 73 can be inserted through a small opening and guided by an endoscope to reattach a tendon 40 back to the humerus 39 without suture sewing, manipulating or tying.

Figure 33:
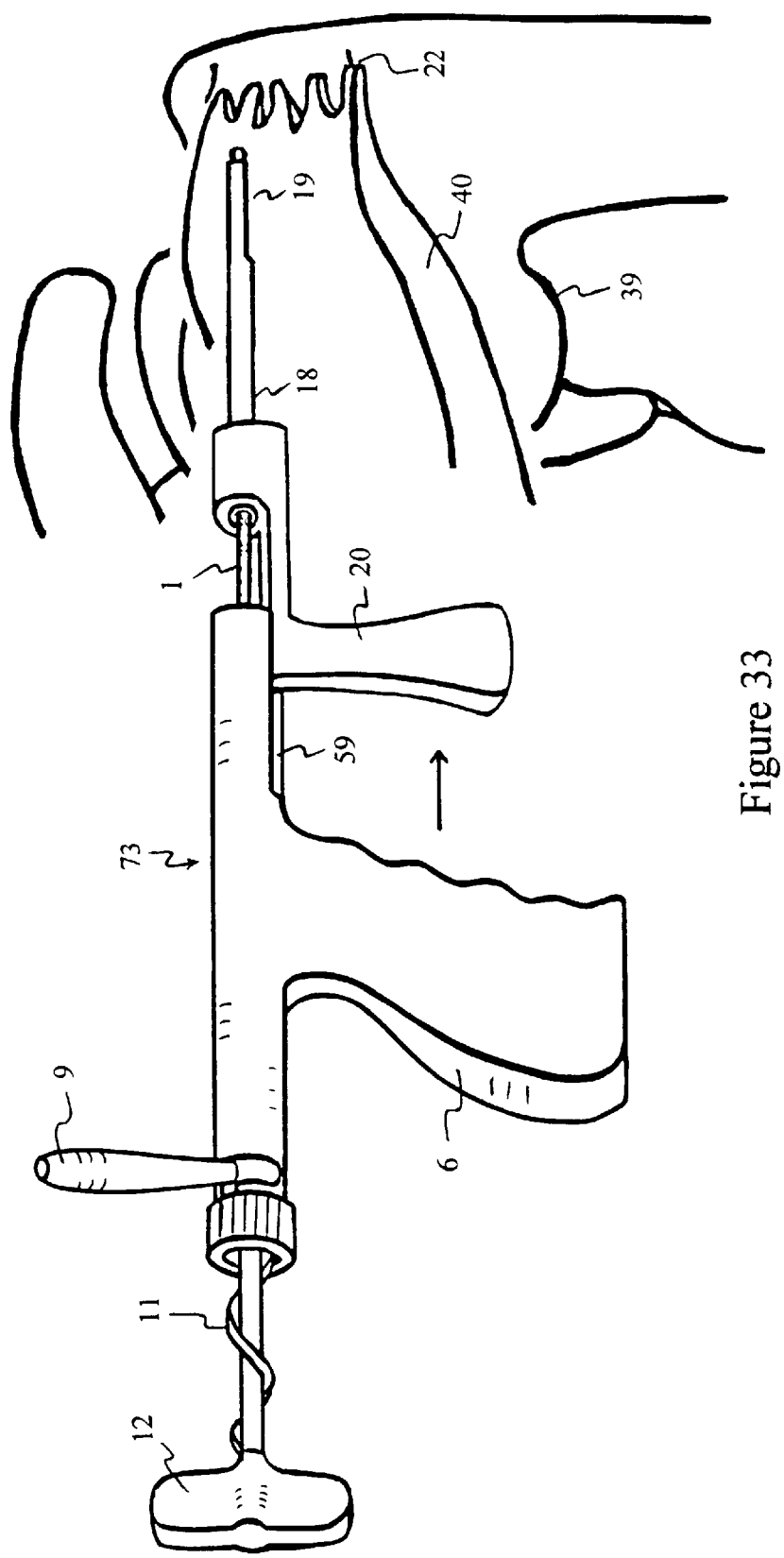
FIG. 33 shows the tendon being positioned by the sleeve, as the tendon is reattached to the humerus.

FIG. 33 shows how a surgeon can use the sleeve 18 to push and position the tendon 40 back to the humerus 39 endoscopically. Similar to the ACL 28 repair indicated in FIG. 30, the fasteners 13 should be long enough to extend from the hole pierced in the humerus 39 to the tendon 40 tissue. After the tendon 40 has been positioned, the fastener 13 is deployed to anchor the tendon 40 back to the humerus 39. The device operation is similar to that previously described. Multiple fasteners 13 can be deployed to fly fasten the ruptured tendon 40.

(D) Bulging or Herniated Disc Fastening and Repair

Figure 34:
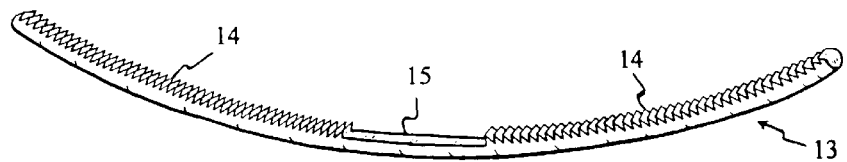
FIG. 34 depicts a long fastener with spring-like or shape memory elements and multiple gripping elements.

Low back pain from bulging or herniated discs 41 is one of the most prevalent, painful and debilitating ailments afflicting mankind. As mentioned, treatments ranging from the traditional to the percutaneous approaches all have their drawbacks, some are very serious. All these approaches have one thing in common: tissue removal. Vastly different from the tissue removing procedures, the methods described herein use various techniques and devices to fasten the bulging or herniated disc 41 to alleviate nerve 25 impingement To fasten a bulging or herniated disc 41, the spring-like fasteners 13 of the invention are made extra long with multiple gripping elements 14. FIG. 34 depicts a long fastener 13 with a spring-like or shape memory element 15 and multiple gripping elements 14 on both ends. This type of fastener may be suitable for intervertebral use, especially for fastening bulging or herniated discs 41 of the spine.

Figure 35:
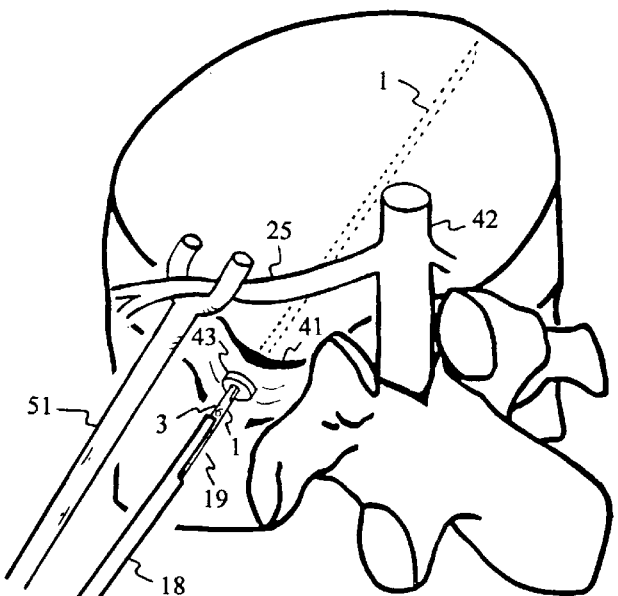
FIG. 35 depicts a nerve retractor lifting an impinged nerve away from a bulging or herniated disc. A fastener delivery device is inserted with a sealing patch into the bulging or herniated portion of the disc.
Figure 35:
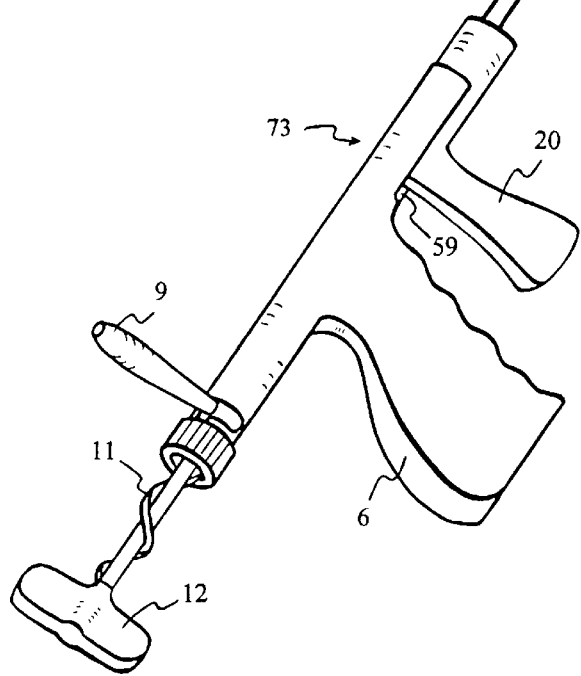

FIG. 35 depicts a nerve retractor 51 lifting an impinged nerve 25 away from a bulging or herniated disc 41. A delivery device 73 is loaded with a fastener 13 similar to the one in FIG. 34. For the best result, the needle 1 of the fastener delivery device 73 punctures the bulging portion and is guided into the disc 41 by anteroposterior and lateral fluoroscopy or other technique. In cases where the bulging portion of the disc 41 is well concealed by the lamina of the vertebra, a small amount of the bone can be removed to allow penetration of the delivery device 73.

To prevent possible leakage of the nucleus pulposus around the fastener 13, prior to device 73 insertion into the disc 41, an optional sealing patch 43, made with elastic and biocompatible material with closure capability, may be inserted on the needle 1 near the proximal portion of the needle slit 2. For best results, the sleeve 18 is fixed proximally and stationary to provide a position where the proximal tip of the soon to be deployed fastener 13 will grip the sealing patch 43. Using similar guiding, inserting and compressing techniques, the sealing patch 43 is tightly compressed, adhered or maybe even embedded into the previously bulging or herniated annulus 41. As the fastener 13 is deployed, it grips the patch 43 to seal possible leakage of nucleus pulposus.

Figure 36:
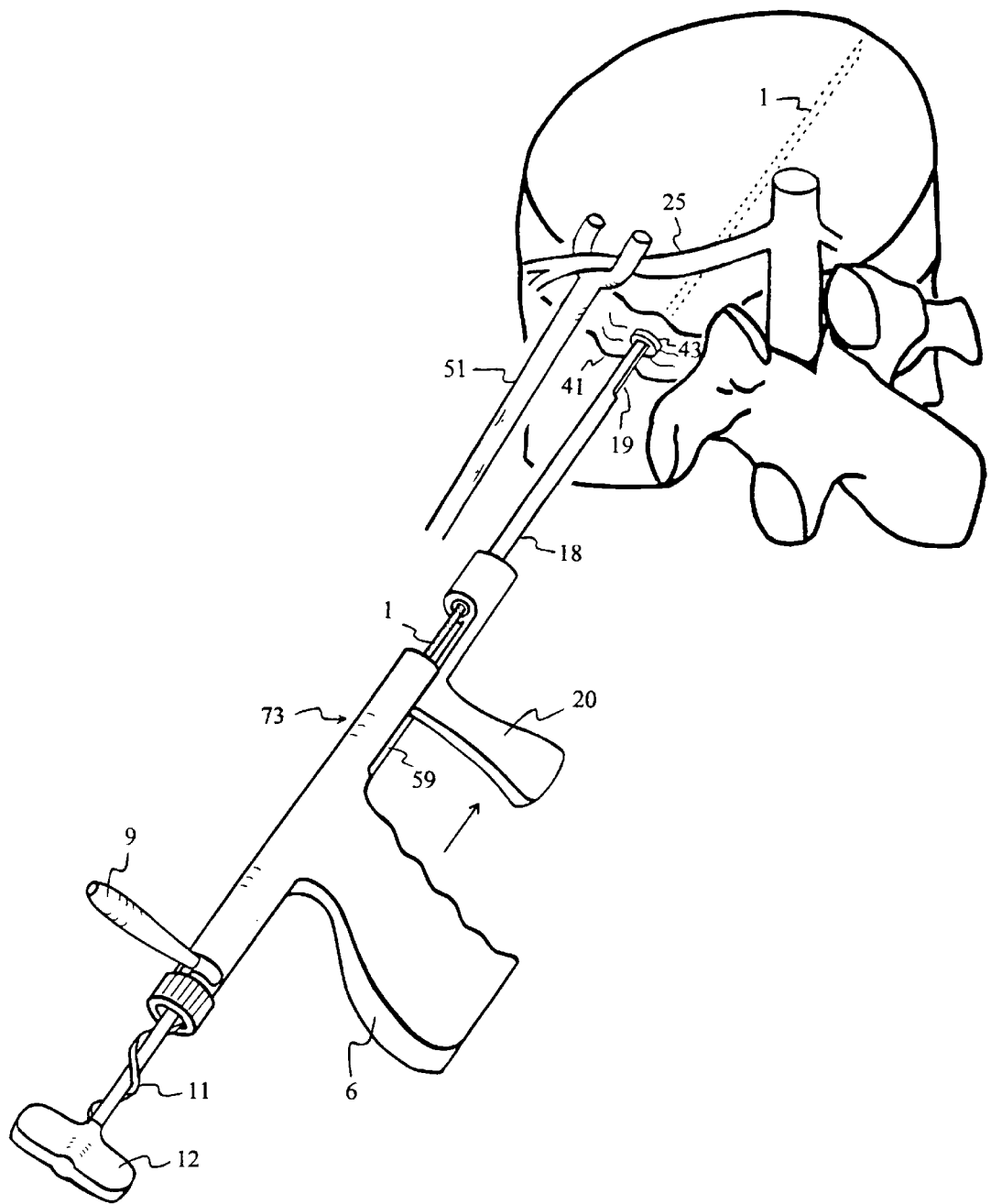
FIG. 36 depicts the compression of the bulging disc by the sleeve. The sealing patch is also pressed against the bulging disc.
Figure 37:
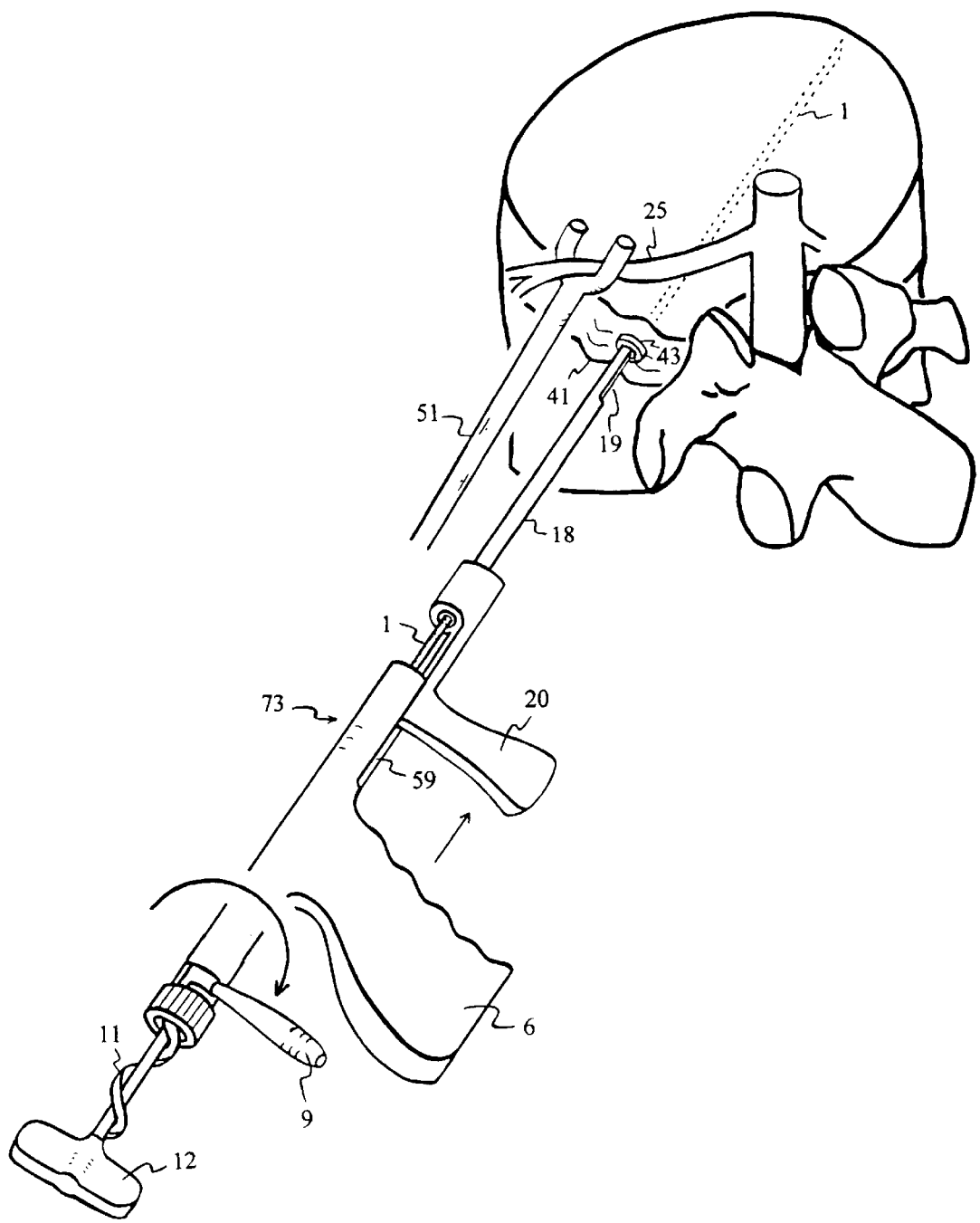
FIG. 37 shows the cartridge handle turned to deploy the fastener into the disc while the sleeve and sealing patch compress the bulge.

FIG. 36 depicts the compression of the bulging disc 41 and the optional sealing patch 43 around the sleeve 18, when the appropriate depth is reached. While compression continues, the fastener 13 is deployed to grip and compress the previously bulging tissue back in place as shown in FIG. 37. To make possible the push and hold technique using the sleeve 18 during deployment of the fastener 18, the distal end of the sleeve 18 also contains a slit 19, which overlaps the slit 2 of the needle 1. As the device 73 is set in the in-phase mode, all three slits 2, 8, 19 of the needle 1, cartridge 7 and sleeve 18 are aligned, allowing the fastener 13 to deploy and hold the compressed tissue in place. When applied prior to fastener deployment, the sealing patch 43 is also compressed against the bulging disc 41. The sealing patch 43 is made with elastic and conforming material capable of sealing potential leakage of nucleus polposus. However, the annulus may be self-sealing with no significant leakage of nucleus pulposus. Therefore, the sealing patch 43 is optional.

Figure 38:
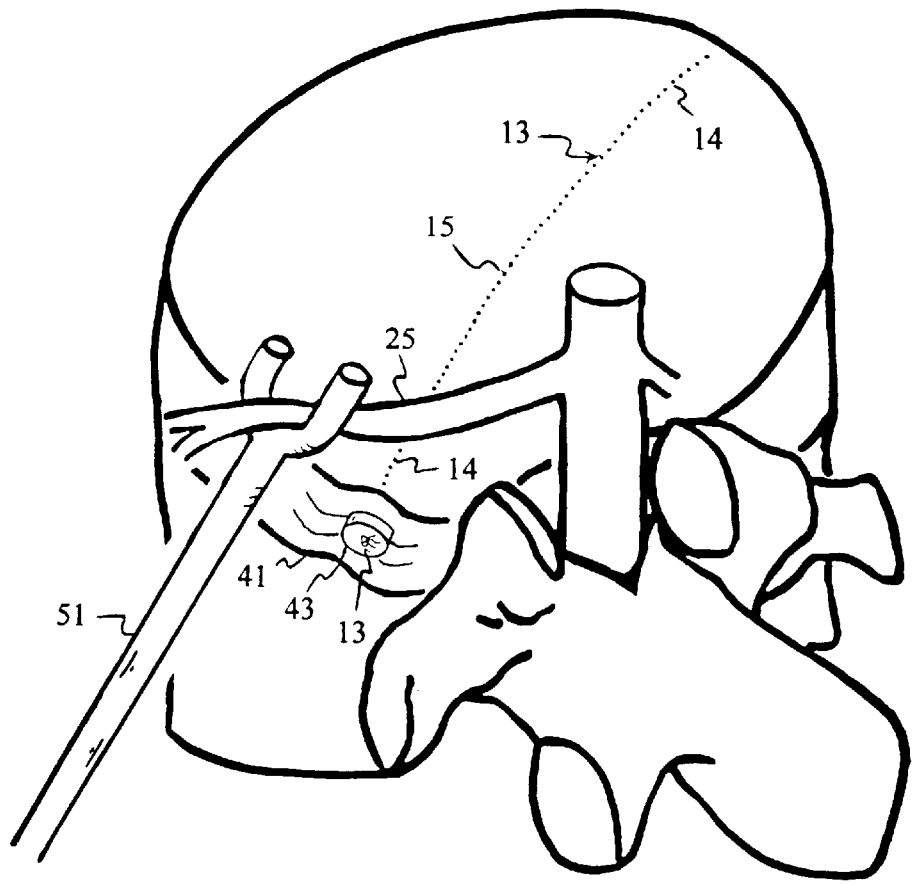
FIG. 38 shows the device withdrawal with the fastener remaining within the disc, gripping and fastening the previously bulging annulus.

Once the device 73 has been withdrawn, as shown in FIG. 38, the fastener 13 remains within the disc 41 with constant gripping and fastening forces maintained and substantiated by the spring-like or shape memory element 15, thereby holding back the previously bulging annulus 41.

Similar to previously mentioned surgical procedures, more than one fastener 13 can be deployed through the puncture site 32, preferably toward different directions, to enhance a permanent fastening. The spring-like fasteners 13 with multiple gripping elements 14 provide an exceptionally strong holding strength, away from nerves.

Figure 39:
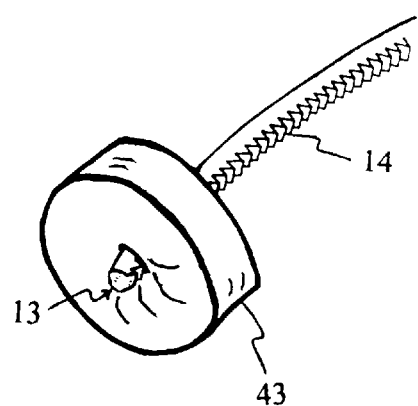
FIG. 39 depicts a sealing patch gripped by the proximal portion of the fastener outside the repaired annulus (not shown).

FIG. 39 depicts the sealing patch 43 gripped by the proximal portion of the fastener 13 outside the repaired annulus, not shown. The main function of the sealing patch 43 is to prevent possible leakage of the nucleus polposus. The preferred materials used in constructing the patch 43 are silicone rubber, elastic polymer or biomaterial. Polyurethane or other material can be added or sandwiched to strengthen the sealing patch 43. However, the sealing patch 43 is optional, and the fastener 13 can be deployed entirely within the disc, without protrusion.

Figure 40:
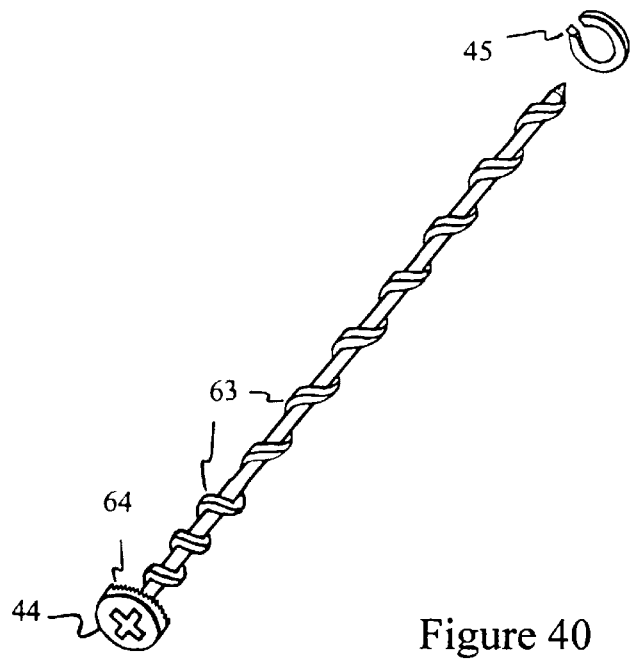
FIG. 40 depicts a disc fastening screw with a washer used to fasten a bulging or herniated disc.

For fastening bulging discs 41, devices other than the fastener delivery device 73 can be used. FIG. 40 shows an alternate device using a disc fastening screw 44 with variably pitched threads 63 designed to compress and fasten the bulging annulus. The screw 44 may be inserted directly in the disc 41 or a pre-punctured hole may be used. A washer 45 containing a locking nub in conjunction with the locking teeth 64 prevents loosening of the screw 44.

Figure 41:
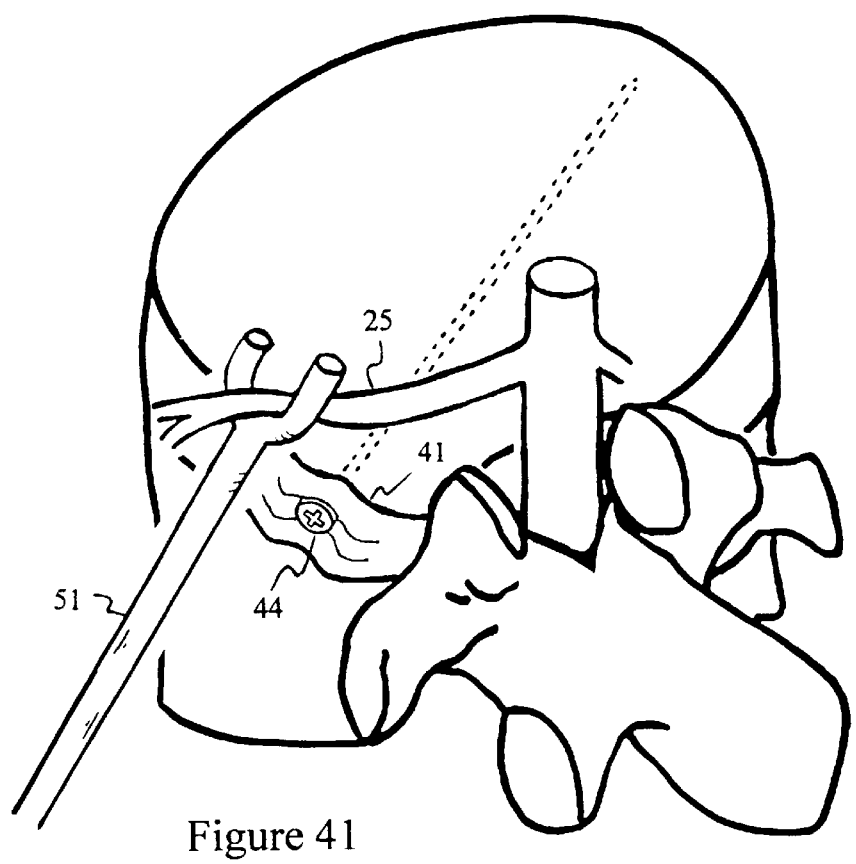
FIG. 41 depicts the fastening of the previously bulging or herniated disc by the disc fastening screw.

A needle puncturing a bulging disc may be guided by a three-dimensional viewing technique as mentioned, creating an entry for the disc fastening screw 44. After the withdrawal of the needle, the screw 44 enters to fasten the previously bulging disc 41, as shown in FIG. 41. The optional sealing patch 43 can be used in conjunction with the screw 44 and washer 45.

Figure 42:
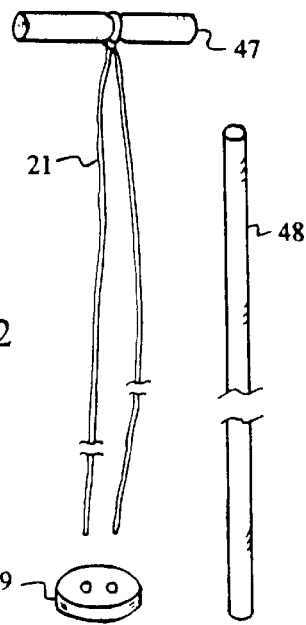
FIG. 42 depicts another bulging or herniated disc fastening device using a suture tied to a dumbbell shaped rod. A plunger is used to deploy the rod and a washer is used for tying with the suture to compress the bulging disc.
Figure 43:
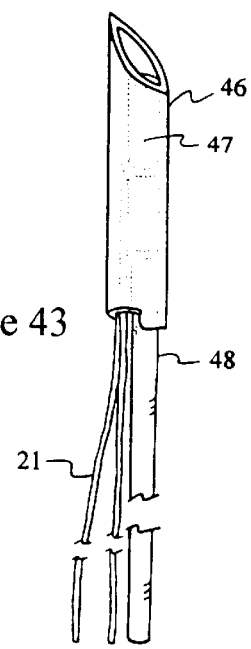
FIG. 43 depicts the assembly of the rod, suture and plunger inside a spinal needle.

Sutures 21 can also be used to fasten a bulging or herniated disc 41. Sutures 21 may be made of natural materials, such as gut, polymers, such as polyester, nylon and PTFE, or metals, such as stainless steel. FIG. 42 depicts another bulging or herniated disc fastening device using a suture 21 tied to the midsection of a dumbbell shaped rod 47. The rod 47 with suture 21 is fitted inside a spinal needle 46. Behind the rod 47, a plunger 48 is inserted into the spinal needle 46. FIG. 43 depicts the assembly of the rod 47, suture 21 and plunger 48 inside a spinal needle 46.

Figure 44:
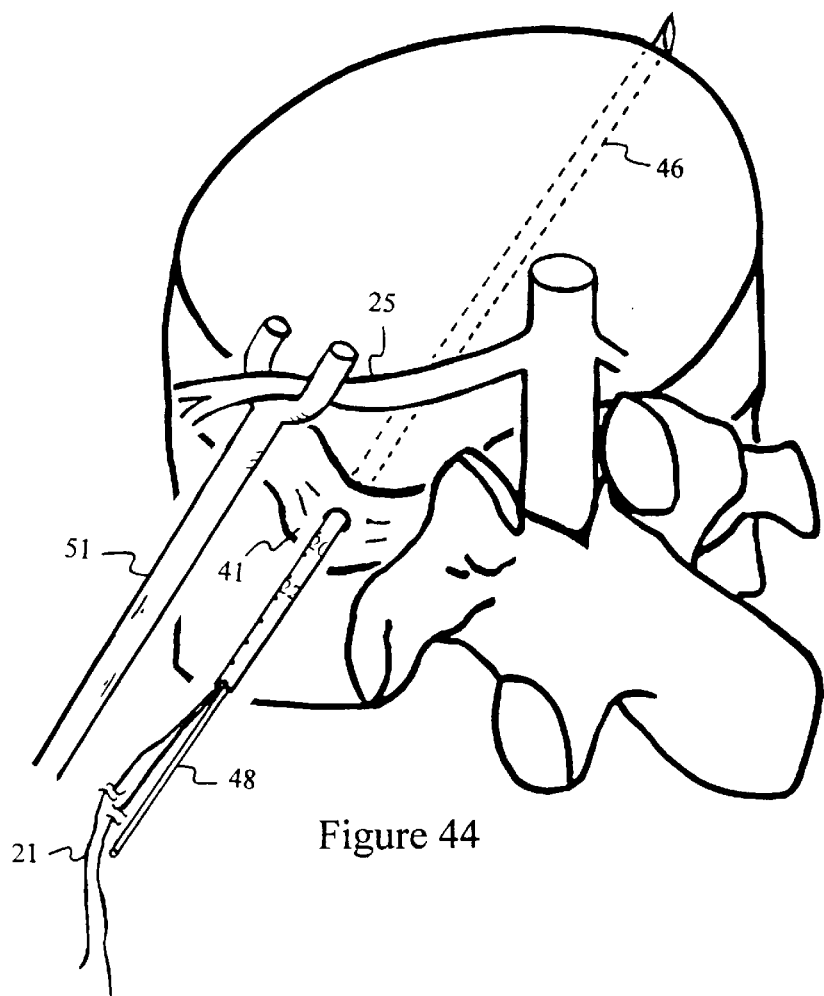
FIG. 44 depicts a puncture using the spinal needle containing the assembly of the rod, suture and plunger, as indicated in FIG. 43, through the bulging or herniated disc.
Figure 45:
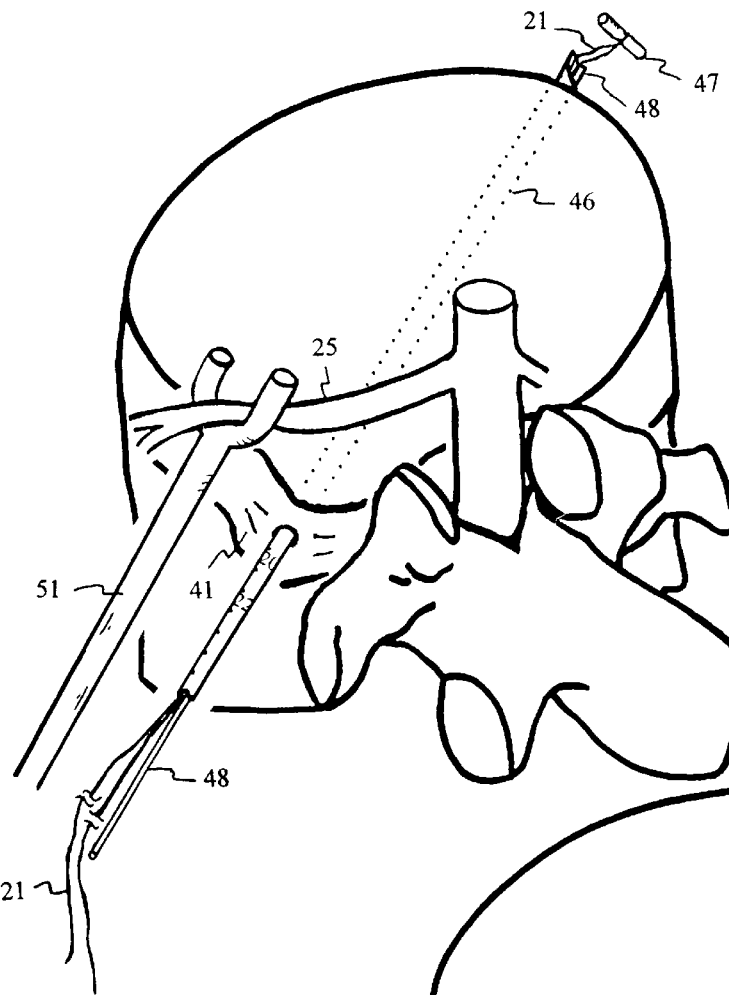
FIG. 45 shows the rod tied to the suture and deployed out of the distal opening of the spinal needle and out of the disc by the pushing of the plunger.

FIG. 44 depicts a guided puncture using the spinal needle 46 containing the assembly of the rod 47, suture 21 and plunger 48, as indicated in FIG. 43, through the bulging or herniated disc 41. To avoid potential damage to vessels, nerves or other tissue, the protrusion of the distal tip should be minimal. With the plunger 48, the rod 47 is pushed out of the distal opening of the spinal needle 46, outside the annulus as indicated in FIG. 45.

Figure 46:
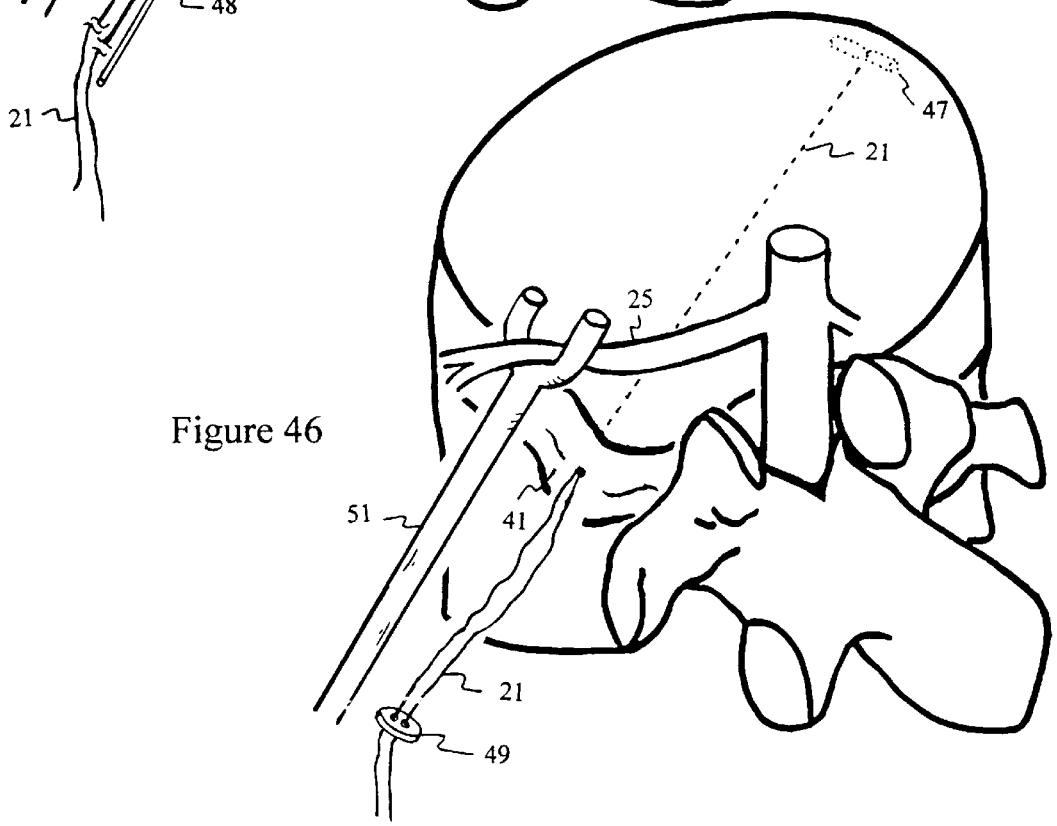
FIG. 46 shows the spinal needle withdrawn. The rod is anchored outside the disc holding the suture. The washer is then threaded through with the ends of the suture.

The rod 47 is now caught by the outer surface of the annulus and acts as an anchoring device for the suture 21. The spinal needle 46 is removed, as shown in FIG. 46. A washer 49 is threaded with the suture 21, slipped down to the bulging disc 41, compressed and tied. For surgical convenience, the washer 49 can be made in conjunction with a suture-locking device to eliminate suture tying. The thickness of the washer 49 should be minimal to minimize potential contact and irritation of any adjacent nerves. The suture holes in the washer 49 should be as close as possible to avoid substantial spreading of the suture 21. Suture 21 spreading may create a passage for leakage of nucleus polposus. The optional sealing patch 43 can be used in conjunction with the washer 49.

Figure 47:
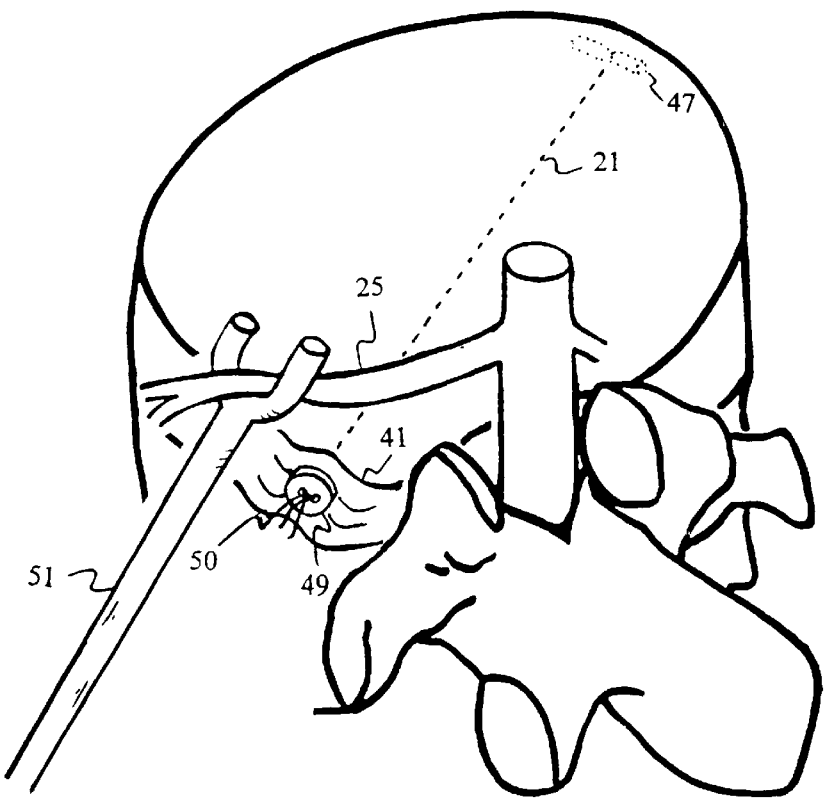
FIG. 47 shows the previously bulging disc compressed by the washer and fastened by a suture knot.

FIG. 47 shows the previously bulging disc 41 compressed by the washer 49 and fastened by a suture knot 50. To avoid potential irritation of the nerve 25 by the suture 21, the exposed suture 21 should be trimmed near the suture knot 50.

Figure 48:
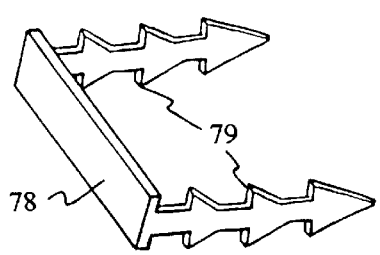
FIG. 48 depicts a staple with annulus-holding barbs configured to compress and fasten a bulging disc.
Figure 49:
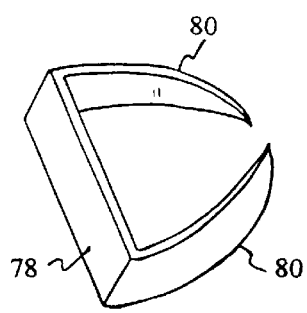
FIG. 49 depicts another type of staple with closure or shape memory legs to hold and fasten a bulging disc.

Depending on the severity of the bulge or herniation, a simple staple 78 or tack with tissue holding elements may be sufficient to fasten the weak annulus. FIG. 48 depicts a staple 78 with annulus-holding barbs 79. For minor bulging, the simple staple 78 may be sufficient to fasten the bulge. If needed, the legs of the staple 78 can be made significantly longer than the ones depicted in the drawing. FIG. 49 depicts another type of staple 78 with shape memory legs 80 to hold and fasten a bulging disc 41. The shape memory legs 80 of the staple 78 can also be made significantly longer than the ones depicted in the drawing.

Since the guiding techniques for inserting fasteners into the bulging or herniated discs 41 are similar to the ones used in relatively low risk percutaneous nuclectomy procedures and routine diagnostic discography for determining herniation, the methods used in fastening bulged or herniated discs 41 should also be low in risk and complications.

The depth of the device penetration, the overall length of the fasteners 13, and direction of fastener 13 insertion are related and are very important issues in fastening bulging or herniated discs 41. The nucleus pulposus in the central portion of the discs 41 is unlikely to be effective in gripping. With the information provided by discography or other diagnostic techniques, healthy annulus around the bulge or across the nucleus pulposus can be used to anchor the fasteners. To prevent possible contact between fasteners and nerves 25 or other tissues, protrusion of the deployed fasteners outside the disc 41 is preferred to be minimal or absent. For example, the fastener 13 may be deployed without entirely piercing through the opposite wall of the disc 41 so that only a single puncture is made, or the fastener 13 may be deployed entirely within the disc 41 such that once the delivery device 73 is removed there are no protrusions from the wall of the disc 41.

Some surgeons may like to approach the disc repair anteriorly. After retracting the abdominal contents, the fastener delivery device 73 can be guided, perhaps by fluoroscope or other means, through the disc 41 to the bulging or herniated portion. As the tip of the device reaches or nears the bulging surface, the distal half of the fastener 13 is deployed. The bulging portion of the disc 41 is gripped and pulled inward, then the fastener 13 is totally deployed to fasten the bulging disc 41. Although the anterior approach is possible, the posterior approach usually reaches the bulge more directly and is preferred.

Unlike the tissue removing approaches of percutaneous nuclectomy, chymopapain digestion or discectomy, fasteners in general directly, actively and/or elastically hold the bulging or herniated tissue back without removing the nucleus pulposus, the essential component to sustain prolonged compression when upright, and resiliently re-inflate and re-establish disc height when at rest. Therefore the bulging or herniated disc 41 may be repaired without loss of the disc 41 or nucleus pulposus.

(E) Urinary or Fecal Incontinence Repair

For the sufferers of urinary or fecal incontinence, the inconvenience and social problems are often too great to ignore, but the treatment options are far from ideal. The options range from ineffective injections to open surgeries with possible serious complications. With options such as these, it is no wonder that over $400 million is spent each year on adult diapers (Colon, Rectum and Anus, 2nd Ed., Philip Gordon, M.D., et. al., 1999).

FIGS. 50–54 show the fasteners 13 deployed or being deployed to elastically grip or close passages within the body to alleviate urinary and fecal incontinence. For urinary incontinence, the sphincter urethrae or the urethra itself are possible sites for fastening. For fecal incontinence, the rectal sphincter 54 is a potential site for fastener 13 deployment. Fasteners 13 may also be used to resiliently close the rectum, anal canal or other passages within the body. As the pressure from the bladder 53 or colon increases, the elastically fastened sphincters 54 open to allow passage of contents. After the contents are emptied, the pressure decreases and the sphincters 54 are again elastically closed by the resiliently curved fasteners 13. For patients with no neurological problems, the elastically fastened sphincters 54 may also be opened by voluntary muscles.

Regarding the insertion of the fastener delivery device 73, numerous existing guiding techniques, such as cystoscope, ultrasound, anteroposterior-lateral fluoroscopy, MRI, or others, can be used effectively and accurately to guide the insertion and deployment of the fasteners 13. Again, multiple fasteners 13 can be used to ensure proper closure of the sphincter 54.

Figure 50:
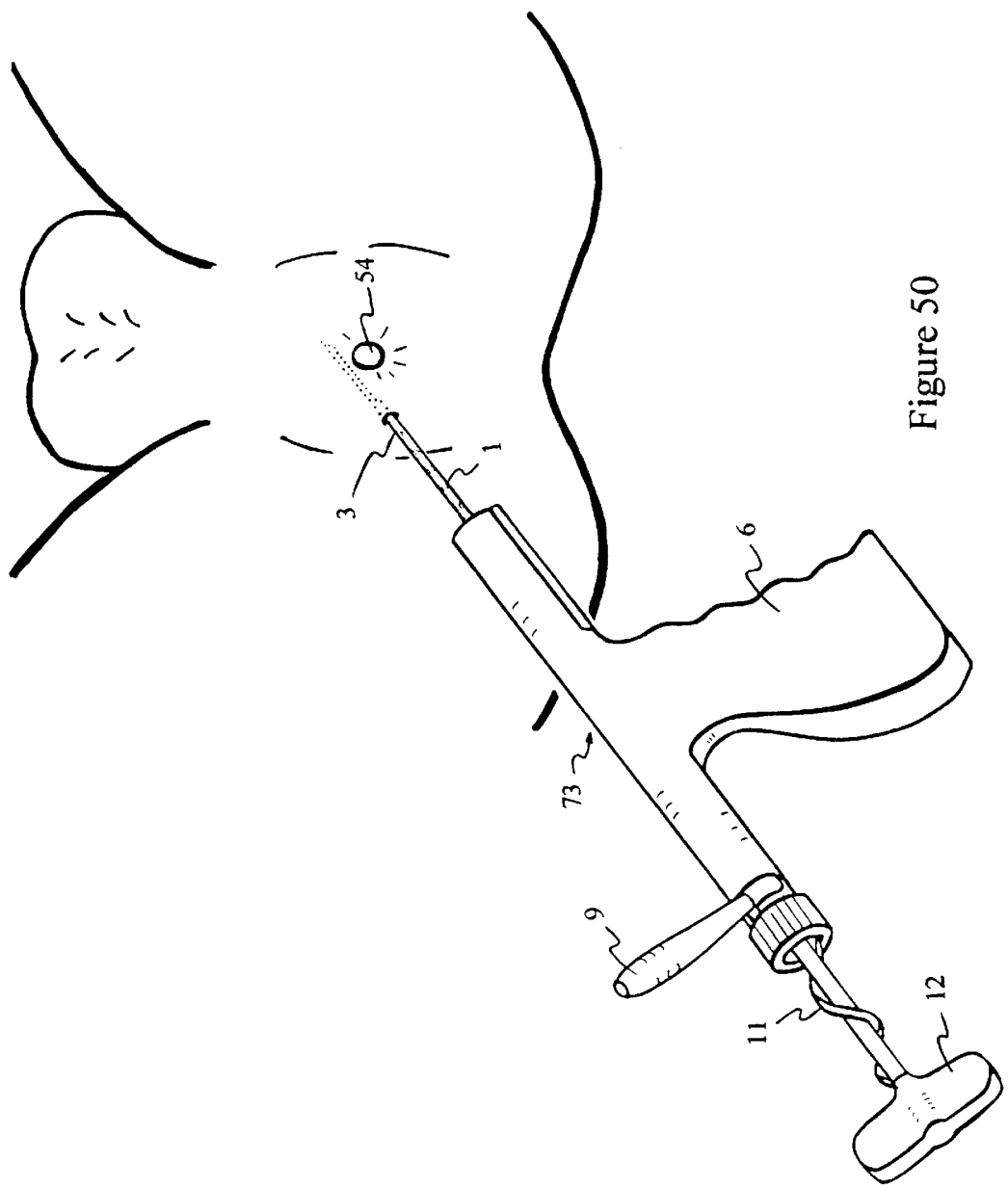
FIG. 50 depicts an insertion of the fastener delivery device to deploy an elastic fastener into a leaking anal sphincter.

FIG. 50 depicts an insertion of the fastener delivery device 73 into a leaking anal sphincter 54. When a fastener 13 is deployed, the fastener 13 elastically grips and closes a portion or the entire leaky opening of the sphincter 54.

Figure 51:
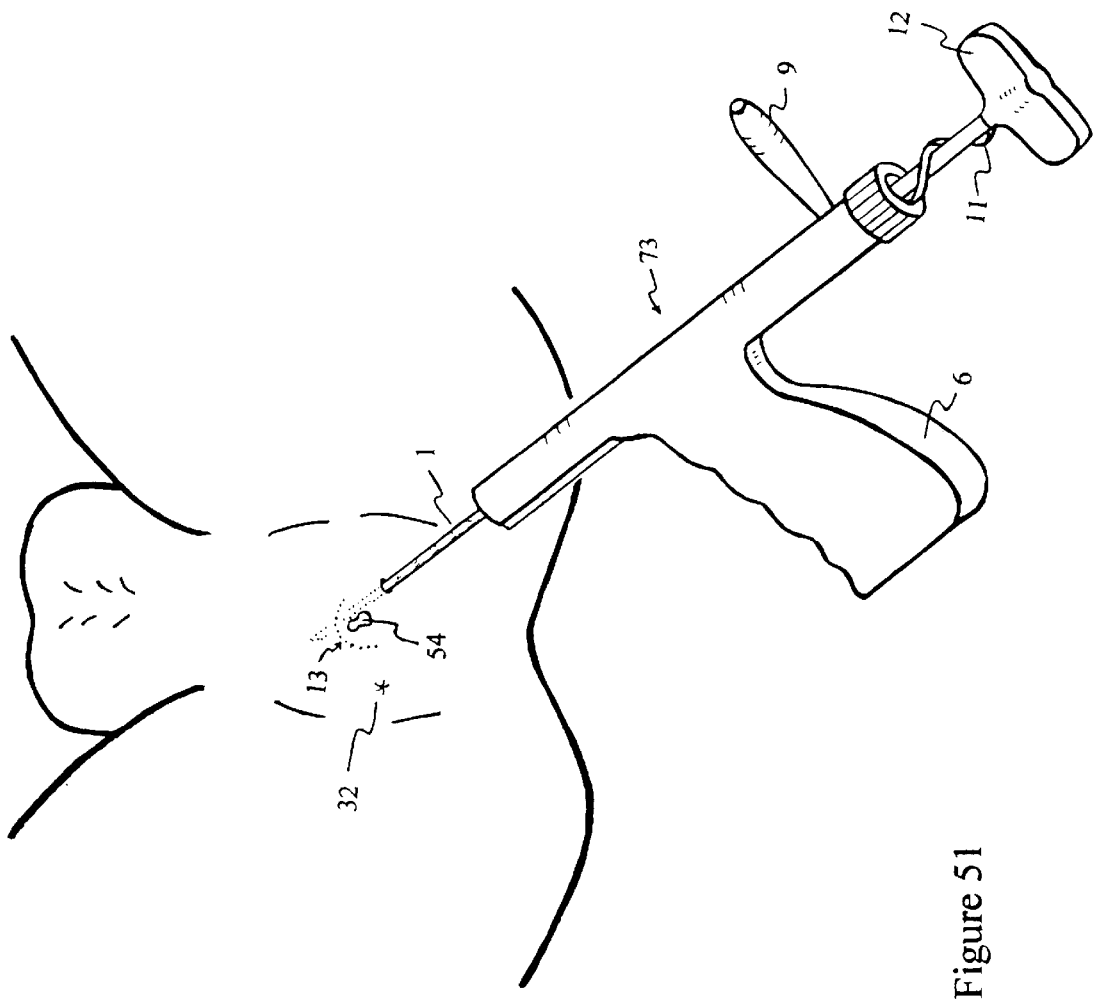
FIG. 51 depicts a deployed fastener, indicated by the dotted curvature, around the anal sphincter. The device is reinserted into another portion of the sphincter to deliver another fastener.

FIG. 51 depicts a deployed fastener 13, indicated by the dotted curvature, around the anal sphincter 54. The device 73 is reinserted into another portion of the sphincter 54 to deliver another fastener 13. Although other orientations may be used, in this example, the device entries are approximately 90° to each other.

FIG. 52 depicts an elastic closure of the anal sphincter 54, in this case with two spring-like fasteners 13 under the skin.

FIG. 53A depicts a sphincter 54 leaking due to incomplete closure. The sphincter 54 can be urinary or fecal.

FIG. 53B depicts the partial closure of the sphincter 54 by a spring-like fastener 13. In this example, the fastener 13 has very few gripping elements 14 to minimize irritation of nerves around the sphincter 54.

FIG. 53C depicts the elastic closure of the sphincter 54 by two spring-like fasteners 13.

Especially among elderly patients, the elasticity or the resiliency of the sphincter urethrae and/or the rectal sphincters varies greatly. Before inserting the fastener delivery device 73, elasticity or resiliency sensing instruments can be used to determine the closing pressure of the sphincter prior to selecting fasteners 13 with appropriate gripping forces, closure strengths and curvatures suitable for individual patients.

FIG. 54 depicts possible entries for the fastener delivery devices 73 for treating urinary and fecal incontinence. Three-dimensional guiding instrumentation may be required, especially for urinary closure. To provide instant feedback to the surgeon, a pressure sensing catheter balloon, strain gauge, or tightening detecting instrument 55 can be inserted into the leaking portion of the rectum and/or urethra As the fastener 13 deploys and tightens the leaking portion, the instrument 55 can provide instant information to the surgeon regarding the closing pressure, placement and effectiveness of the deployed fastener 13. As a result of properly deployed fasteners 13, the elastic closure of the urethra and/or anal canal can provide instant and probably long lasting improvement to incontinence problems.

For fluoroscopic image enhancement, the catheter or instrument 55 can be made or coated with radiopaque material to perfect the accuracy of the fastener delivery device 73 insertion. For ultrasound image enhancement, echogenic enhancing material can be used. Similarly, the needle 1 of the fastener delivery device 73 can also be coated with image enhancement material, such as radiopaque, echogenic, etc., for even more accurate device 73 insertion.

The delivery of spring-like fasteners 13 is considered minimally invasive and a low risk procedure. The benefits, however, can be long lasting and comparable to or exceeding the results of open surgery. Furthermore, both the device 73 and the fasteners 13 probably would not invade the inner lining of the sphincter 54 or contact potentially contaminated waste material. Therefore, infection and other complications may be significantly minimized.

(F) Carpal Tunnel Syndrome Relief

Repetitive strain injuries have become more and more common. A particularly common and debilitating form is carpal tunnel syndrome. Many who suffer from carpal tunnel syndrome depend on their manual dexterity to perform their jobs. Prolonged or frequent restrictions of hand and wrist movement pose significant problems in their job performances. Surgical relief by cutting the flexor retinaculum 57 to decompress the median nerve seems to be too drastic and may lead to complications.

FIG. 55 depicts a hand with carpal tunnel syndrome and insertion of a fastener delivery device 73 into the flexor retinaculum 57, not shown under the skin, guided by penetration markers 3 or other devices. The fasteners 13 are deployed within the retinaculum perpendicular to and over the median nerve and toward the palm. With the elastic curvature of the fastener 13 and the pliable nature of the flexor retinaculum 57, the curvature of the fastener 13 forms the shape of an arch, lifting the flexor 57 tissue, which was compressing the median nerve. FIG. 56 depicts several fasteners 13 deployed toward the palm lifting the central portion of the flexor retinaculum 57, creating a tunnel or an arch to accommodate the irritated median nerve without cutting the flexor retinaculum 57. The fasteners 13 can even be made with biodegradable materials, which degrade with time after relieving the pain and inflammation.

Figure 58:
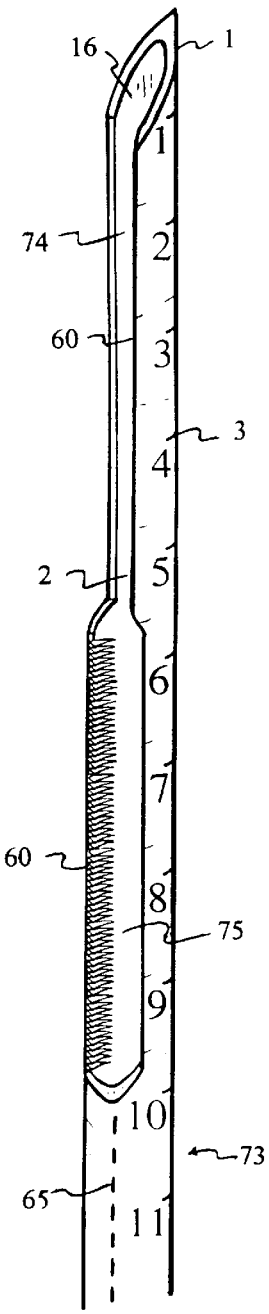
FIG. 58 depicts a needle of the fastener delivery device with a double indented slit to allow semi-deployment of either the distal or proximal portion of a fastener (not shown). Tapered fastener holding elements are indicated to anchor either semi-deployment.

(G) Double Indented Needle Slit for Versatile Tissue Manipulation and Interlocking Fasteners Depending on the surgical needs, sometimes the proximal half 77 of the fastener 13 can provide better assistance in tissue manipulation than the distal half 76 of the fastener 13. It is possible to open the slit 2 in ways to allow the deployment of either the distal portion 76 or the proximal portion 77 of the fastener 13 in semi-in-phase mode. One side of the slit 2 is indented at the distal half 74 while the other side of the slit 2 is indented at the proximal half 75, as indicated in FIG. 58. Depending on the direction of cartridge 7 rotation, relative to the needle 1, the semi-in-phase mode can bring out either the distal end 76 or the proximal end 77 of the fastener 13. Tapered fastener holding elements 60 may cover and support both semi-deployments.

Figure 57A:
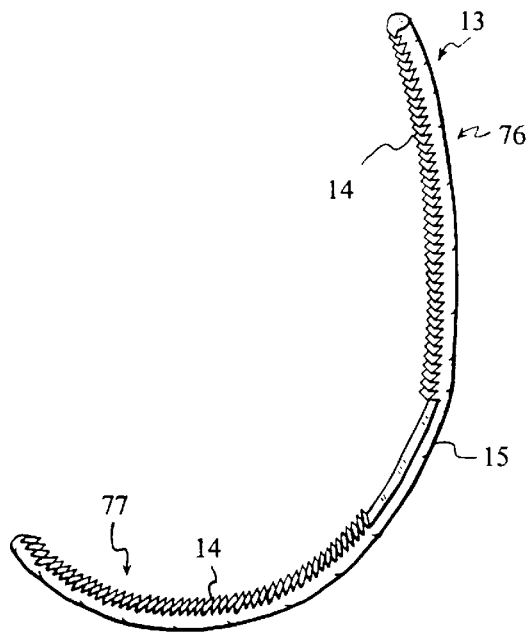
FIGS. 57A & B depict two fasteners with asymmetrical curvatures to enhance the effectiveness of inter-locking fasteners.
Figure 57B:
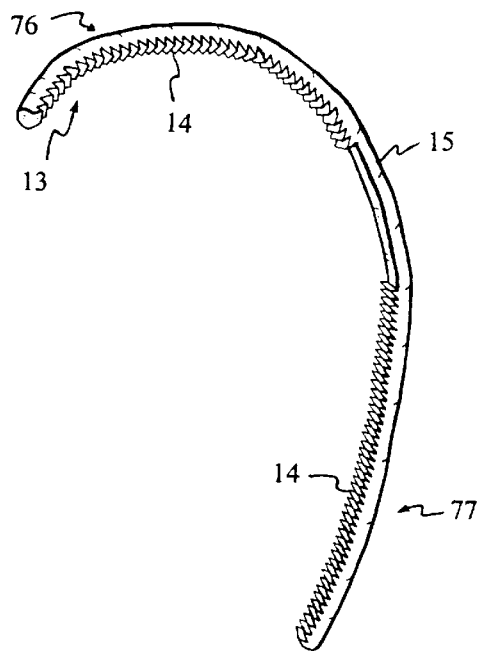

To enhance the double indented feature of the needle slit 2, the curvature of the fasteners 13 can be made asymmetrical, as shown in FIGS. 57A and B. For example, the first fastener 13 in the deploy position is made with a curvature near the proximal end 77 of the fastener 13, as shown in FIG. 57A. The following fastener 13 in the cartridge 7 is made with a curvature near the distal end 76 of the fastener 13, as shown in FIG. 57B. After semi-deploying the proximal half 77 of the first fastener 13, the tissue is tightened by pushing, then fully deploying the first fastener 13. The device 73 is slightly withdrawn and reset to out-of-phase. The following fastener 13 is advanced into the deploy position. The distal portion 76 of the second fastener 13 is semi-deployed into the tissue. Instead of tissue tightening by pushing as indicated with proximal deployment, the distal semi-deployment requires pulling of the device 73 to tighten the tissue before full deployment With tissue tightening by pushing and pulling, the fasteners 13 interlock the tissue, through one needle 1 puncture. Other than pushing and pulling on the semi-deployed fasteners 13, twisting provides yet another dimension and benefit to the tissue manipulation and interlocking fastening.

The double indented needle slit 2 and the fasteners 13 with asymmetrical curvature can be utilized to clamp arteries, restrict sphincters, reattach tissue or other uses.

(H) Tumor Artery Closure

Figure 59:
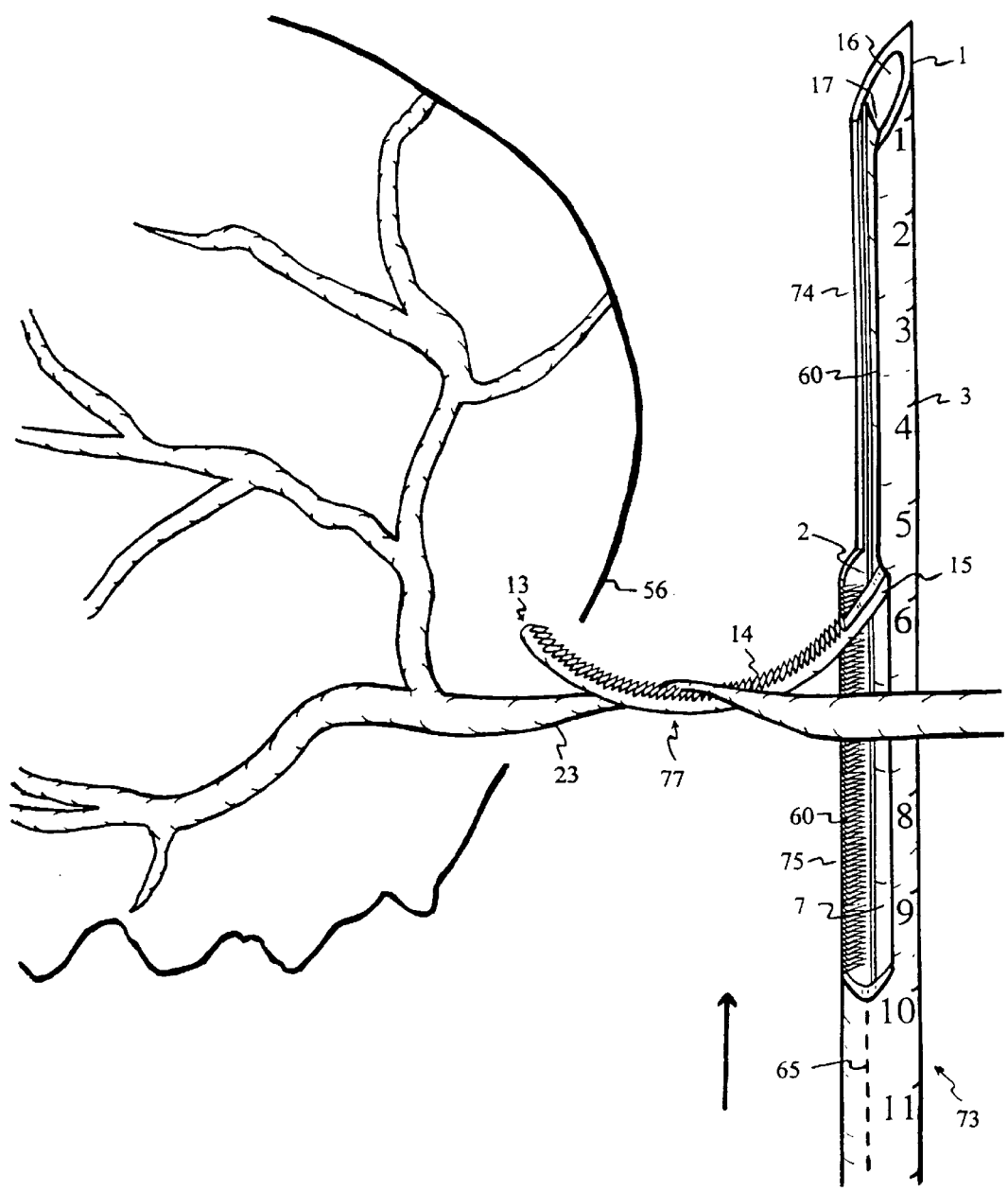
FIG. 59 depicts a proximally semi-deployed fastener pushing, compressing and restricting an artery feeding a tumor.

A tumor 56 demands far more nutrients than normal tissue. Cutting the arterial 23 blood supply may slow the growth or even diminish the size of a tumor 56 prior to surgical removal. With an angiogram, the location of the arteries 23 supplying die tumor 45 is mapped out. FIG. 59 depicts the fastener delivery device 73 inserted and guided to a tumor-feeding artery 23. With the needle slit 2 facing the artery 23, the proximal portion 77 of the fastener 13 is deployed under the artery 23. The device 73 may then be gently pushed to compress and restrict the artery 23. While pushing, the fastener 13 is fully deployed to clamp and restrict the artery 23.

Figure 60:
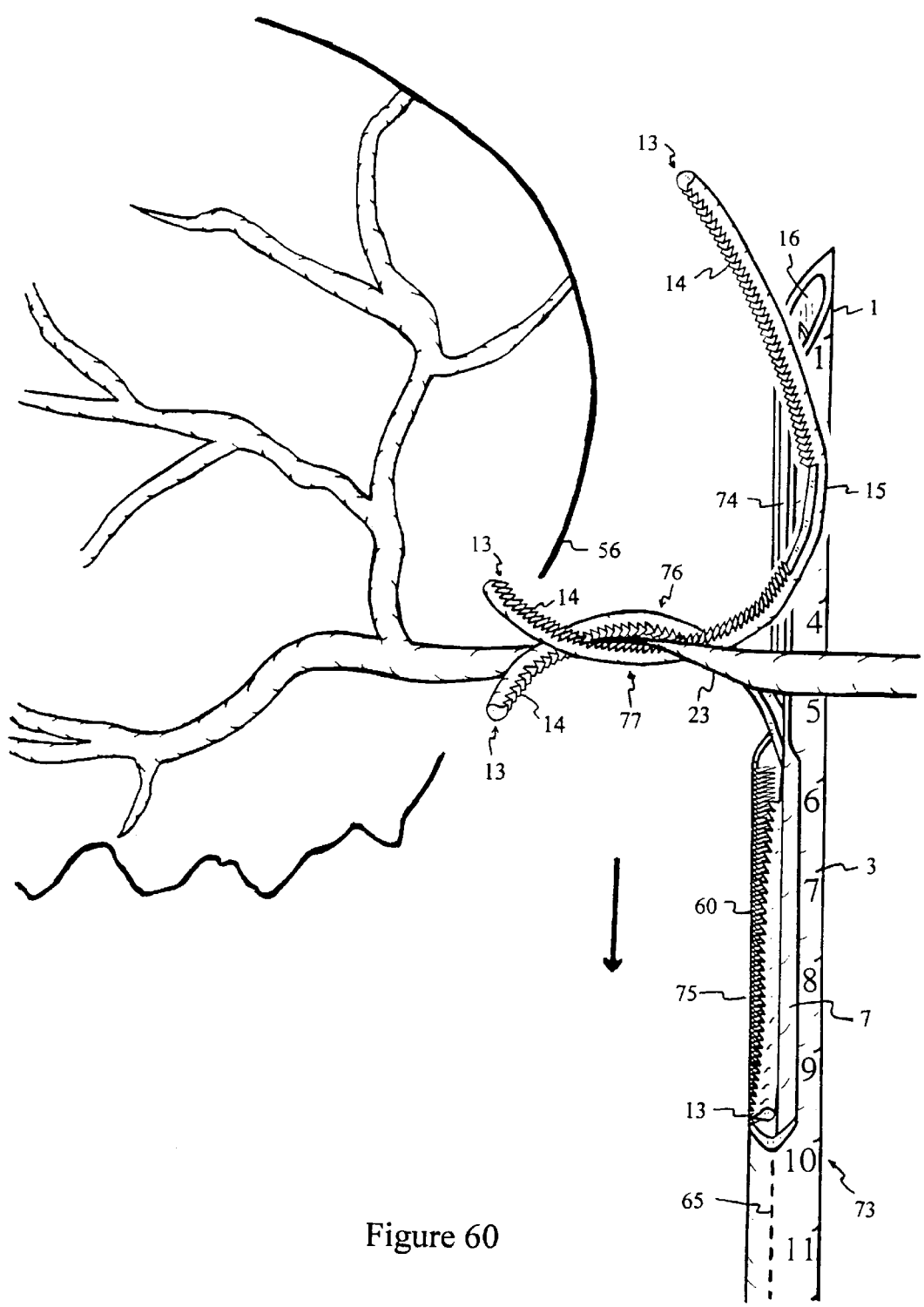
FIG. 60 shows the fastener of FIG. 59 fully deployed. Another fastener is distally semi-deployed, pulling and further restricting the blood flow of the artery.

FIG. 60 depicts the fully deployed fastener 13 from the proximal semi-deployment. The device 73 is slightly withdrawn, reset and advanced with another fastener 13 from the cartridge 7. The second fastener 13 is semi-distally deployed over the artery 23. The device 73 may then be gently pulled to hook and further restrict the artery 23. While pulling, the second fastener 13 is fully deployed to shut the blood flow. More fasteners 13 can be deployed to ensure a complete closure of the artery 23 feeding the tumor 56.

Figure 61:
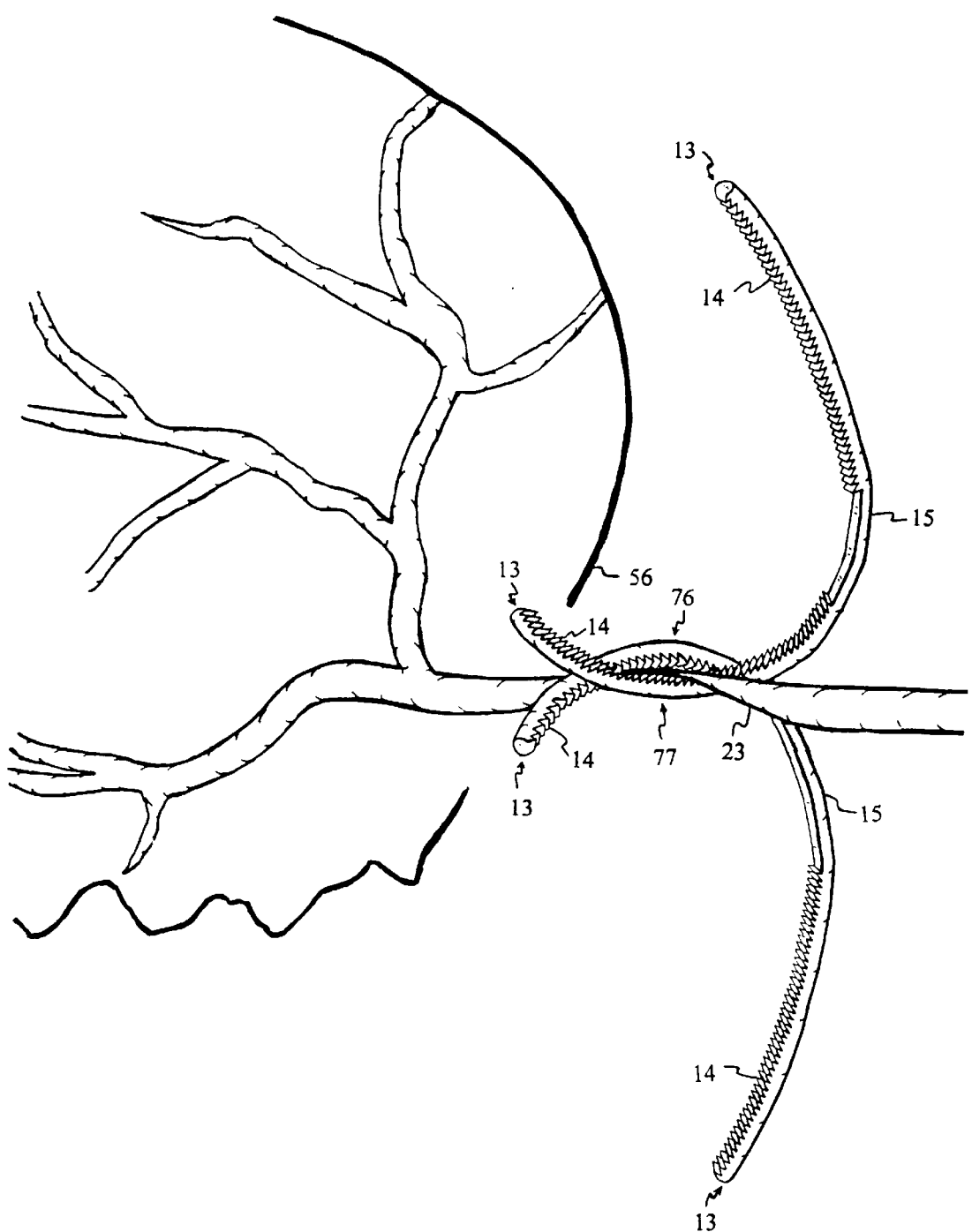
FIG. 61 depicts both fully deployed, inter-locking fasteners restricting blood flow to the tumor.

FIG. 61 depicts both fully deployed inter-locking fasteners 13 restricting blood flow to the tumor 56. In this example, the figures indicate pushing and pulling actions of the device to restrict the vessel. Twisting or rotating the semi-deployed fasteners 13 to create kinks on the vessels can also provide exceptional closure of the vessel. Also, more fasteners 13 can be deployed along the artery 23.

(I) Additional Embodiments

Fasteners 13 are frequently used in or near joints, tendons 40, ligaments or sphincters 54, where tissue movements are routine. Movement can shift the fastener and cause it to migrate. Fastener migration is rarely desirable. In fact, it can be quite damaging, especially when the fastener migrates into joints, nerves 25 or vessels. For sphincter 54 repair, migration can negate the corrected closure of the dysfunctional sphincter 54.

Figure 62:
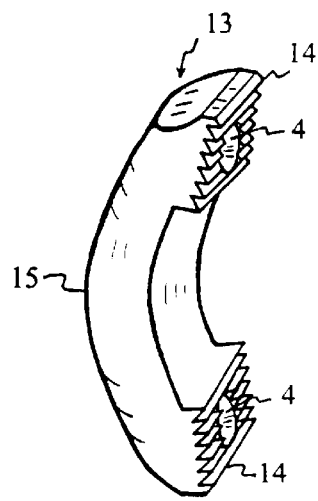
FIG. 62 depicts a fastener with tissue ingrowth holes to minimize fastener migration.

FIG. 62 depicts a fastener 13 with tissue ingrowth holes 4 to minimize possible fastener 13 migration. The holes 4 can also be in the flexible or shape memory element 15.

Figure 63:
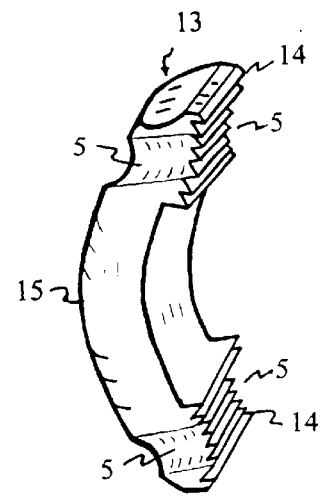
FIG. 63 depicts another fastener with tissue ingrowth grooves designed to minimize fastener migration.

FIG. 63 depicts another fastener 13 with tissue ingrowth grooves 5 designed to minimize fastener 13 migration. The grooves 5 can also be in the flexible or shape memory element 15.

Figure 64:
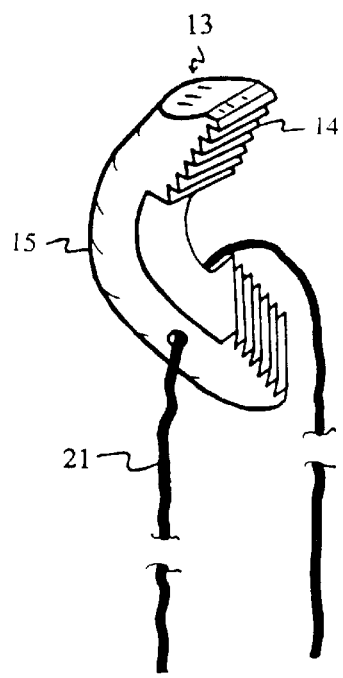
FIG. 64 depicts a fastener attached to a suture.

FIG. 64 depicts a suture 21 attached to a fastener 13 with gripping elements 14 and spring-like or shape memory element 15. The fastener 13 can be used as a suture anchor, holding the suture 21 for tissue attachment. This type of suture anchor can be used for cosmetic surgery with minimal incision.

Figure 65:
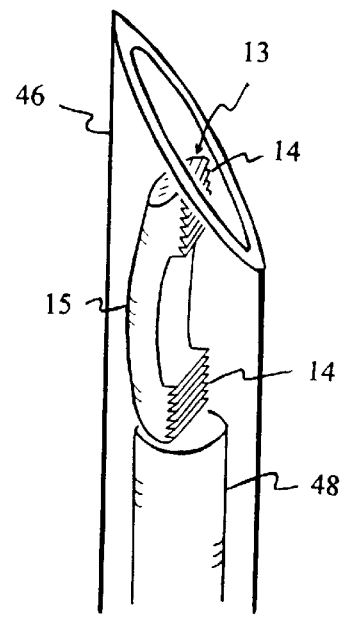
FIG. 65 depicts a simple fastener delivery device. A curved fastener is resiliently and elastically straightened in a needle followed by a plunger for deployment

The fastener delivery device 73 utilizes the mating cartridge 7, relative to the needle 1, to deploy fasteners 13 into tissue through overlapping slits 2, 8. Similar fasteners 13 can be resiliently straightened in a spinal needle 46 without the cartridge 7. Instead, a plunger 48 is fitted inside the spinal needle 46 behind the fastener 13, as shown in FIG. 65. After insertion of the needle 46 into tissue, the plunger 48 is held stationary while the needle 46 is slowly retracted or withdrawn from tissue, thereby deploying the fastener 13 out of the distal opening of the needle 46. In tissue, the fastener 13 resumes the original resilient curvature and tightly fastens onto the tissue. Multiple fasteners 13 can also be loaded into the needle 46 and deployed one at a time into different locations.

FIG. 66 depicts an exploded view and FIG. 67 an assembled view of a modular fastener 13. The modular gripping elements 14 mount into optionally recessed areas or pockets of a fastener 13 secured by stems 71, which tightly fit into gripping element holes 72. Due to the pressure exerted by the spring-like or shape memory element 15, the modular gripping elements 14 are not free to be lifted off from the main fastener body in the delivery device 73 or in tissue after deployment.

Modular gripping elements 14 can be extremely useful in some surgical repairs. For example, anal sphincter 54 fastening for fecal incontinence may adversely affect nerves 25 and blood vessels surround anal sphincters 54. It may be difficult to fasten just the nerve-free portion of the sphincter 54. The gripping elements 14 of the fastener 13 may irritate nerve fibers after the deployment of the fasteners 13. However, the gripping elements 14 are essential for anchoring the long-lasting fasteners 13 in place. With biodegradable modular gripping elements 14, the elements 14 degrade away after the fasteners 13 have been secured and tissues have grown into the tissue ingrowth holes 4 or grooves 5 (as shown in FIG. 63). Irritation of the nerve is then minimized with the remaining portion of the long-lasting elastic fasteners 13 gripping the sphincter 54.

For other surgical purposes, instead of relying on the gripping elements 14 to secure the fastener 13, the modular portion of the gripping elements 14 can be replaced with high friction coefficient materials such as silicone rubber or with tissue adhesives.

FIG. 68 depicts a needle slit 2 formed with a smooth and round curvature to minimize puncture resistance. With clockwise cartridge 7 rotation, the depicted smooth indentation accommodates distally semi-deployed fastener 13.

FIG. 69 depicts a needle slit 2, which is slanted. As the cartridge 7 and fastener 13, both not shown, rotate counterclockwise, the distal portion of the fastener 13 would initially deploy out of the slanted needle slit 2. For clockwise rotation, both distal and proximal portions protrude out of the needle 1 while the middle portion of the fastener 13 remains in the needle 1. With tissue gripping by both distal and proximal portions of the fastener 13, extra tissue manipulative power is provided to the surgeon prior to complete fastener deployment.

Figure 71:
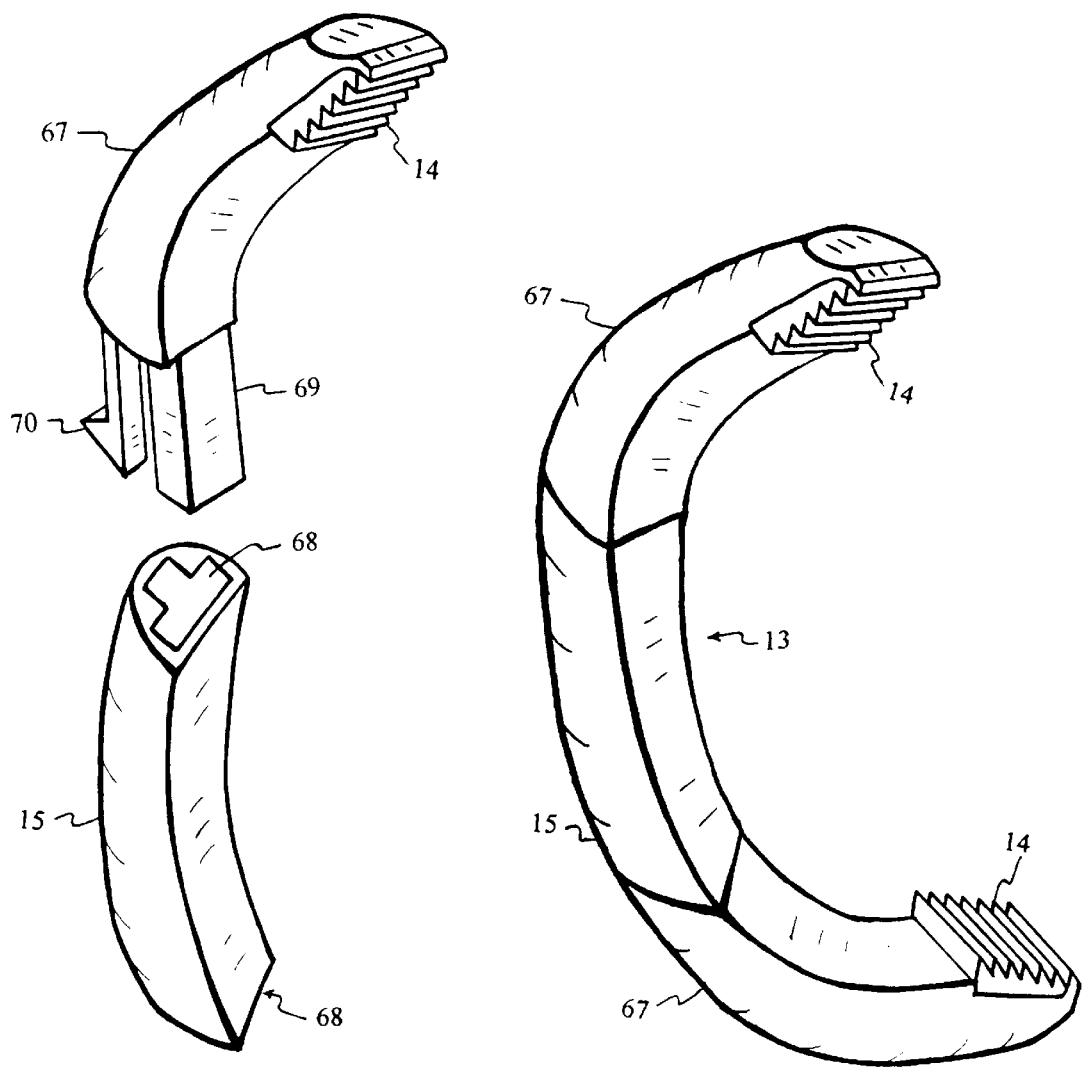
FIG. 71 depicts an assembled fastener with modular parts.
Figure 70:
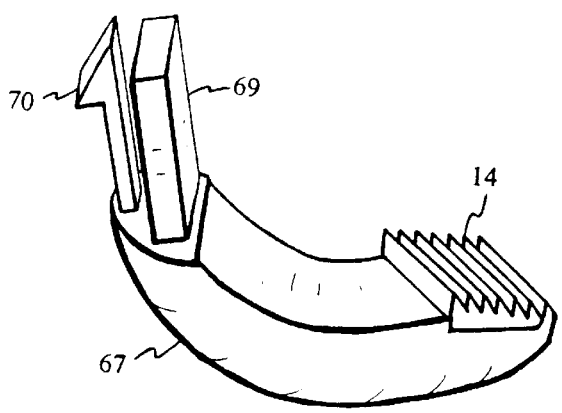
FIG. 70 depicts modular arms with connecting studs and hooks into connecting holes in a spring-like or shape memory element.

FIG. 70 depicts an exploded view and FIG. 71 an assembled view of a modular fastener 13. The modular arm 67 has a connecting stud 69 extending from the end. A connecting hook 70 also extends from the modular arm 67 adjacent the connecting stud 69. The connecting stud 69 and connecting hook 70 are placed within a connecting hole 68 within the shape memory element. The connecting hook 70 extends into a mating locking notch within the connecting hole 68, thereby locking the parts of the modular fastener 13 together.

Modular arms 67 can provide benefits which a single piece fastener 13 may not cover, especially when the arms 67 are made with different materials, size, shape, curvature, physical treatment or others. For example, the bulging portion of the annulus requires extra tension from the fastener 13 to retain the bulge. If the whole fastener 13 were made with a high tensile strength material, the whole disc would be adversely pinched out of shape by the fastener 13. However, with modular capabilities, the bulge-retaining arm 67 can be made with high tensile strength material while the anchoring arm is made with a lower strength material. As a result, the bulging annulus is retained without pinching the entire disc.

For tissue attachments into thin bones, insertion of permanent fasteners 13 can weaken the bone and may even cause future fracture from excessive load. To prevent bone weakening, biodegradable arms 67 and gripping elements 14 can be used to insert into bones, while the remaining portion of the fasteners 13 can be made with strong and permanent material.

To optimize fastening capability in some special surgical repairs, one arm 67 can be made with elastic material and the other arm 67 can be made with shape memory material.

For fasteners 13 made with a significant curvature, modular components or composition may relieve the strain of the fastener 13.

Modular components, such as the gripping elements 14, arms 67 and spring-like or shape memory element 15, of a fastener 13 can provide numerous benefits and greatly improve fastening performance. The components can be made with different materials, curvature, degradability, biocompatibility, hardness, tensile strength, tensile modulus, modulus of elasticity, size, friction coefficient, transition temperature, transformation temperature, torsion, other physical, chemical or biological characteristics. In addition to the depicted connecting means for assembling the modular components, numerous other methods and configurations can be used for a functional fastener 13.

Figure 72:
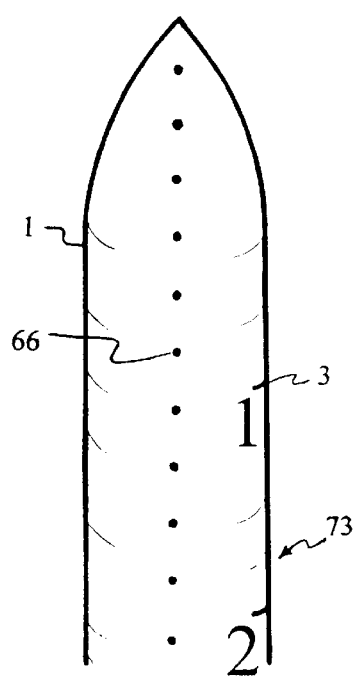
FIG. 72 depicts the back line of the needle.

FIG. 72 shows the back line 66, indicated by dots, as the other orientation line on the needle 1 which indicates direction of the back of the deploying fastener 13.

Figure 73:
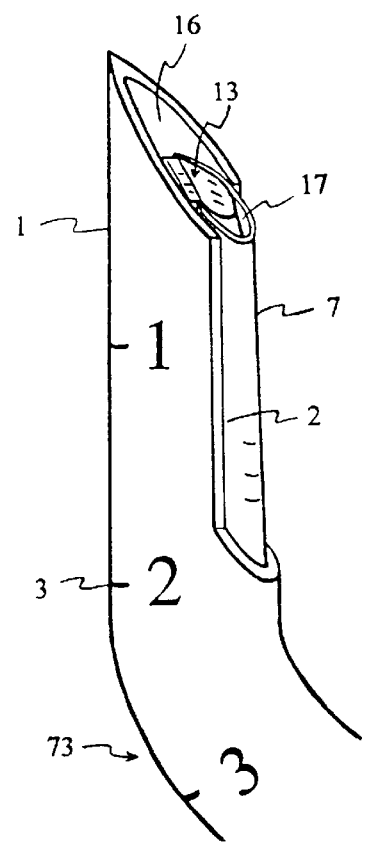
FIG. 73 depicts a curved needle with cartridge and fastener in out-of-phase mode with the needle slit.

FIG. 73 depicts a curved needle 1. For hard to reach repair sites, a curved needle 1 can allow the surgeon to access and fasten the repair site hidden behind or around adjacent tissues. Similarly, a curved needle 1 can penetrate under the skin or tissue for fastening or closure.

To accommodate cartridge 7 rotation in the curved needle 1, flexible metal, such as nickel-titanium, or flexible polymer can be used to construct the cartridge 7. Other embodiments could use a counterwound or braided torque cable.

(J) Retrieval of Deployed Fastener

As with any other surgical procedure, mistakes can occur with fastener 13 deployment. Fortunately, the deliveries of fasteners 13 described in this invention are minimaly invasive. As long as the incorrectly deployed fastener 13 does not pose problems or cause discomfort to the patient, the incorrectly deployed fastener 13 can be left in place. After learning from the error, one can then correctly deploy another fastener 13.

Some incorrectly deployed fasteners 13 can cause problems for the patients; those fasteners 13 should be removed. The best way to remove the sustained gripping fastener 13 is to endoscopically cut the mid-section of the fastener 13 before pulling each section out of the patient. If the retrieval of the problematic fastener 13 is too difficult or even impossible through an endoscopic approach, an open surgery may be necessary. Although incorrect deployment happens, the fasteners 13 and the delivery devices 73 mentioned in this invention provide superior control for the surgeons during the procedures and outstanding results for the patients when the fasteners 13 are properly deployed.

(K) Accessibility of the Fastener Delivery Device

In addition to the sustained gripping property of the fastener 13 and the versatility of the delivery device 73, another major benefit to this invention is that with proper guiding techniques, the device 73 can deliver the fasteners 13 deep into the body of the patient The needle 1 of the device 73 can be curved with a flexible cartridge 7 to accommodate rotation within the curved needle 1 to reach around organs and tissue into a target site.

Many other surgical procedures can utilize the fastener 13 and the delivery device 73. Some examples follow. The fastener 13 and delivery device 73 can endoscopically attach dislocated organs. For weight loss purposes, fasteners 13 can be used to slow stomach emptying by restricting the pyloric sphincter or pyloric canal. The fasteners 13 can also be used to attach medical devices inside the body.

The fastener 13 and the delivery device 73 can serve in numerous endoscopic procedures, which require connecting, reattaching, holding, fortifying, restricting, closing, compressing or decompressing tissues or other devices.

In brief summary, the possible benefits of the sustained gripping fasteners 13 and the delivery device 73 include: (1) grip tissue continuously, (2) minimize fastener migration, (3) minimally invasive, (4) deploy multiple fasteners within a puncture site, (5) access deep body targets, (6) support and fortify fragile tissue, (7) reattach tissue without suturing, (8) attach tissue to bone, (9) require minimal surgical space, (10) attach to other fastening devices, (11) versatile, (12) provide permanent and/or degradable fastening, (13) simple to use, (14) manipulate tissue, (15) restrict or close orifices or vessels, (16) compress or decompress tissue, and (17) provide directional fastening.

(L) Materials and Designs

The needle 1 of the fastener delivery device 73 is preferred to be made with stainless steel. Other alloys, metals, polymers, graphite composites, ceramics, or other materials can also be used. For tissue puncturing, the distal opening 16 of the needle 1 is sharpened or shaped into various configurations appropriate for the need. Normally, the needle 1 is made straight. But for hard-to-reach surgical sites, the needle 1 can be made curved with a flexible cartridge 7 to accommodate rotation in the curved needle 1. Penetration markers 3, a deploy line 65 and a back line 66 can be printed or etched on the surface of the needle 1. Lubricating coatings, such as silicone oil, plasma coating, PTFE or others, can be applied inside the needle 1 to decrease friction during the operation of the fastener delivery device 73. The lubricious coatings can also be used on the outside of the needle 1 to ease the tissue penetration.

To enhance the guiding capabilities of the needle 1 into tissue, the needle 1 can be coated with radiopaque, ultrasound echoing or other image-enhancing material.

The needle body 61, handle 6 and cartridge cap 58 can be made with polymers, metals, other materials or combinations thereof.

Stainless steel is the preferred material for making the sleeve 18, although other materials, such as polymers or other metals can be used. To fit over the curved needle 1, flexible materials, such as nickel titanium or polymers, are more suitable materials for making the sleeve 18. Likewise, the sleeve handle 20 can also be made with stainless steel, polymers or other metals.

Similar to the preferred material used for making the needle 1, the cartridge 7 is also preferred to be made with stainless steel, but materials, such as other metals, polymers, graphite composites, ceramics or others, can also be used. If the needle 1 is curved, the cartridge 7 material should be flexible enough to accommodate the rotation in the curved needle 1. Nickel titanium alloy is a strong and flexible metal, which may be suitable for making the flexible cartridge 7.

Both slits 2, 8 of the needle 1 and cartridge 7 are wider than the width of the fasteners 13. The length of the cartridge slit 8 may differ from the length of the needle slit 2. In fact, the length of the cartridge slit 8 can open longitudinally along the cartridge 7, as a trough. The open trough may provide several major benefits. The trough can serve as railings to align and maintain the fasteners 13 to face a certain direction. The opening of the trough provides more space to decrease stress and strain on the resiliently straightened fasteners 13, and it accommodates larger fasteners 13, which otherwise would not fit in a tube-like cartridge 7. The length and configuration of the cartridge slit 8 can be further modified depending on the material used to construct the cartridge 7 and on the requirement of the fasteners 13. A lubricious coating can be applied especially on the inside wall of the cartridge 7 to decrease friction during advancement of the fasteners 13.

The simple fastener-advancing unit consists of a plunger 10 driven by screw action of the advancing device 11 with a handle 12. Ideally, the pitch of the screw is spaced out precisely so that each turn or half a turn on the handle 12 advances a fastener 13 into the deploy position. Other advancing devices and mechanisms can also be used. The material used in the fastener-advancing device can be metal, polymer, ceramic or combinations of these.

The fastener delivery device 73 can come conveniently loaded with one or more fasteners 13 in the cartridge 7 chamber. However, with some mechanical or temperature assistance, it is not prohibitively difficult to load fasteners 13 into the cartridges 7 in the surgical room.

It should be clear to one skilled in the art that the current embodiments, methods and surgical sites are not the only uses for which the invention may be used. Different materials for the needles, cartridge, bodies, handles, fasteners and other components can be used. The use of this invention is also foreseen to repair, fasten, close or restrict various tissues, such as canals, organs, vessels, tendons, ligaments, muscles, cartilage, skin, bone, valves, prostheses, cosmetic lifts, tissue grafting, and other surgical procedures. Nothing in the preceding description should be taken to limit the scope of the present invention. The full scope of the invention is to be determined by the appended claims.

APPENDIX A
NUMERICAL REFERENCES IN DRAWINGS

| | |
|---|---|
| Needle | 1 |
| Slit of needle | 2 |
| Penetration markers | 3 |
| Tissue ingrowth hole | 4 |
| Tissue ingrowth groove | 5 |
| Needle handle | 6 |
| Cartridge | 7 |
| Slit of cartridge | 8 |
| Cartridge handle | 9 |
| Fastener-advancing plunger | 10 |
| Fastener-advancing device | 11 |
| Fastener-advancing handle | 12 |
| Fastener | 13 |
| Gripping elements | 14 |
| Spring-like or shape memory element | 15 |
| Needle distal opening | 16 |
| Cartridge distal opening | 17 |
| Sleeve | 18 |
| Slit of sleeve | 19 |
| Sleeve handle | 20 |
| Suture | 21 |
| Torn tissue | 22 |

-continued

APPENDIX A
NUMERICAL REFERENCES IN DRAWINGS

| | |
|---|---|
| Artery | 23 |
| Vein | 24 |
| Nerve | 25 |
| Meniscus | 26 |
| Capsule | 27 |
| Anterior cruciate ligament, ACL | 28 |
| Ligament holder | 29 |
| Device guiding tracks | 30 |
| Ligament holder handle | 31 |
| Puncture site | 32 |
| Trocar | 33 |
| Cannula | 34 |
| Drill | 35 |
| Bone stop | 36 |
| Cannula stop | 37 |
| Bone | 38 |
| Humerus | 39 |
| Tendon | 40 |
| Bulging or herniated disc | 41 |
| Spinal cord | 42 |
| Sealing patch | 43 |
| Screw | 44 |
| Washer with locking snub | 45 |
| Spinal needle | 46 |
| Dumbbell shaped rod | 47 |
| Plunger | 48 |
| Washer | 49 |
| Suture knot | 50 |
| Nerve retractor | 51 |
| Anus | 52 |
| Bladder | 53 |
| Sphincter | 54 |
| Tightening detecting instrument | 55 |
| Tumor | 56 |
| Flexor retinaculum | 57 |
| Cartridge cap | 58 |
| Sleeve-sliding track | 59 |
| Tapered fastener holding elements | 60 |
| Needle Body | 61 |
| Cartridge body | 62 |
| Variable pitch thread | 63 |
| Locking teeth | 64 |
| Deploy line | 65 |
| Back line | 66 |
| Arm | 67 |
| Connecting hole | 68 |
| Connecting stud | 69 |
| Connecting hook | 70 |
| Gripping element stem | 71 |
| Gripping element hole | 72 |
| Fastener delivery device | 73 |
| Distal portion of needle slit | 74 |
| Proximal portion of needle slit | 75 |
| Distal portion of fastener | 76 |
| Proximal portion of fastener | 77 |
| Staple | 78 |
| Barbs on staple | 79 |
| Shape memory staple legs | 80 |
| Ligament holding device | 81 |

We claim:

1. A method of delivering a resilient fastener into human or animal tissue to repair a bulging or herniated intervertebral disc, the method comprising the steps of:

(a) inserting a needle into the bulge of the intervertebral disc, said needle having at least one resilient fastener constrained in an extended, open position therein;

(b) deploying said resilient fastener into the intervertebral disc;

(c) causing said resilient fastener to move towards a predisposed clamping position;

(d) and withdrawing said needle.

2. The method of claim 1 further comprising the steps of:

(e) passing said needle through the intervertebral disc;

(f) compressing the bulge of the intervertebral disc;

(g) and deploying said fastener such that a first end of said fastener extends from one side of the intervertebral disc and a second end grips the bulge thereby maintaining the compression of the bulge.

3. The method of claim 2 wherein said second end extends at least partially from another side of said intervertebral disc.

4. The method of claim 2 wherein when said needle passes through the bulging or herniated intervertebral disc, and said needle creates an opening, the method further comprising the step of:

(h) deploying a sealing member to seal the opening in the bulging or herniated intervertebral disc.

5. The method of claim 4 further comprising the step of:

(i) deploying a second sealing member to seal a second opening created at a distal end of the fastener.

6. A method of delivering a fastener into a herniated or bulging intervertebral disc, the method comprising the steps of:

a) compressing a bulge or herniation of the intervertebral disc;

b) and deploying a fastener into the intervertebral disc to hold the herniation or bulge in a compressed position.

7. The method of claim 6 wherein said fastener resiliently holds the herniation or bulge in the compressed position.

8. The method of claim 6 wherein said fastener device is a screw and said screw is rotatably inserted into the intervertebral disc.

9. The method of claim 8 wherein a washer is attached on an end of said screw.

10. The method of claim 8 wherein said screw has a variable pitch thread, thereby allowing the user to compress the intervertebral disc as said screw is rotated into the intervertebral disc.

11. The method of claim 8 wherein said screw has a locking device to lock said screw in place within the intervertebral disc.

12. The method of claim 6 wherein said fastener device comprises a suture used to tie and compress the bulge in the intervertebral disc.

13. The method of claim 12 wherein said suture is formed of metal.

14. The method of claim 12 wherein said suture has an anchoring device.

15. The method of claim 12 wherein a washer is tied to the intervertebral disc by said suture.

16. The method of claim 6 wherein said fastener is a tack which is pressed into the bulge.

17. The method of claim 6 wherein said fastener is a staple which is pressed into the bulge.

18. The method of claim 6 wherein said fastener is a clamp which is positioned around the bulge.

19. The method of claim 6 wherein said fastener is a tissue anchor used to press the bulging tissue against the intervertebral disc.

20. A treatment apparatus for compressing a bulge or herniation of an intervertebral disc, comprising:

at least one tissue holding element located proximate a first end of said treatment apparatus, compression means for compressing the bulging or herniation of the intervertebral disc, said compression means being located proximate a second end of said treatment apparatus, and a sealing patch for sealing an opening in said herniation, wherein said first end is attached to said second end by a middle portion.

21. The treatment apparatus of claim 20 wherein said middle portion is formed of a resilient material.

22. The treatment apparatus of claim 21 wherein said resilient material is a shape memory material.

23. The treatment apparatus of claim 20 wherein said at least one tissue holding element is threading of a screw and said compression means is a head located at a second end of said screw.

24. The treatment apparatus of claim 23 wherein said threading has a variable pitch.

25. The treatment apparatus of claim 23 further comprising a washer, wherein said washer is placed around a second end of said screw.

26. The treatment apparatus of claim 25 wherein said washer further comprises a locking nub.

27. The treatment apparatus of claim 26 further comprising a sealing patch for sealing a herniation.

28. The treatment apparatus of claim 26 wherein said sealing patch is elastic.

29. The treatment apparatus of claim 26 wherein said sealing patch is biocompatible.

30. The treatment apparatus of claim 20 wherein said treatment apparatus is a tack.

31. The treatment apparatus of claim 30 wherein said at least one tissue holding element is a barb on said tack.

32. The treatment apparatus of claim 20 wherein said at least one tissue holding element is a ridge extending from a surface of said treatment apparatus.

33. The treatment apparatus of claim 20 wherein said at least one tissue holding element is a rod and wherein said rod is attached to a suture which is sized and configured to extend through at least a portion of the bulging or herniated disc, said suture forming at least a portion of said compression means.

34. The treatment apparatus of claim 33 wherein said compression means further comprises a washer.

35. The treatment apparatus of claim 20 wherein said at least one tissue holding element is formed of a shape memory material.

36. The treatment apparatus of claim 20 wherein said at least one tissue holding element forms a part of a fastener for holding tissue, said fastener having a first end, a second end and a middle portion, said at least one tissue holding element located on said first end of said fastener, at least a portion of said fastener being formed of a resilient material, said resilient material predisposing said fastener to form a curved or bent shape, wherein said fastener has an open position and a closed position, wherein in said open position, said fastener is configured to pass through a generally cylindrical passage, wherein in said closed position, said fastener assumes said curved or bent shape, said at least one tissue holding element located on a concave side of said fastener when said fastener is in said closed position, thereby grasping the tissue with said at least one tissue holding element.

37. A delivery system for delivering a treatment apparatus, comprising:

a treatment apparatus, including:
at least one tissue holding element,
and compression means for compressing the bulging or herniation of the intervertebral disc, and a fastener delivery device, including:
a hollow, generally tubular needle having a distal end, a proximal end and a passage extending therethrough,
a handle coupled with said needle,
and a fastener deployment actuator coupled with said needle.

38. The delivery system of claim 37 further comprising a sleeve locatable around said needle.

39. The fastener delivery device of claim 38 wherein said sleeve further comprises a tissue manipulation element located on a distal end thereof.

40. The fastener delivery device of claim 38 further comprising a sliding track along said needle and wherein said sleeve moves along said sliding track.

41. The fastener delivery device of claim 37 further comprising a slit extending through a side of said hollow, tubular needle.

* * * * *